(12) United States Patent
Zeira et al.

(10) Patent No.: US 12,161,832 B2
(45) Date of Patent: Dec. 10, 2024

(54) MEDICAL AGENT DISPENSING SYSTEMS, METHODS, AND APPARATUSES

(71) Applicant: DEKA Products Limited Partnership, Manchester, NH (US)

(72) Inventors: Eitan C. Zeira, Hollis, NH (US); Jason A. Demers, Manchester, NH (US); Dean Kamen, Bedford, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 955 days.

(21) Appl. No.: 17/188,301

(22) Filed: Mar. 1, 2021

(65) Prior Publication Data
US 2022/0273923 A1    Sep. 1, 2022

(51) Int. Cl.
*A61M 37/00* (2006.01)
*A61M 5/14* (2006.01)
*A61M 5/145* (2006.01)

(52) U.S. Cl.
CPC ........ *A61M 37/0015* (2013.01); *A61M 5/145* (2013.01); *A61M 2037/0023* (2013.01);
(Continued)

(58) Field of Classification Search
CPC ...... A61M 37/0015; A61M 2037/0023; A61M 2037/003; A61M 2202/0007;
(Continued)

(56) References Cited

U.S. PATENT DOCUMENTS 3,048,171 A    8/1962   Grau
3,539,455 A    11/1970  Clark, Jr.
(Continued)

FOREIGN PATENT DOCUMENTS

EP    1301236 B1    10/2004
EP    1187653 B1    3/2010
(Continued)

OTHER PUBLICATIONS

"Injection into the Dermal Skin Layer." Intradermal Drug Delivery, Idevax, https://idevax.com/device/intradermal-injection/. (Retrieved Jan. 6, 2023).
(Continued)

*Primary Examiner* — Amber R Stiles
(74) *Attorney, Agent, or Firm* — Toohey Law Group, LLC; Kevin D. Mandro

(57) ABSTRACT

A medical agent delivery device may comprise a collapsible reservoir and a base portion including at least one microneedle on a first face and on an opposing second face. Each microneedle on the first face may fluidically communicate with a microneedle on the second face. The device may further comprise an elastomeric housing attached to the first face. The reservoir and the at least one microneedle on the first face of the base portion may be within the elastomeric housing. The device may further comprise a displaceable spacer having a first position in which the spacer supports the reservoir in spaced relation to the at least one microneedle on the first side of the base portion. When the spacer is in a second position, the elastomeric housing may be configured to press the reservoir into the at least one microneedle on the first side of the base portion.

26 Claims, 30 Drawing Sheets

(52) U.S. Cl.
CPC .............. *A61M 2037/003* (2013.01); *A61M 2202/0007* (2013.01); *A61M 2205/3368* (2013.01); *A61M 2205/36* (2013.01)

(58) Field of Classification Search
CPC ...... A61M 2205/3368; A61M 2205/36; A61M 2005/3254; A61M 5/3298; A61M 2005/314; A61M 5/2033; A61M 2037/0061; A61M 5/145; A61M 2005/14506

See application file for complete search history.

(56) References Cited

U.S. PATENT DOCUMENTS

| | | |
|---|---|---|
| 3,731,681 A | 5/1973 | Blackshear et al. |
| 3,964,482 A | 6/1976 | Gerstel et al. |
| 4,552,561 A | 11/1985 | Eckenhoff et al. |
| 4,668,231 A | 5/1987 | De Vries et al. |
| 4,772,263 A | 9/1988 | Dorman et al. |
| 4,969,873 A | 11/1990 | Steinbach et al. |
| 5,045,064 A | 9/1991 | Idriss |
| 5,250,023 A | 10/1993 | Lee et al. |
| 5,390,671 A | 2/1995 | Lord et al. |
| 5,591,123 A | 1/1997 | Sibalis et al. |
| 5,879,326 A | 3/1999 | Godshall et al. |
| 5,957,895 A | 9/1999 | Sage et al. |
| 5,983,136 A | 11/1999 | Kamen |
| 6,132,755 A | 10/2000 | Eicher et al. |
| 6,186,982 B1 | 2/2001 | Gross et al. |
| 6,190,367 B1 | 2/2001 | Hall |
| 6,280,148 B1 | 8/2001 | Zengerle et al. |
| 6,334,856 B1 | 1/2002 | Allen et al. |
| 6,358,239 B1 | 3/2002 | Rake et al. |
| 6,360,888 B1 | 3/2002 | McIvor et al. |
| 6,406,276 B1 | 6/2002 | Normand et al. |
| 6,471,903 B2 | 10/2002 | Sherman et al. |
| 6,533,949 B1 | 3/2003 | Yeshurun et al. |
| 6,537,242 B1 | 3/2003 | Palmer |
| 6,537,249 B2 | 3/2003 | Kriesell et al. |
| 6,558,361 B1 | 5/2003 | Yeshurun |
| 6,603,987 B2 | 8/2003 | Whitson |
| 6,611,707 B1 | 8/2003 | Prausnitz et al. |
| 6,656,147 B1 | 12/2003 | Gertsek et al. |
| 6,743,211 B1 | 6/2004 | Prausnitz et al. |
| 6,924,087 B2 | 8/2005 | Yeshurun et al. |
| 7,025,774 B2 | 4/2006 | Freeman et al. |
| 7,250,037 B2 | 7/2007 | Shermer et al. |
| 7,285,113 B2 | 10/2007 | Yeshurun |
| 7,344,499 B1 | 3/2008 | Prausnitz et al. |
| 7,588,552 B2 | 9/2009 | Yeshurun et al. |
| 7,648,484 B2 | 1/2010 | Yeshurun et al. |
| 7,985,203 B2 | 7/2011 | Haueter et al. |
| 7,998,119 B2 | 8/2011 | Yeshurun et al. |
| 8,007,466 B2 | 8/2011 | Yeshurun et al. |
| 8,070,745 B2 | 12/2011 | Gibson et al. |
| 8,162,901 B2 | 4/2012 | Gonnelli |
| 8,361,037 B2 | 1/2013 | Gonnelli |
| 8,512,287 B2 | 8/2013 | Cindrich et al. |
| 8,597,257 B2 | 12/2013 | Modi |
| 8,684,968 B2 | 4/2014 | Genosar |
| 8,696,619 B2 | 4/2014 | Schnall |
| 8,784,383 B2 | 7/2014 | Cole et al. |
| 8,795,230 B2 | 8/2014 | Schoonmaker et al. |
| 8,858,498 B2 | 10/2014 | West |
| 8,920,375 B2 | 12/2014 | Gonnelli |
| 9,011,392 B2 | 4/2015 | McAllister et al. |
| 9,017,289 B2 | 4/2015 | Backes |
| 9,174,006 B2 | 11/2015 | Vosseler et al. |
| 9,302,903 B2 | 4/2016 | Park et al. |
| 9,375,529 B2 | 6/2016 | Searle et al. |
| 9,415,198 B2 | 8/2016 | McAllister |
| 9,445,762 B2 | 9/2016 | Sullivan et al. |
| 9,693,894 B2 | 7/2017 | Tai et al. |
| 10,350,289 B2 | 7/2019 | Meyer et al. |
| 10,398,856 B2 | 9/2019 | Clemenz et al. |
| 10,463,806 B2 | 11/2019 | Hoffmann |
| 10,828,429 B2 | 11/2020 | Admati et al. |
| 10,967,117 B2 | 4/2021 | Lanigan |
| 2001/0053891 A1 | 12/2001 | Ackley |
| 2003/0135166 A1 | 7/2003 | Gonnelli |
| 2004/0098014 A1 | 5/2004 | Flugeman et al. |
| 2005/0137536 A1 | 6/2005 | Gonnelli |
| 2006/0051404 A1 | 3/2006 | Yeshurun et al. |
| 2008/0015516 A1 | 1/2008 | Lavi |
| 2008/0015522 A1 | 1/2008 | Yeshurun et al. |
| 2008/0091226 A1 | 4/2008 | Yeshurun et al. |
| 2008/0183144 A1 | 7/2008 | Trautman et al. |
| 2009/0011158 A1 | 1/2009 | Yeshurun |
| 2009/0012494 A1 | 1/2009 | Yeshurun et al. |
| 2009/0048557 A1 | 2/2009 | Yeshurun et al. |
| 2009/0054842 A1 | 2/2009 | Yeshurun et al. |
| 2009/0099522 A1 | 4/2009 | Kamen et al. |
| 2009/0157094 A1 | 6/2009 | Yeshurun et al. |
| 2009/0198189 A1 | 8/2009 | Simons |
| 2009/0247953 A1 | 10/2009 | Yeshurun et al. |
| 2009/0259176 A1* | 10/2009 | Yairi ................ A61M 35/10 604/290 |
| 2010/0224590 A1 | 9/2010 | Yeshurun et al. |
| 2011/0046557 A1 | 2/2011 | Lee et al. |
| 2011/0213335 A1 | 9/2011 | Burton et al. |
| 2011/0238038 A1 | 9/2011 | Sefi et al. |
| 2011/0282298 A1 | 11/2011 | Agian et al. |
| 2013/0110043 A1 | 5/2013 | Levin |
| 2013/0110053 A1 | 5/2013 | Yoshino et al. |
| 2013/0197438 A1* | 8/2013 | Yang ................ A61M 5/1452 604/113 |
| 2013/0296791 A1 | 11/2013 | Segev et al. |
| 2014/0296708 A1 | 10/2014 | Flaherty et al. |
| 2014/0350514 A1 | 11/2014 | Levin |
| 2015/0011976 A1 | 1/2015 | Vouillamoz et al. |
| 2015/0038911 A1 | 2/2015 | Levin et al. |
| 2015/0151097 A1 | 6/2015 | Carnahan et al. |
| 2016/0144137 A1 | 5/2016 | Shapiro |
| 2016/0158514 A1 | 6/2016 | Stoeber et al. |
| 2016/0184571 A1 | 6/2016 | Admati |
| 2016/0199581 A1 | 7/2016 | Cachemaille et al. |
| 2016/0354589 A1 | 12/2016 | Katsunori et al. |
| 2017/0043148 A1 | 2/2017 | Baker et al. |
| 2018/0185623 A1 | 7/2018 | Lesher et al. |
| 2018/0361132 A1 | 12/2018 | Oorschot et al. |
| 2019/0111218 A1 | 4/2019 | Beyers et al. |
| 2019/0160273 A1 | 5/2019 | Baker et al. |
| 2019/0269895 A1 | 9/2019 | Nguyen et al. |
| 2020/0078575 A1 | 3/2020 | Mansoor et al. |
| 2021/0023354 A1 | 1/2021 | Mansoor et al. |
| 2021/0308439 A1 | 10/2021 | Admati et al. |
| 2022/0273877 A1 | 9/2022 | Kamen et al. |
| 2022/0273924 A1 | 9/2022 | Kamen et al. |
| 2022/0273925 A1 | 9/2022 | Zeira et al. |
| 2023/0264006 A1 | 8/2023 | Kamen et al. |
| 2023/0277759 A1 | 9/2023 | Kamen et al. |
| 2024/0024566 A1 | 1/2024 | Kamen et al. |

FOREIGN PATENT DOCUMENTS

| | | |
|---|---|---|
| EP | 2459267 B1 | 12/2017 |
| EP | 3639873 A1 | 4/2020 |
| JP | 2014 124434 A | 7/2014 |
| WO | WO 2011/027586 A1 | 3/2011 |
| WO | WO 2011/146166 A1 | 11/2011 |
| WO | WO2020023804 | 1/2020 |
| WO | WO 2021/121589 A1 | 6/2021 |
| WO | WO 2022/149833 A1 | 7/2022 |

OTHER PUBLICATIONS

Chin, Sae Hoon, et al. "Selective Dermal Rejuvenation Using Intradermal Injection of Carbon Dioxide and Hyaluronic Acid for Facial Wrinkles." Annals of Plastic Surgery, vol. 70, No. 6, 2013, pp. 628-631, doi:10.1097/SAP.0b013e31823fa958.

(56) References Cited

OTHER PUBLICATIONS

Leach, Chris. Faster Insulin: Short and Sweet. Insulin Nation, Mar. 26, 2013, https://insulinnation.com/treatment/medicine-drugs/faster-insulin-short-and-sweet/.

Lips, Bram, and Robert Puers. "Three Step Deep Reactive Ion Etch for High Density Trench Etching." Journal of Physics: Conference Series, vol. 757, 2016, pp. 1-5., https://doi.org/10.1088/1742-6596/757/1/012005.

Path Case Study: Development and Use of the Uniject Device. Path, Nov. 2009, https://www.path.org/publications/files/OTP_uniject_cs.pdf.

Streicher, Jessica. "Verapido Medical GmbH: Small Needles with a Huge Effect." Healthcare Industry BW, Biopro Baden-Württemberg GmbH, Feb. 3, 2014, https://www.gesundheitsindustrie-bw.de/en/article/news/verapido-medical-gmbh-small-needles-with-a-huge-effect.

Verapido Medical Administering Drugs Into the Skin. Verapido Medical—Hahn-Schickard, https://www.hahn-schickard.de/en/spin-off-companies/verapido-medical. (Retrieved Jan. 6, 2023).

U.S. Appl. No. 18/087,058, filed Dec. 22, 2022.

*6 VIPS Phase 1 Technical Note Compact Prefilled Auto-Disable Devices (CPADs)*. [online] Vaccine Innovation Prioritisation Strategy Vaccine Alliance Project, pp. 1-30. https://www.gavi.org.news/document-library/6-vips-phase-i-technical-note-compact-prefilled-auto-disable-devices-pdf (Retrieved May 6, 2021).

*Drug Delivery—Recent Developments in Microneedle Technology for Transdermal Drug Delivery & Vaccination* [online] Drug Development & Delivery, pp. 1-7. Jul./Aug. 2012. https://drug-dev.com/recent-developments-in-microneedle-technology-for-transdermal-drug-delivery-vaccination/.

*Intracutaneous Microneedle System*, [online] Zosano Pharma, pp. 1-2. https://www.zosanopharma.com/technology/ (Retrieved Jul. 15, 2021).

*Microneedle Coronavirus Vaccine Triggers Immune Response in Mice*, [online] NIH Research Matters, pp. 1-4. Apr. 14, 2020. https://www.nih.gov/news-events/nih-research-matters/microneedle-coronavirus-vaccine-triggers-immune-response-mice.

*Mimix Therapies* [online] Vaxess Technologies, pp. 1-9. https://www.vaxess.com/mimix-therapies (Retrieved Jul. 14, 2021).

*Solving the Challenges of Logistics, Infrastructure, and Manufacturing Capacity for COVID-19 Vaccines* [online] Vaxess Technologies pp. 1. https://www.vaxess.com/s/VAXESS-MIMIX-COVID-One-Page-12112020.pdf (Retrieved Jul. 14, 2021).

U. S. Food and Drug Administration. *FYs 2013-2017 GDUFA Science and Research Report: Transdermal Drug Products*. [online], pp. 1-15, https://www.fda.gov/industry/generic-drug-user-fee-amendments/fys-2013-2017-gdufa-science-and-reseach-report-transdermal-drug-products. (Retrieved May 6, 2021).

*VAX-ID Accurate Intradermal Injection* [online], IDEVAX, pp. 1-2, https://idevax.com/wp-content/uploads/2021/02/Vax-ID_SpecSheet_version2021_01B_EN-gecomprimeerd.pdf (Retrieved May 7, 2021).

Bae, Won-Gyu, et al. "Snake Fang-Inspired Stamping Patch for Transdermal Delivery of Liquid Formulations." [online] *Science Translational Medicine*, vol. 11, No. 503, Jul. 31, 2019, pp. 1-12, doi: 10.1126/scitranslmed.aaw3329.

Boopathy, Archana V., et al. "Enhancing Humoral Immunity via Sustained-Release Implantable Microneedle Patch Vaccination." [online] *Proceedings of the National Academy of Sciences of the United States of America*, vol. 116, No. 33, Jul. 29, 2019, pp. 16473-16478, doi:10.1073/pnas.1902179116.

Briggaman, R. A., and C. E. Wheeler. "The Epidermal Dermal Junction." [online] *Journal of Investigative Dermatology*, vol. 65, No. 1, Jul. 1975, pp. 71-84, doi:10.1111/1523-1747.ep12598050.

Carter, Darrick, et al. "The Adjuvant GLA-AF Enhances Human Intradermal Vaccine Responses." [online] *Science Advances*, vol. 4, No. 9, Sep. 12, 2018, pp. 1-9, doi:10.1126/sciadv.aas9930.

Chanda, Arnab. "Biomechanical Modeling of Human Skin Tissue Surrogates." [online] *Biomimetics*, vol. 3, No. 3, Jul. 23, 2018, pp. 1-12, doi:10.3390/biomimetics3030018.

Criscuolo, E., et al. "Alternative Methods of Vaccine Delivery: An Overview of Edible and Intradermal Vaccines." [online] *Journal of Immunology Research*, vol. 2019, Mar. 4, 2019, doi:10.1155/2019/8303648.

Das, Rakesh, et al. "Biomechanical Evaluation of Wasp and Honeybee Stingers." [online] *Nature: Scientific Reports*, vol. 8, Springer US, Oct. 8, 2018, pp. 1-13, doi:10.1038/s41598-018-33386-y.

Gallagher, A. J., et al. "Dynamic Tensile Properties of Human Skin." [online] *IRCOBI Conference Proceedings—International Research Council on the Biomechanics of Injury* Sep. 2012 Dec. 14, 2012, pp. 494-502. http://www.ircobi.org/wordpress/downloads/irc12/pdf_files/59.pdf (Retrieved May 6, 2021).

Gardeniers, Han J. G. E., et al. "Silicon Micromachined Hollow Microneedles for Transdermal Liquid Transport." [online] *Journal of Microelectromechanical Systems*, vol. 12, No. 6, Dec. 2003, pp. 855-862, doi:10.1109/JMEMS.2003.820293.

Hansen, Kris, et al. *Microneedle Enabled Intradermal Delivery of Biologics*. [Online] 3M Drug Delivery Systems, https://multimedia.3m.com/mws/media/1005621O/microneedle-enabled-intradermal-delivery-of-biologics.pdf (Retrieved Jul. 23, 2021).

Henry, Sebastien, et al. "Microfabricated Microneedles: A Novel Approach to Transdermal Drug Delivery." [online] *Journal of Pharmaceutical Sciences*, vol. 87, No. 8 Aug. 1, 1998, Abstract Only, Doi:10.1021/js980042+.

Hickling, JK, et al. "Intradermal Delivery of Vaccines: Potential Benefits and Current Challenges." [online] Bulletin of the World Health Organization, vol. 89, No. 3, Mar. 2011, pp. 221-226, doi:10.2471/BLT.10.079426.

Hickling, Julian, and Rebecca Jones. *Intradermal Delivery of Vaccines: A Review of the Literature and the Potential for Development for Use in Low- and Middle-Income Countries*. [online] Aug. 27, 2009. https://path.azureedge.net/media/documents/TS_opt_idd_review.pdf.

Hohlfelder, Robert J., et al. "Adhesion of Benzocyclobutene-Passivated Silicon in Epoxy Layered Structures." [online] *Journal of Materials Research*, vol. 16, No. 1, Jan. 2001, pp. 243-255, doi:10.1557/JMR.2001.0037.

Jain, Sunil M., et al. "Evaluation of Skin and Subcutaneous Tissue Thickness at Insulin Injection Sites in Indian, Insulin Naïve, Type-2 Diabetic Adult Population." [online] *Indian Journal of Endocrinology and Metabolism*, vol. 17, No. 5, Sep.-Oct. 2013, p. 864-870, doi:10.4103/2230-8210.117249.

Jarrahian, Courtney, et al. "Clinical Performance and Safety of the ID Adapter, a Prototype Intradermal Delivery Technology for Vaccines, Drugs, and Diagnostic Tests." [online] *Procedia in Vaccinology*, vol. 6, Available online May 2, 2012, pp. 125-133, doi:10.1016/j.provac.2012.04.017.

Jeewandara, Thamarasee. "Glassy Carbon Microneedles: A new transdermal drug delivery device" [online] Phys.org Science News, Jan. 3, 2019, https://phys.org/news/2019-01-glassy-carbon-microneedles-transdermal-drug.html.

Jeong, Hye-Rin et al. "Considerations in the Use of Microneedles: Pain, Convenience, Anxiety, and Safety" [online] *Journal of Drug Targeting*, vol. 25, No. 1, Published Online Jun. 30, 2016. Abstract Only, doi:10.1080/1061186X.2016.1200589.

Khanna, Maneesh et al. "Painless Intradermal Delivery of Insulin: The Novel Clicksoft Microinjection Device" [online] Drug Delivery Technology, vol. 9, No. 2, Feb. 2009, https://pkasofttouch.com/wp-content/uploads/2020/07/AdvancedDelivery-DDT-Feb09-Rd4-Final-web.pdf.

Kim, Y. C., et al. "Delivery Systems for Intradermal Vaccination." [online] *Current Topics in Microbiology and Immunology*, vol. 351, Apr. 7, 2011, pp. 77-112, doi:https://doi.org/10.1007/82_2011_123.

Kram, Tim, et al. *High Barrier Multilayer Blow-Fill-Seal Containers : A Comparison of Four Different Analytical Methods for Oxygen Permeation*. [online] Rommelag, https://www.pharmaceuticalonline.com/doc/high-barrier-multilayer-blow-fill-seal-containers-a-comparison-of-four-different-analytical-methods-for-oxygen-permeation-0001 (Retrieved May 6, 2021).

Larrañeta, Eneko, et al. "Microneedle Arrays as Transdermal and Intradermal Drug Delivery Systems: Materials Science, Manufacture and Commercial Development." [online] *Materials Science*

(56) References Cited

OTHER PUBLICATIONS

*and Engineering R: Reports*, vol. 104, Available online Apr. 13, 2016, pp. 1-32, doi:10.1016/j.mser.2016.03.001.

Lee, Jeong Woo, and Mark R. Prausnitz. "Drug Delivery Using Microneedle Patches: Not Just for Skin." [online] *Expert Opinion on Drug Delivery*, vol. 15, No. 6, Taylor & Francis, May 7, 2018, pp. 541-543, doi:10.1080/17425247.2018.1471059.

Levin, Yotam, et al. "Intradermal Vaccination Using the Novel Microneedle Device MicronJet600: Past, Present, and Future." [online] *Human Vaccines and Immunotherapeutics*, vol. 11, No. 4, Published online May 1, 2015, pp. 991-997, doi:10.1080/21645515.2015.1010871.

Li, Yan, et al. "Fabrication of Sharp Silicon Hollow Microneedles by Deep-Reactive Ion Etching towards Minimally Invasive Diagnostics." [online] *Microsystems and Nanoengineering*, vol. 5, Aug. 26, 2019, pp. 1-11, doi:10.1038/s41378-019-0077-y.

Maiti, Raman, et al. "In Vivo Measurement of Skin Surface Strain and Sub-Surface Layer Deformation Induced by Natural Tissue Stretching." [online] *Journal of the Mechanical Behavior of Biomedical Materials*, vol. 62, Available online Jun. 5, 2016, pp. 556-569, doi:10.1016/j.jmbbm.2016.05.035.

Markarian, Jennifer. "Manufacturing Microneedle Array Patches for Vaccine Delivery." [online] *Pharmaceutical Technology*, vol. 44, No. 5, May 2, 2020, pp. 31-32.

Norman, James J., et al. "Reliability and Accuracy of Intradermal Injection by Mantoux Technique, Hypodermic Needle Adapter, and Hollow Microneedle in Pigs." [online] *Drug Delivery and Translational Research*, vol. 4, No. 2, Published Online Nov. 18, 2013, pp. 126-130, doi:10.1007/s13346-013-0184-5.

Oltulu, Pembe, et al. "Measurement of Epidermis, Dermis, and Total Skin Thicknesses from Six Different Body Regions with a New Ethical Histometric Technique." [online] *Turkish Journal of Plastic Surgery*, vol. 26, No. 2, Web Publication Apr. 13, 2018, pp. 56-61, doi:10.4103/tjps.tjps_2_17.

Pastore, Michael N., et al. "Transdermal Patches: History, Development and Pharmacology." [online] *British Journal of Pharmacology*, vol. 172, No. 9, Jan. 5, 2015, pp. 2179-2209, doi:10.1111/bph.13059.

Patel, Dipen, et al. "Transdermal Drug Delivery System: A Review." [online] *The Pharma Innovation Journal*, vol. 1, No. 4, Jun. 2012, pp. 66-75, https://www.thepharmajournal.com/vol1Issue4/Issue_june_2012/14.pdf.

Prausnitz, Mark R., and Robert Langer. "Transdermal Drug Delivery (Author Manuscript)" [online] Nature Biotechnology, Available in PubMed Central Jun. 23, 2009, https://www.ncbi.nlm.nih.gov/pmc/articles/PMC2700785/pdf/nihms121685.pdf.

Rodgers, Aoife M., et al. "Dissolving Microneedles for Intradermal Vaccination: Manufacture, Formulation, and Stakeholder Considerations." [online] *Expert Opinion on Drug Delivery*, vol. 15, No. 11, Taylor & Francis, Published online Sep. 19, 2018, pp. 1039-1043, doi:10.1080/17425247.2018.1522301.

Roxhed, Niclas. "A Fully Integrated Microneedle-Based Transdermal Drug Delivery System." [online] *Submitted to the School of Electrical Engineering KTH—Royal Institute of Technology*, Available from Sep. 10, 2007, http://www.diva-portal.org/smash/get/diva2:12495/FULLTEXT01.pdf.

Samel, Bjoern. "Novel Microfluidic Devices Based on a Thermally Responsive PDMS Composite." [online] *Submitted to the School of Electrical Engineering KTH—Royal Institute of Technology*, Available from Aug. 21, 2007, https://www.diva-portal.org/smash/get/diva2:12419/FULLTEXT01.pdf.

Shrestha, Pranav, and Boris Stoeber. "Fluid Absorption by Skin Tissue during Intradermal Injections through Hollow Microneedles." [online] *Nature: Scientific Reports*, vol. 8, Springer US, Sep. 13, 2018, pp. 1-13, doi:10.1038/s41598-018-32026-9.

Tsals, Izrail. "Usability Evaluation of Intradermal Adapters (IDA)." [Article in Press online] *Vaccine*, 2016, http://dx.doi.org/10.1016/j.vaccine.2016.07.036.

Tsals, Izrail, et al. "Clinical Performance and Safety of Adapters for Intradermal Delivery with Conventional and Autodisable Syringes." [Article in Press online] *Vaccine*, 2015, http://dx.doi.org/10.1016/j.vaccine.2015.04.095.

Vosseler, Michael, et al. "A Smart Interface for Reliable Intradermal Injection and Infusion of High and Low Viscosity Solutions." [online] *Pharmaceutical Research*, vol. 28, No. 3, Nov. 23, 2010, pp. 647-661, doi:10.1007/s11095-010-0319-z.

Waghule, Tejashree, et al. "Microneedles: A Smart Approach and Increasing Potential for Transdermal Drug Delivery System." [online] *Biomedicine and Pharmacotherapy*, vol. 109. Available online Nov. 9, 2018, Elsevier, 2019, pp. 1249-1258, doi:10.1016/j.biopha.2018.10.078.

Weatherford, Greg "Once a coronavirus vaccine exists, a VCU researcher's mailable patch could deliver it to millions" [online] Virginia Commonwealth University News, May 13, 2020. https://news.vcu.edu/article/Once_a_coronavirus_vaccine_exists_a_VCU_researchers_mailable.

Yadav, Prateek Ranjan, et al. "Mathematical Modelling, Simulation and Optimisation of Microneedles for Transdermal Drug Delivery: Trends and Progress." [online] *Pharmaceutics*, vol. 12, No. 8, Jul. 22, 2020, pp. 1-31, doi:10.3390/pharmaceutics12080693.

Yang, Jian, et al. "Recent Advances of Microneedles for Biomedical Applications: Drug Delivery and Beyond." [online] *Acta Pharmaceutica Sinica B*, vol. 9, No. 3, Elsevier Ltd, Available online Apr. 4, 2019, pp. 469-483, doi:10.1016/j.apsb.2019.03.007.

International Search Report and Written Opinion dated Jun. 24, 2022 received in International patent application PCT/US2021/065820 from European Patent Office as International Searching Authority, European Patent Office, P.B. 5818 Patentlaan 2 NL—2280 HV Rijswijk (16pgs).

\* cited by examiner

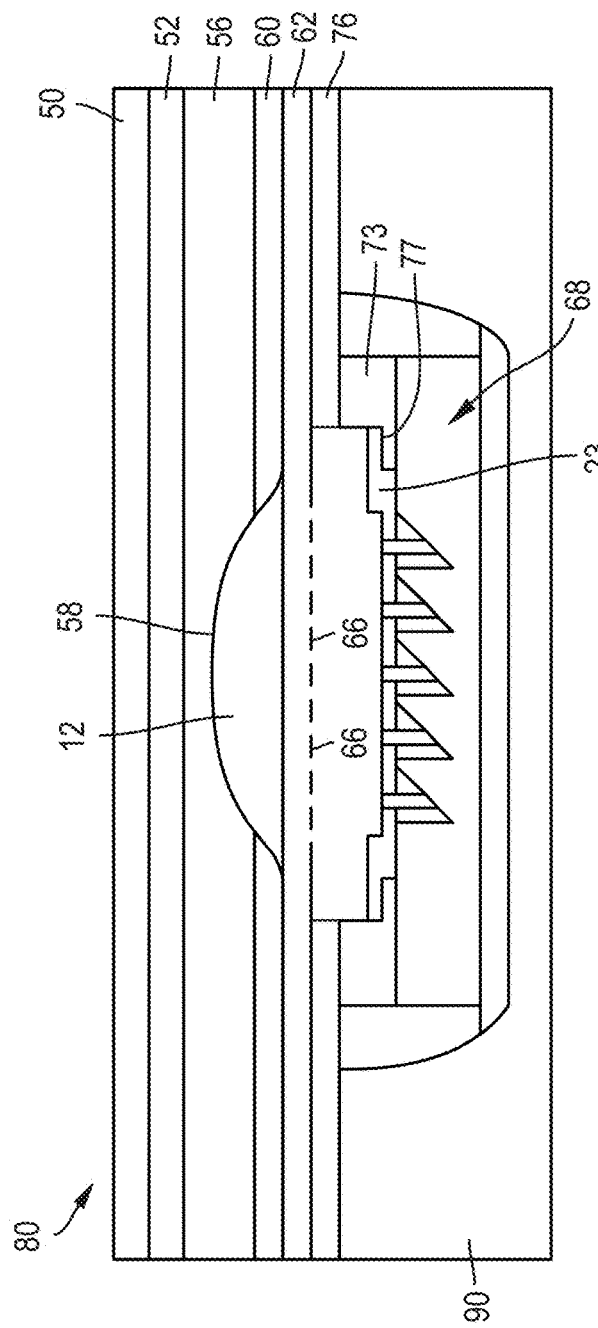
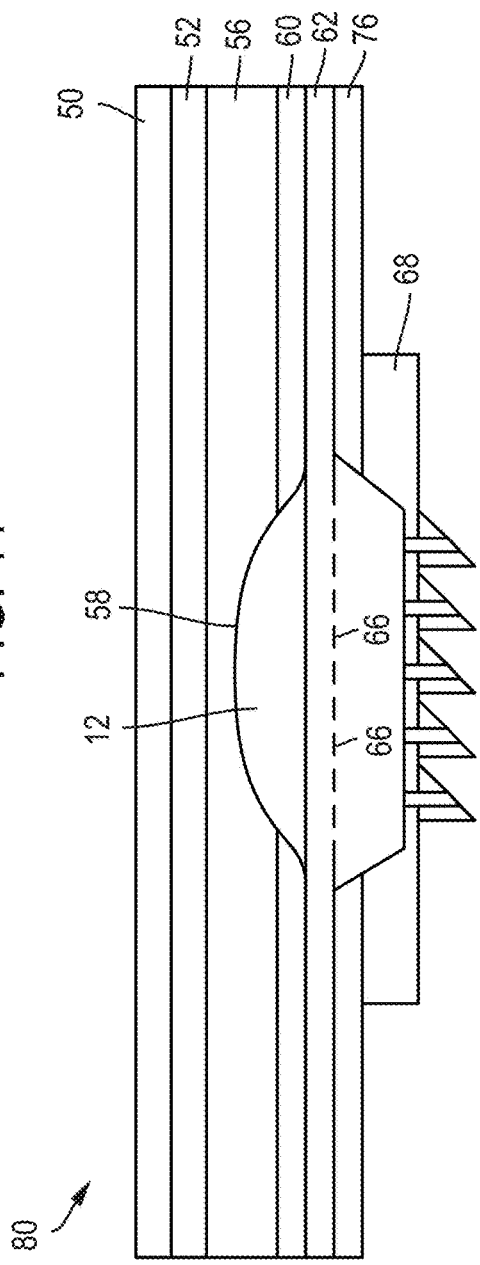
FIG. 11
FIG. 12

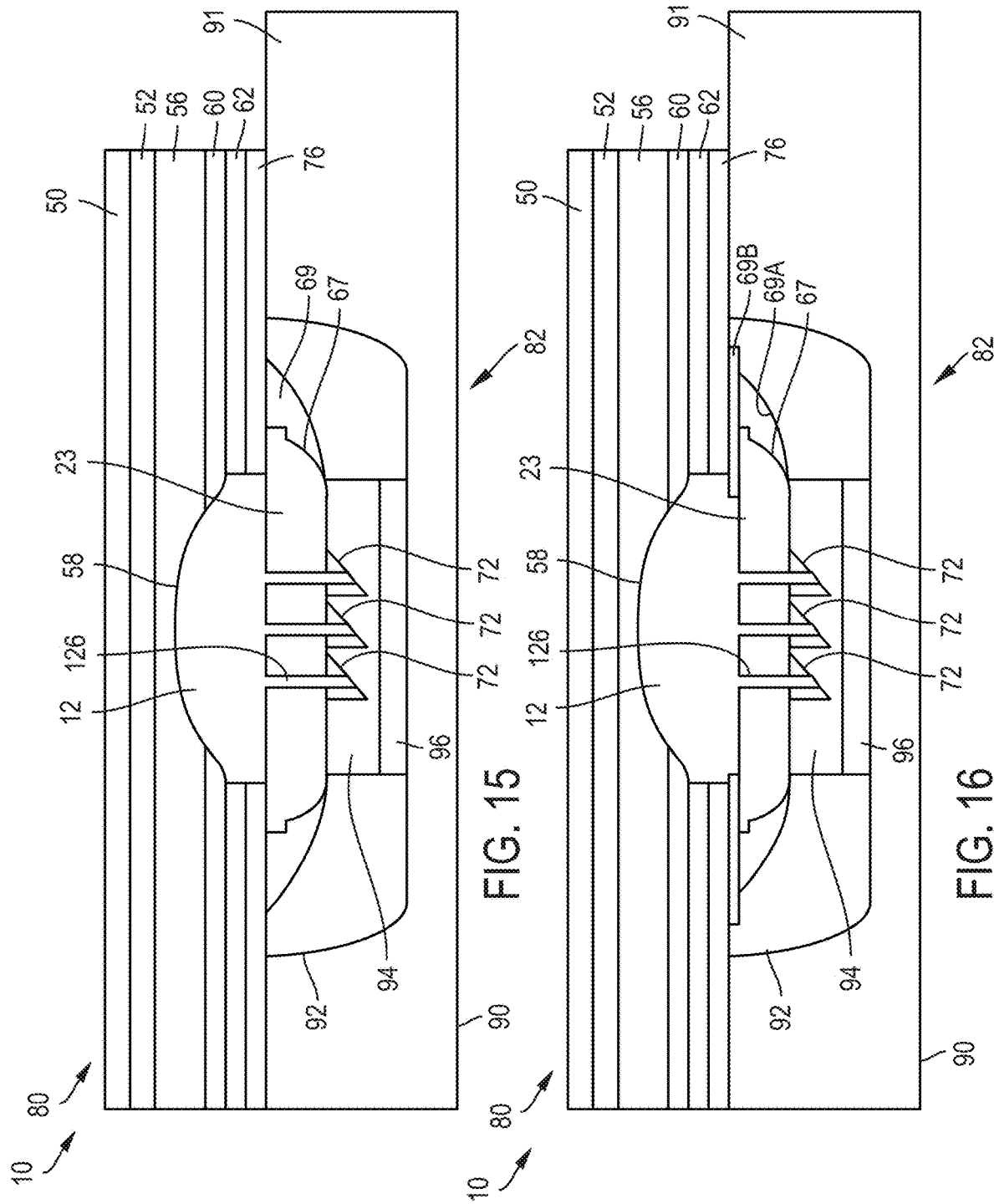

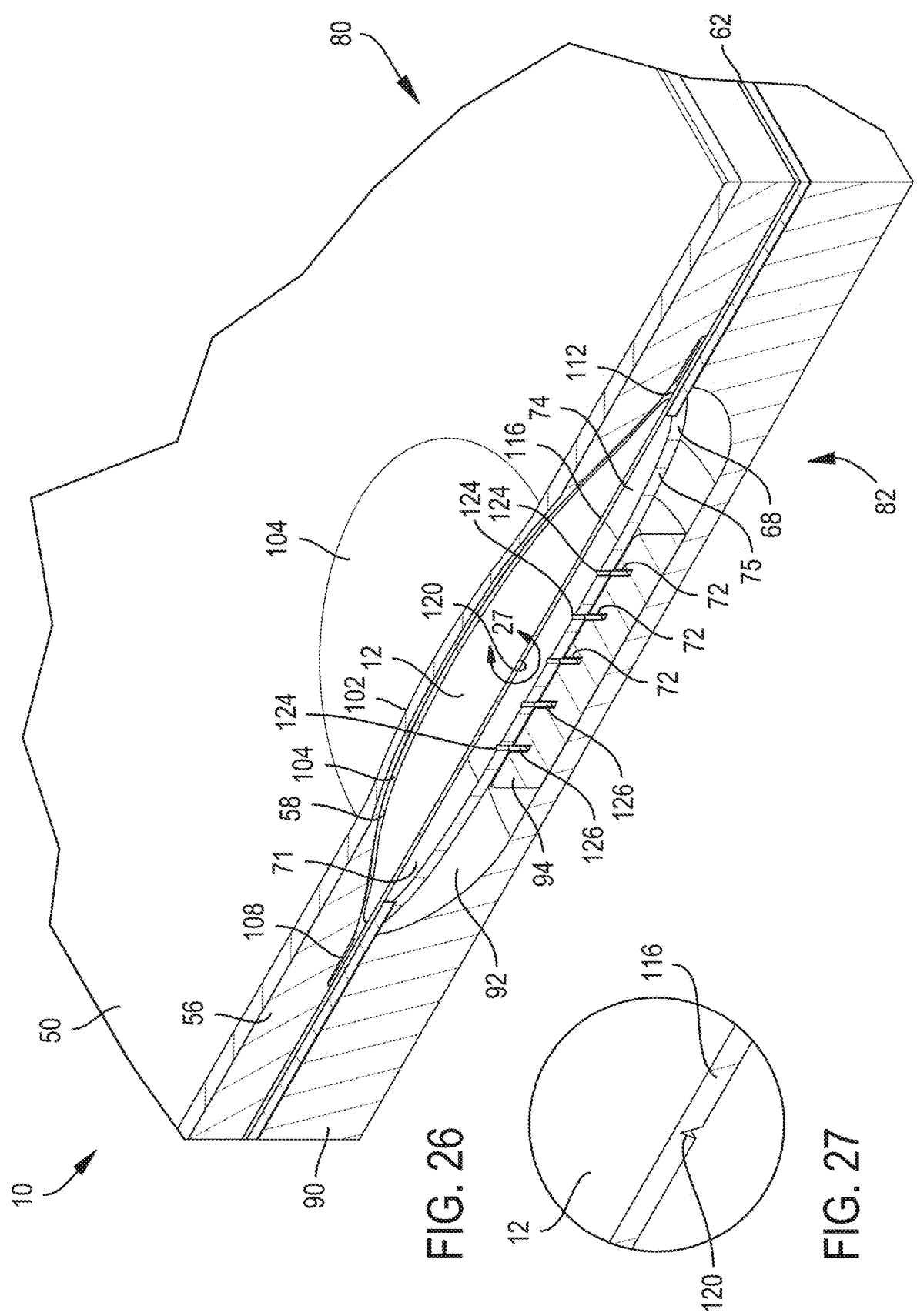

MEDICAL AGENT DISPENSING SYSTEMS, METHODS, AND APPARATUSES

STATEMENT REGARDING FEDERALLY SPONSORED RESEARCH OR DEVELOPMENT

This invention was made with Government support under Agreement W911NF-17-3-0003, awarded by ACC-APG-RTP. The Government has certain rights in the invention.

CROSS-REFERENCE TO RELATED APPLICATIONS

NONE

BACKGROUND

Field of Disclosure

This disclosure relates to medical agent delivery. More specifically, this disclosure relates to dispensers for therapeutic and other medical agents.

Description of Related Art

Novel pathogens present a variety of public health challenges which are not simple to quickly overcome. From the medical perspective, existing preventive medicine infrastructure has not been and is not well suited to novel pathogens such as SARS, MERS, Zika, and COVID-19. Other pathogens for which herd immunity does not exist (e.g. Ebola), or highly dangerous pathogens which mutate quickly may present similar challenges. Vaccines typically take years to create and once a vaccine does exist, the prospect of rapidly generating billions of doses would almost certainly exceed current vaccine production capabilities. Without vaccination, other preventative measures such as, testing, contact tracing, and personal protective equipment (PPE) are of elevated importance. Again, however, these preventative measures can only provide as much benefit as relevant supply chains allow. Shortages of PPE and testing kits have plagued medical systems in the United States and elsewhere across the globe as they struggle to address the COVID-19 pandemic. In turn, this has hampered the potential to perform effective contact tracing which is already a vast undertaking due to the scale of the COVID-19 pandemic. Additionally, novel pathogens may refocus medical systems away from their typical functions. Secondary impacts often result when the medical community's attention is demanded by a widespread pandemic. This can take the form of delayed surgeries, elective procedures, routine doctor's office visits, etc., but secondary impacts can also be much worse. As has been pointed out by the Chief of Immunizations at UNICEF, for example, during efforts to control an Ebola outbreak in the Democratic Republic of the Congo in 2019 the number of deaths due to measles was double the death toll from Ebola.

Novel pathogens also present challenges that are more psychological in nature. Put simply, such pathogens scare people. Without readily available PPE and testing, people may elect to avoid visiting medical facilities or clinics for fear of exposure to disease. Even with readily available PPE, certain individuals, such as populations in high risk demographics for a particular pathogen, may still have misgivings about visiting such facilities. Additionally, as has been the case in the United States, some may fiercely object to usage of PPE for various reasons. This presents a further public health challenge to systems attempting to deal with pandemics. Solutions to novel pathogens should seek to address and work around these challenges in order to be effective.

SUMMARY

In accordance with an embodiment of the present disclosure, a medical agent delivery device may comprise an agent filled collapsible reservoir. The device may further comprise a base portion including at least one microneedle on a first face of the base portion and at least one microneedle on an opposing second face of the base portion. Each of the at least one microneedle on the first face may be in fluid communication with a microneedle of the at least one microneedle on the second face. The device may further comprise an elastomeric housing attached to the first face of the base portion. The reservoir and the at least one microneedle on the first side of the base portion may be within the elastomeric housing. The device may further comprise a displaceable spacer. The displaceable space may have a first position in which the spacer supports the reservoir in spaced relation to the at least one microneedle on the first side of the base portion and a second position. When the spacer is in the second position the elastomeric housing may be configured to press the reservoir into the at least one microneedle on the first side of the base portion.

In some embodiments, the reservoir may be filled with a vaccine. In some embodiments, the at least one microneedle on the first side of the base portion may be one of: a one dimensional array of microneedles and a two dimensional array of microneedles. In some embodiments, the base portion may be a single monolithic contiguous structure. In some embodiments, the base portion may be at least partially constructed of silicon. In some embodiments, a section of the base portion including the at least one microneedle on the first side of the base portion and the at least one microneedle on the second side of the base portion may be formed of a monolithic piece of material. In some embodiments, surfaces of the reservoir defining an interior volume of the reservoir may be formed of SiOx. In some embodiments, the reservoir may be constructed partially of metal foil. In some embodiments, the reservoir may be filled with a vaccine selected from a group consisting of a whole virus vaccine, an attenuated virus vaccine, an inactivated virus vaccine, a nucleic acid based vaccine, a RNA based vaccine, an mRNA vaccine, a DNA based vaccine, a plasmid based vaccine, a viral vector vaccine, a non-replicating viral vector vaccine, a replicating viral vector vaccine, a peptide based vaccine, a subunit vaccine, a nanoparticle vaccine, a recombinant vaccine, a conjugate vaccine, a dendritic cell vaccine, a monovalent vaccine, a polyvalent vaccine, and a virus like particle vaccine. In some embodiments, the reservoir may be filled with a SARS-COV-2 vaccine selected from a group consisting of a whole virus vaccine, an attenuated virus vaccine, an inactivated virus vaccine, a nucleic acid based vaccine, a RNA based vaccine, an mRNA vaccine, a viral vector vaccine, a non-replicating viral vector vaccine, a peptide based vaccine, and a subunit vaccine.

In accordance with another embodiment of the present disclosure a medical agent delivery device may comprise an agent filled collapsible reservoir. The device may further comprise a base portion including at least one reservoir rupture element on a first face of the base portion and at least one microneedle on an opposing second face of the base portion. Each of the at least one reservoir rupture element may be in fluid communication with a microneedle of the at least one microneedle on the second face. The device may further comprise a housing sheet including an elastic material attached to the first face of the base portion. The reservoir and the at least one reservoir rupture element may be disposed within an interior of the device defined by the base portion and housing sheet. The device may further comprise a displaceable spacer having a first position in which the spacer supports the reservoir in spaced relation to the at least one reservoir rupture element and a second position in which the reservoir is free to displace into contact with the at least one reservoir rupture element. The housing sheet may be configured to be in a stretched state when the spacer is in the first position and configured contract and displace the reservoir into the at least one reservoir rupture element when the spacer is displaced to the second position.

In some embodiments, the reservoir may be filled with a vaccine. In some embodiments, the at least one reservoir rupture element may be one of: a one dimensional array of reservoir rupture elements and a two dimensional array of reservoir rupture elements. In some embodiments, each of the at least one reservoir rupture elements may be microneedles. In some embodiments, the base portion may include a skin compatible adhesive on an exterior face thereof. In some embodiments, the base portion may be constructed at least partially of silicon. In some embodiments, a section of the base portion including the at least reservoir rupture element and the at least one microneedle may be formed of a monolithic piece of material. In some embodiments, the reservoir may be constructed at least partially of a material which has properties which render the material inhospitable to microbial growth. In some embodiments, the reservoir may be constructed at least partially of metal foil. In some embodiments, the reservoir may be filled with a vaccine selected from a group consisting of a whole virus vaccine, an attenuated virus vaccine, an inactivated virus vaccine, a nucleic acid based vaccine, a RNA based vaccine, an mRNA vaccine, a DNA based vaccine, a plasmid based vaccine, a viral vector vaccine, a non-replicating viral vector vaccine, a replicating viral vector vaccine, a peptide based vaccine, a subunit vaccine, a nanoparticle vaccine, a recombinant vaccine, a conjugate vaccine, a dendritic cell vaccine, a monovalent vaccine, a polyvalent vaccine, and a virus like particle vaccine. In some embodiments, the reservoir may be filled with a SARS-COV-2 vaccine selected from a group consisting of a whole virus vaccine, an attenuated virus vaccine, an inactivated virus vaccine, a nucleic acid based vaccine, a RNA based vaccine, an mRNA vaccine, a viral vector vaccine, a non-replicating viral vector vaccine, a peptide based vaccine, and a subunit vaccine.

In accordance with another embodiment of the present disclosure a medical agent delivery device may comprise a base portion including a skin compatible adhesive and a receptacle. The device may further comprise a housing sheet including an elastic material attached to the base portion and together with the base portion may define an interior volume of the device. The device may further comprise a collapsible reservoir between the base portion and housing sheet. The collapsible reservoir may have a filled state in which the reservoir is filled with a first volume of a medical agent and a depleted state in which the reservoir is at least partly collapsed and filled with a second volume of the medical agent less than the first volume. The device may further comprise a sharp bearing body disposed in the receptacle and including at least one microneedle on a first side thereof. Each of the at least one microneedle may be associated with a lumen extending from an associated microneedle on a second opposing side of the sharp bearing body and through the sharp bearing body. The housing sheet may be configured to be in a stretched state when the reservoir is in the filled state and configured urge the reservoir to the depleted state as the housing sheet restores to a less stretched state.

In some embodiments, the delivery device may further comprise strap having at least one wrapping indicator thereon. In some embodiments, the indicator may include an indicium thereon. In some embodiments, the strap may be constructed at least partially of an elastomeric material. In some embodiments, the strap may be constructed of a self-adhering bandage material. In some embodiments, a spacer element may be disposed in the interior volume of the device between the collapsible reservoir and the housing sheet. In some embodiments, the sharp bearing body may be constructed at least partially of silicon. In some embodiments, the medical agent may be a vaccine. In some embodiments, an innermost surface of the reservoir may be SiOx and the reservoir may include at least one layer of metal film. In some embodiments, the reservoir may be filled with a vaccine selected from a group consisting of a whole virus vaccine, an attenuated virus vaccine, an inactivated virus vaccine, a nucleic acid based vaccine, a RNA based vaccine, an mRNA vaccine, a DNA based vaccine, a plasmid based vaccine, a viral vector vaccine, a non-replicating viral vector vaccine, a replicating viral vector vaccine, a peptide based vaccine, a subunit vaccine, a nanoparticle vaccine, a recombinant vaccine, a conjugate vaccine, a dendritic cell vaccine, a monovalent vaccine, a polyvalent vaccine, and a virus like particle vaccine. In some embodiments, the reservoir may be filled with a SARS-COV-2 vaccine selected from a group consisting of a whole virus vaccine, an attenuated virus vaccine, an inactivated virus vaccine, a nucleic acid based vaccine, a RNA based vaccine, an mRNA vaccine, a viral vector vaccine, a non-replicating viral vector vaccine, a peptide based vaccine, and a subunit vaccine.

In accordance with an embodiment of the present disclosure a delivery device may comprise a base portion having an adhesive bearing face. The device may further comprise a collapsible reservoir. The device may further comprise at least one delivery sharp. The device may further comprise a bimetallic actuator positioned in line with the reservoir. The device may further comprise at least one heat directing member. The at least one heat directing member may include a portion disposed in the plane of the base portion. The heat directing member may be configured to conduct heat from a surface to which the delivery device is applied to the bimetallic actuator.

In some embodiments, the at least one delivery sharp may include a microneedle. In some embodiments, the at least one delivery sharp may be one of a one dimensional and two dimensional array of microneedles. In some embodiments, the at least one heat directing member may be formed as a wing which extends from a side of the bimetallic actuator. In some embodiments, the bimetallic actuator may include a first metal portion and a second metal portion. The wing may be an extension of one of the first and second metal portion. In some embodiments, the delivery device may include two heat directing members formed as wings which extend from opposing sides of the bimetallic actuator. In some embodiments, the bimetallic actuator may be configured to bend from an inactive state to an active state. The bimetallic actuator may be configured to be in the inactive state when subjected to cold chain storage temperatures. In some embodiments, the portion of the at least one heat directing member disposed in the plane of the base portion may include an adhesive bearing face. In some embodiments, the at least one heat directing member may be metallic. In some embodiments, the collapsible reservoir may include a wall portion having at least one metallic layer. In some embodiments, the collapsible reservoir may be filled with a vaccine when in a filled state. In some embodiments, the reservoir may be filled with a vaccine selected from a group consisting of a whole virus vaccine, an attenuated virus vaccine, an inactivated virus vaccine, a nucleic acid based vaccine, a RNA based vaccine, an mRNA vaccine, a DNA based vaccine, a plasmid based vaccine, a viral vector vaccine, a non-replicating viral vector vaccine, a replicating viral vector vaccine, a peptide based vaccine, a subunit vaccine, a nanoparticle vaccine, a recombinant vaccine, a conjugate vaccine, a dendritic cell vaccine, a monovalent vaccine, a polyvalent vaccine, and a virus like particle vaccine. In some embodiments, the reservoir may be filled with a SARS-COV-2 vaccine selected from a group consisting of a whole virus vaccine, an attenuated virus vaccine, an inactivated virus vaccine, a nucleic acid based vaccine, a RNA based vaccine, an mRNA vaccine, a viral vector vaccine, a non-replicating viral vector vaccine, a peptide based vaccine, and a subunit vaccine.

In accordance with an embodiment of the present disclosure, a delivery device may comprise a base portion having an adhesive bearing face. The device may further comprise a collapsible reservoir. The device may further comprise at least one delivery sharp. The device may further comprise a force generating element in line with the reservoir and having an inactive state in which no force is generated by the force generating element and an active state in which the force generating element applies a force to the reservoir. The force generating member may be configured to automatically transition from the inactive state to the active state when the force generating element is subjected to a temperature condition.

In some embodiments, the at least one delivery sharp may include a microneedle. In some embodiments, the at least one delivery sharp may be one of a one dimensional and two dimensional array of microneedles. In some embodiments, the delivery device may further comprise at least one heat directing member including a portion disposed in the plane of the base portion. In some embodiments, the at least one heat directing member may be continuous with a portion of the force generating element. In some embodiments, the at least one heat directing member may be metallic. In some embodiments, the portion of the at least one heat directing member disposed in the plane of the base portion may include an adhesive bearing face. In some embodiments, the delivery device may include two heat directing members formed as wings which extend from opposing sides of the force generating element. In some embodiments, the temperature condition may be a change in temperature from a cold chain storage temperature to a warmer temperature. In some embodiments, the force generating element may be configured to transition from the inactive state to the active state by bending. In some embodiments, the collapsible reservoir may include a wall portion having at least one metallic layer. In some embodiments, the collapsible reservoir may be filled with a vaccine. In some embodiments, the reservoir may be filled with a vaccine selected from a group consisting of a whole virus vaccine, an attenuated virus vaccine, an inactivated virus vaccine, a nucleic acid based vaccine, a RNA based vaccine, an mRNA vaccine, a DNA based vaccine, a plasmid based vaccine, a viral vector vaccine, a non-replicating viral vector vaccine, a replicating viral vector vaccine, a peptide based vaccine, a subunit vaccine, a nanoparticle vaccine, a recombinant vaccine, a conjugate vaccine, a dendritic cell vaccine, a monovalent vaccine, a polyvalent vaccine, and a virus like particle vaccine. In some embodiments, the reservoir may be filled with a SARS-COV-2 vaccine selected from a group consisting of a whole virus vaccine, an attenuated virus vaccine, an inactivated virus vaccine, a nucleic acid based vaccine, a RNA based vaccine, an mRNA vaccine, a viral vector vaccine, a non-replicating viral vector vaccine, a peptide based vaccine, and a subunit vaccine.

In accordance with another embodiment of the present disclosure a medical agent delivery device may comprise a base portion having an adhesive bearing face. The device may further comprise a collapsible reservoir. The device may further comprise at least one delivery sharp. The device may further comprise a strip including a bimetallic region in line with the reservoir. The bimetallic region may have an inactive state and an active state in which the bimetallic region applies a force to the reservoir. The bimetallic region may be configured to automatically transition from the inactive state to the active state when the force generating element is subjected to a change from a colder temperature to a warmer temperature.

In some embodiments, the at least one delivery sharp may include a microneedle. In some embodiments, the at least one delivery sharp may be one of a one dimensional and two dimensional array of microneedles. In some embodiments, the delivery device may include a cover over the strip and the base portion. The cover may be a sheet of adhesive bearing material. In some embodiments, the strip includes at least one heat collector region in line with a plane of the base portion. In some embodiments, the at least one heat collector region and a portion of the bimetallic region are formed out of a single continuous piece of material. In some embodiments, the strip includes two wings which extend from opposing sides of the bimetallic region. In some embodiments, the bimetallic region may be configured to bend from the inactive state to the active state and be configured to be in the inactive state when subjected to cold chain storage temperatures. In some embodiments, the strip may be entirely constructed of metallic material. In some embodiments, the at least one delivery sharp may be may be included on a sharp bearing body formed of silicon. In some embodiments, the collapsible reservoir may include an opening in a wall of the collapsible reservoir. The sharp bearing body may be coupled to the collapsible reservoir and forming a fluid tight seal around the opening. In some embodiments, the collapsible reservoir may be filled with a vaccine. In some embodiments, the reservoir may be filled with a vaccine selected from a group consisting of a whole virus vaccine, an attenuated virus vaccine, an inactivated virus vaccine, a nucleic acid based vaccine, a RNA based vaccine, an mRNA vaccine, a DNA based vaccine, a plasmid based vaccine, a viral vector vaccine, a non-replicating viral vector vaccine, a replicating viral vector vaccine, a peptide based vaccine, a subunit vaccine, a nanoparticle vaccine, a recombinant vaccine, a conjugate vaccine, a dendritic cell vaccine, a monovalent vaccine, a polyvalent vaccine, and a virus like particle vaccine. In some embodiments, the reservoir may be filled with a SARS-COV-2 vaccine selected from a group consisting of a whole virus vaccine, an attenuated virus vaccine, an inactivated virus vaccine, a nucleic acid based vaccine, a RNA based vaccine, an mRNA vaccine, a viral vector vaccine, a non-replicating viral vector vaccine, a peptide based vaccine, and a subunit vaccine.

BRIEF DESCRIPTION OF THE DRAWINGS

These and other aspects will become more apparent from the following detailed description of the various embodiments of the present disclosure with reference to the drawings wherein:

FIG. 11 depicts an embodiment of another example delivery device;

FIG. 12 depicts a view of the delivery device embodiment of FIG. 10 with a cover assembly of the delivery device removed;

FIG. 15 depicts another embodiment of an example delivery device;

FIG. 16 depicts an embodiment of yet another example delivery device;

FIG. 26 depicts a cross sectional view taken at the indicated cut plane in FIG. 22;

FIG. 27 depicts a detailed view of the indicated region of FIG. 26;

DETAILED DESCRIPTION

Figure 1:
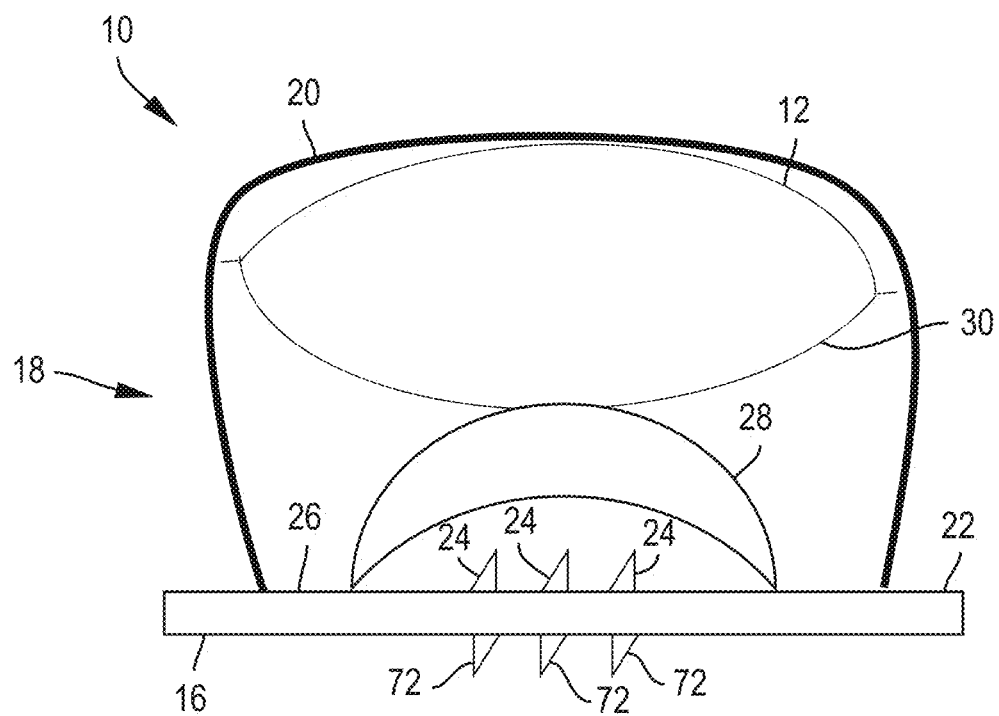
FIG. 1 depicts an embodiment of an exemplary delivery device.

FIG. 1 depicts an embodiment of an exemplary delivery device 10. The example delivery device 10 may be a low profile, patch type delivery device 10 which may be applied over the skin of a patient. The example delivery device 10 may be sized for handheld use and may be easily applied to a wide variety of injection sites over a patient's body. Additionally, the example delivery device 10 may be designed for use by a patient or relatively untrained or minimally trained individual. Thus a medical caregiver may not be necessary for use of the delivery device 10.

Such delivery devices 10 may be used to dispense a medical agent from a reservoir 12 included within the delivery device 10 into a target delivery destination of a patient via one or more delivery sharp 72. The reservoir 12 may be at least partly flexible and may have a variable volume which may deplete as fluid is dispensed from the reservoir 12. As the reservoir 12 depletes, the reservoir 12 may at least partially collapse. In the example embodiment, a plurality of delivery sharps 72 are included in the delivery device 10, though other embodiments may only include a single delivery sharp 72. The plurality exemplary of delivery sharps 72 may be arranged in a one or two dimensional array and may extend from and proud of a skin facing surface 16 of the delivery device 10. Where multiple delivery sharps 72 are included, the delivery sharps 72 may be arranged in one or more rows and/or columns. Though three delivery sharps 72 arranged in a single row are depicted in FIG. 1, the number and arrangement of delivery sharps 72 may differ in alternative embodiments. Any suitable number of rows and/or columns may be included in various examples. In various embodiments there may, for example, be a single row array of delivery sharps 72 including up to five delivery sharps 72. Preferably, the delivery sharps 72 may be arranged so as to prevent a bed of nails type scenario in which penetration of the skin via the delivery sharps 72 may be inhibited or inconsistent across users or delivery devices 10. This may occur when too many delivery sharps 72 are arranged in close proximity to one another. Thus, the array may be referred to as a spaced array of delivery sharps 72.

The delivery sharps 72 may be selected based on the desired target delivery destination in a patient. In certain embodiments, the target delivery destination may be a transcutaneous location. For example, the target delivery destination may be a subcutaneous delivery destination or an intramuscular delivery destination. Alternatively, the target delivery destination may be a shallow delivery destination between the stratum corneum of a patient and the subcutaneous tissue of the patient. Such shallow destinations may be referred to herein as intradermal delivery destinations. Shallow delivery destinations may include an epidermal or dermal target location or may, for example, target a junctional area between the epidermis and dermis or dermis and subcutis. In the example embodiment, the delivery sharps 72 are depicted as microneedles. Such delivery sharps 72 may be present in delivery devices 10 with shallow (e.g. above subcutaneous tissue) target delivery destinations. In alternative embodiments where, for instance, the target delivery destination is a subcutaneous or intramuscular location, conventional delivery sharps (e.g. 30-gauge needle) may be utilized.

Figure 2:
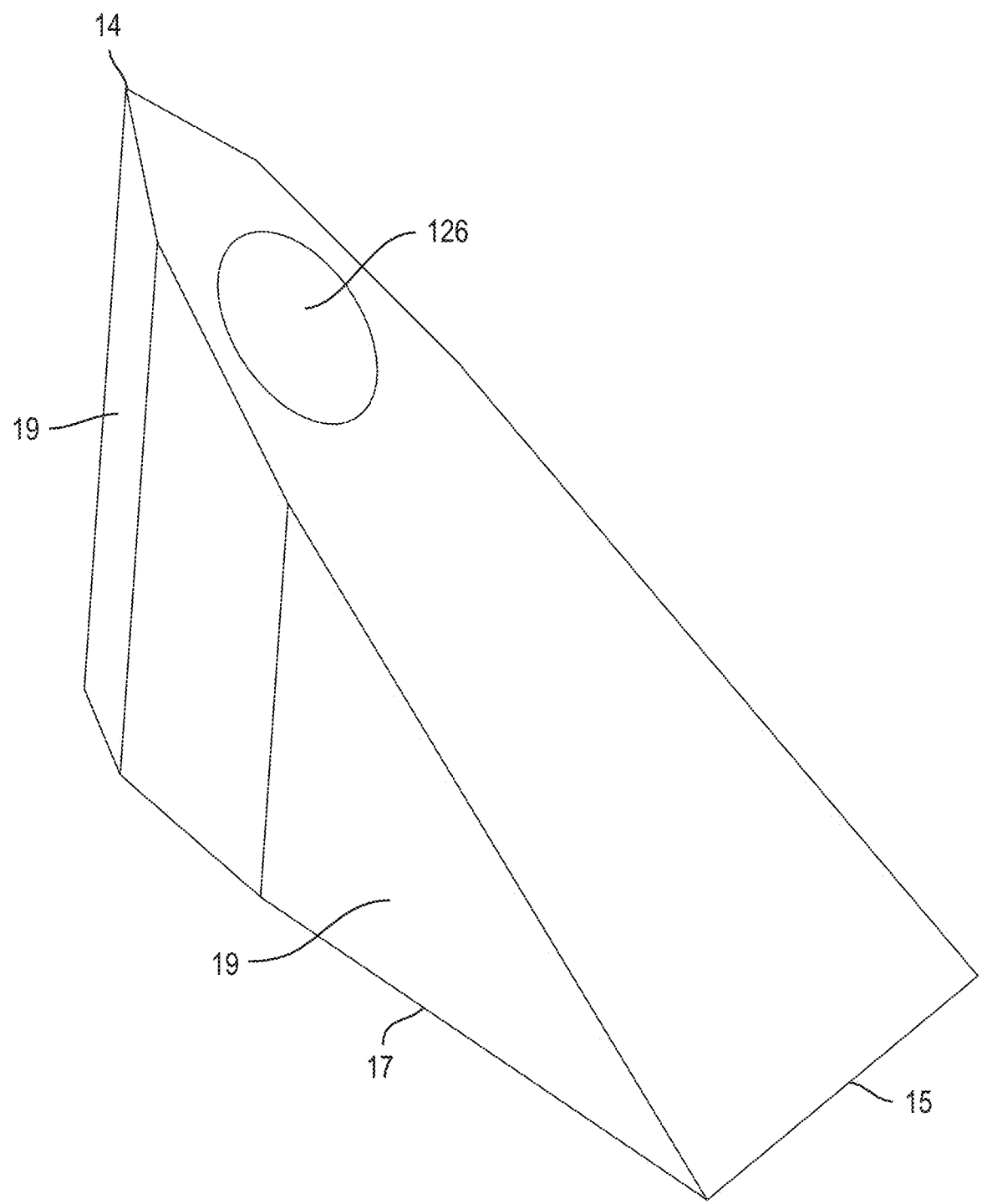
FIG. 2 depicts an example embodiment of a delivery sharp.

Referring now also to FIG. 2, where microneedles are used, the microneedles described herein may, in certain embodiments, be MEMS produced, polyhedral (e.g. pyramidal), silicon crystal microneedles. These microneedles may be no greater than 1 mm in height, e.g. 0.6 mm (though longer microneedles may also be used). At least some edges of the microneedles may be rounded or filleted, though such microneedles may still be considered polyhedral. In some examples and as shown in FIG. 2, the microneedles described herein may be generally in the shape of a heptagonal prism (though pentagonal, nonagonal, and other polygonal. prisms may also be used as the base shape) which has been diagonally sected to form a heptagonal ramp or pointed wedge. In such embodiments, the heptagonal prism may be sected by a plane extending from a vertex 14 of the top face of the prism through the most distal side 15 of the base 17. At least two sides of the base of the microneedle may be parallel. The side walls 19 may extend substantially perpendicularly from the base 17. The microneedle may be substantially symmetric about a line of symmetry extending from the vertex 14 to a point above the center of the most distal side 15. In other embodiments, the microneedles may be conically shaped. Any other suitable shape may be used.

The points or tips of microneedles described herein may be solid and the flow lumens 126 through the microneedles may be offset from the points or tips (in FIG. 2 the vertex 14 forms the tip) of the microneedles. Hollow tipped microneedles in which the flow lumen 126 extends to the tip of the microneedle may also be utilized. In some embodiments, the microneedles may be NanoPass hollow microneedles available from NanoPass Technologies Ltd. of 3 Golda Meir, Nes Ziona, Israel. It should be noted that microneedles (or the substrate on which they are disposed) described herein as constructed of silicon may have a surface layer of silicon dioxide (which may, for example, form with exposure to air) while still being considered constructed of silicon.

In other embodiments, microneedles described herein may be constructed of glass (e.g. silica glass, borosilicate glass), ceramic (e.g. alumina, calcium sulfate dehydrate, calcium phosphate dehydrate, organically modified ceramics such as Ormocer), polymer, carbohydrate, or metal (e.g. stainless steel, titanium, palladium, nickel, alloys such as palladium cobalt alloys, etc.). Any suitable microneedle constructions including dissolvable microneedles may be used. Microneedles may be manufactured in one or more of, though are not limited to, a molding process, etching process, ablative process (e.g. laser ablation), or a material additive process (e.g. 3D printed). In various embodiments, it may be desirable that microneedles be constructed of a biocompatible, non-ductile, high Young's modulus material with an indentation hardness sufficient to allow penetration into skin without breakage.

Referring again primarily to FIG. 1, delivery devices 10 described herein may deliver any of a variety of medications or other medical agents to a patient. In certain embodiments, a delivery device 10 may include a reservoir 12 filled with a vaccine. Such a delivery device 10 may deliver any suitable vaccine, though may be particularly well suited to vaccines for novel pathogens (e.g. SARS-CoV-2) or for pathogens where herd immunity does not exist (e.g. Ebola). Additionally, such delivery devices 10 may be of particular usefulness in outbreaks of pathogens (such as measles for example) in communities which choose to forego typical vaccinations. For example, such delivery devices 10 could be distributed without requiring patients to congregate in hospitals or other shared spaces. This would mitigate concern for pathogen transmission related to vaccination programs and alleviate potential worries that could dissuade people from reporting to receive a vaccination. Instead, delivery devices 10 could be picked up and used by patients without breach of social distancing, gathering size recommendations, or other safety guidelines. Alternatively, such delivery devices 10 could be distributed directly to patients without requiring a patient to leave their domicile or requiring distribution personnel to interact with individuals who decline to utilize recommended PPE. Delivery devices 10 could be filled with a vaccine for a novel pathogen or could perhaps be filled with vaccines typical of a normal vaccination schedule. In the latter case, such a delivery device 10 could help to ensure that disruption of vaccination for known pathogens does not occur during a novel pathogen pandemic.

Any suitable vaccine may be delivered via such a delivery device 10. For example, the vaccine may be but is not limited to, attenuated live vaccines, inactivated virus vaccines, acellular vaccines, cellular vaccines, toxoid vaccines, heterotypic or Jennerian vaccines, monovalent vaccines, polyvalent vaccines, nucleic acid vaccines (e.g. DNA, plasmid vaccine, mRNA), virus like particle vaccines, recombinant vector vaccines (e.g. replicating, non-replicating), dendritic cell vaccines, T-cell receptor peptide vaccines, chimeric vaccines, subunit vaccines, nanoparticle vaccines, recombinant protein vaccines, polysaccharide vaccines, and conjugate vaccines. It should be noted that these are not necessarily mutually exclusive. For instance, a vaccine could be a recombinant protein nanoparticle vaccine or some other combination of the above. Vaccine may also refer to a combination vaccine (e.g. DTaP, MMR, MMRV, etc.) or a vaccination agent which targets a single pathogen or multiple strains of a single pathogen. Example vaccines may include, but are not limited to vaccines for various coronaviruses such as SARS-COV, SARS-COV-2, MERS-COV, HCoV-NL63, HCoV-229E, HCoV-OC43 and HKU1. Delivery devices 10 described herein are also not limited for use with humans. Such delivery devices 10 may be used for livestock, pets, services animals, or in other veterinary applications. In such cases, these delivery devices 10 may be filled with a vaccine for at least one non-human pathogen. Delivery devices 10 described herein may also be useful for research applications.

Where a delivery device 10 is filled with a vaccine, it may be desirable that the target delivery destination be a shallow delivery destination. This may be particularly desirable where the amount of available vaccine is limited. For example, such a delivery device 10 may be well suited for use with new vaccines having high demand. Vaccines for novel pathogens (e.g. SARS-CoV-2 or other coronaviruses) may, for instance, be well suited for use with delivery devices 10 described herein.

Evidence suggests that shallow delivery of vaccines may provoke protective immune response with smaller amounts of vaccine antigen. As a result, dose sparing may be practiced allowing the same quantity of vaccine to be effective for immunizing a greater number of people. Alternatively or additionally, injection sparing may be possible. Shallow administration with a delivery device 10 such as those shown herein may allow for a single injection protocol where other routes of administration may require multiple injections over some period of time. One or more adjuvants may be included in some vaccine formulations to further aid in facilitating dose or injection sparing.

Particularly for new vaccines generated to combat an ongoing pandemic (e.g. a vaccine for SARS-CoV-2), the prospect of rapidly generating billions of doses would almost certainly exceed current vaccine production capabilities. Due to the injection and dose sparing potential of delivery devices 10 described herein, such delivery devices 10 may facilitate vaccination of large numbers of people even when a critically needed vaccine is in short supply. Additionally, as a consequence of potential dose and injection sparing, delivery devices 10 such as those shown and described herein may allow injections to be more cost effective. Moreover, due to the small volume of vaccine needed, delivery devices 10 may be made relatively small. This may simplify shipping and help to facilitate rapid distribution of vaccine to a population. This may be particularly attractive for vaccines which require cold chain distribution as packing volume may be of heightened importance.

Additionally, some studies have suggested that shallow administration may be particularly helpful in certain patient populations. For example, elderly populations may receive superior protection from vaccinations received intradermally than via other routes. That said, the Mantoux technique, which is typically used for intradermal administration, can pose reliability concerns and can be difficult to perform, especially without training. Per the World Health Organization, a large factor which has limited the use of intradermal vaccination has been the lack of a delivery platform.

Delivery devices 10, such as those shown and described herein, may provide an attractive delivery platform for intradermal vaccination. Consequentially, delivery devices 10 described and shown herein may help to give better protection to vulnerable populations and may help in meeting the large demand for vaccines against, for example, novel pathogens by leveraging dose/injection sparing possible with intradermal vaccination. Moreover, intradermal delivery devices 10 described herein may be painless or nearly pain free which may make the delivery devices 10 described herein user preferable over other types of injections. That said, and as mentioned above, delivery devices 10 described herein are not limited to delivery via the intradermal route. Delivery devices 10 may, for instance, be configured as transdermal (e.g. subcutaneous or intramuscular) delivery devices 10.

The example delivery devices 10 shown herein additionally are not limited to vaccine delivery devices. Such a delivery device 10 may fill a number of niches in the medical field. Other agents, for example, diagnostic or testing agents may be supplied via certain example delivery devices 10. For instance, allergens or potential allergens may be administered via the delivery device 10. Tuberculosis testing agents may be delivered via the delivery device 10. Such delivery devices 10 may also be used to deliver medication for endocrine disorders. For instance, insulin may be delivered with some exemplary delivery devices 10.

Still referring to FIG. 1, the reservoir 12 of the example delivery device 10 may be surrounded by a housing 18. The housing 18 may include a base portion 22 which may be adjacent the skin when the delivery device 10 is applied to a user. The base portion 22 may include a skin facing surface 16 which may at least partially be covered with an adhesive. The base portion 22 may be substantially flat and generally rigid though in some examples, the base portion 22 may be at least somewhat flexible so as to allow the base portion 22 to adapt to body contours of certain injection sites. The housing 18 may also include an elastomeric sheet 20 which may be formed at least partially of an elastic material. The elastomeric sheet 20 may be coupled to the base portion 22 in any suitable manner. The reservoir 12 may be disposed between the elastomeric sheet 20 and the base portion 22. The elastomeric wall 20 and the base portion 22 may enshroud the reservoir 12 and render the reservoir 12 inaccessible by a user from the exterior of the delivery device 10. When the reservoir 12 is in a filled state, the elastomeric sheet 20 may be in a stretched state. Restoring force exerted by the stretched elastomeric sheet 20 may press against the reservoir 12. This restoring force may urge the reservoir 12 to collapse as well as urge fluid contained in the reservoir 12 to be forced out of the reservoir 12 once fluid communication between the reservoir 12 and the at least one delivery sharp 72 has been established. Thus, the elastomeric sheet 20 may double as a bias member or biasing sheet which may drive fluid out of the reservoir 12 during use.

As shown, the delivery device 10 may include one or more reservoir rupture element(s) 24. The reservoir rupture element(s) 24 may be blade like or sharp projections in various embodiments. In the example embodiment shown in FIG. 1, a set of three reservoir rupture elements 24 are depicted. Any suitable number of reservoir rupture elements 24 may be used. The reservoir rupture elements 24 may be arranged in a one or two dimensional array with any desired number of rows and/or columns. In certain embodiments, for each delivery sharp 72 included in the delivery device 10, a corresponding reservoir rupture element 24 may extend from a reservoir facing surface 26 of the base portion 22. Such reservoir rupture elements 24 may be arranged in opposition with and substantially along the same axis as their corresponding delivery sharp 72. Additionally, reservoir rupture elements 24 may include a flow lumen extending therethrough. These flow lumens may fluidically communicate with a delivery lumen in a respective delivery sharp 72. Such fluid communication may be established via flow lumens which may extend directly to the delivery lumen of the respective delivery sharps 72. In the example embodiment, the reservoir rupture elements 24 are shown as microneedles. Thus the example delivery device 10 may include a set of microneedles extending into the interior of the housing 18 and a set of microneedles extending from the exterior of the housing 18. The base portion 22 or at least the section of the base portion 22 including the delivery sharp(s) 72 and reservoir rupture element(s) 24 may be formed of a single monolithic piece of material. This component may be referred to herein as a fluid delivering portion of the delivery device 10. In some embodiments, the base portion 22 or at least the section of the base portion 22 including the delivery sharp(s) 72 and reservoir rupture element(s) 24 may be constructed of a single piece of etched silicon.

Still referring to FIG. 1, the example delivery device 10 may also include a spacer element 28. The spacer element 28 may be disposed intermediate the reservoir 12 and the reservoir rupture elements 24. When in a storage state, the spacer element 28 may inhibit the reservoir 12 from contacting the reservoir rupture element(s) 24. In certain embodiments, the spacer element 28 may be a bridge type element which extends over the reservoir rupture element(s) 24 and supports the reservoir 12 thereon. The spacer element 28 may be displaceable within the housing 18. When the delivery device 10 is in a storage state, the spacer element 28 may be in a reservoir protecting position. In this position, the spacer element 28 may inhibit contact between the reservoir 12 and the reservoir rupture element(s) 24. The spacer element 28 may, for instance, present a physical barrier which blocks the reservoir rupture element(s) 24 from contacting the reservoir 12.

The spacer element 28 may be displaced to an activation position when the delivery device 10 is readied for use (e.g. applied to an injection site). This may remove a mechanical interference which blocked the reservoir 12 from contacting the reservoir rupture element(s) 24. With the spacer element 28 in the activation position, the reservoir 12, or at least a portion of the reservoir 12, may be pressed via the elastomeric sheet 20 into contact with the reservoir rupture element(s) 24. Thus, the elastomeric sheet 20 may act as a bias member which may displace the reservoir 12 from its storage position into the reservoir rupture element(s) 24. The reservoir rupture element(s) 24 may puncture through the material forming the reservoir wall 30 and a flow path may be established between the interior volume of the reservoir 12 and the target delivery destination in the patient via the delivery sharps 72. Thus, the delivery device 10 may be in an inactive or storage state until a user interaction with the delivery device 10 transitions the delivery device 10 into an active state. The reservoir 12 may be out of communication with the delivery sharp(s) 72 until this user interaction occurs.

As the elastomeric sheet 20 continues to restore toward a resting position, the reservoir 12 may be urged to a collapsed state and its contents may be expelled through the delivery sharps 72 into the patient. The resting state of the elastomeric sheet 20 may generally correspond to an empty state of the reservoir 12 in which the elastomeric sheet 20 has substantially entirely collapsed the reservoir 12. In some embodiments, the elastomeric sheet 20 may still be slightly stretched in the resting state.

In alternative examples, the elastomeric sheet 20 need not act as a bias member. For example, in certain embodiments, the elastomeric sheet 20 may be replaced by a flaccid wall. A user may press against a portion of the flaccid wall when the spacer element 28 is brought to an activation position. This may displace the reservoir 12 into the reservoir rupture element(s) 24. Likewise, pressure may be manually applied by a user to collapse the reservoir 12 and urge fluid into the patient via the delivery sharps 72.

Figure 3:
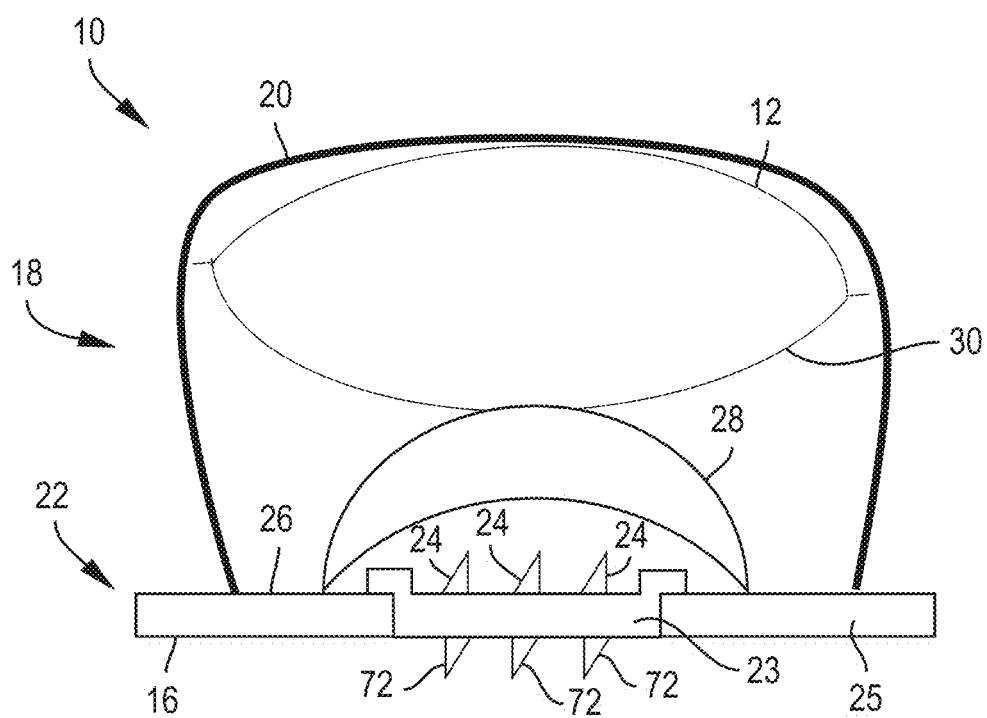
FIG. 3 depicts another example embodiment of a delivery device.

Referring now to FIG. 3, in certain examples, the base portion 22 may be an assembly. The base portion 22 may include a base member 25 and a sharp bearing body 23. The sharp bearing body 23 may be coupled into an aperture included in the base body 25 and may include the delivery sharps 72 and the reservoir rupture elements 24. Thus, the sharp bearing body 23 may be relatively small in comparison to the entire base portion 22. Where the delivery sharps 72 and reservoir rupture elements 24 are formed via an etching process for instance, this may aid in increasing the number of delivery devices 10 which may be constructed from a single wafer of material.

Figure 4:
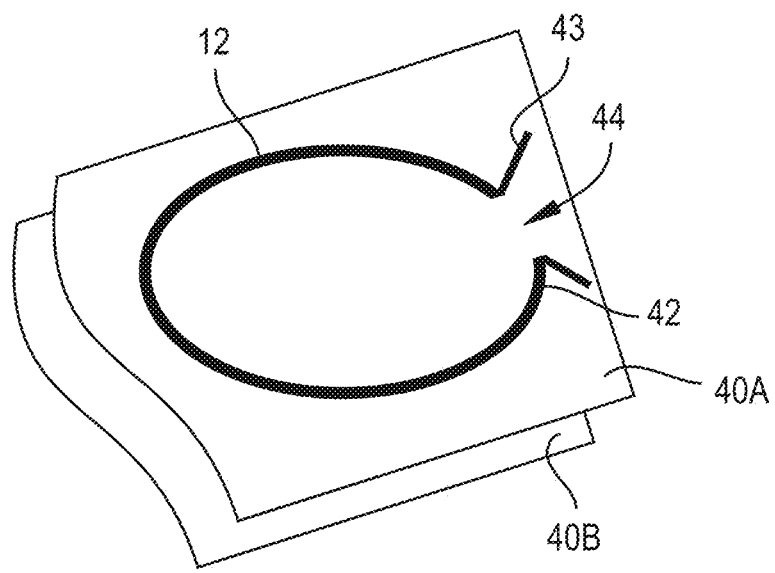
FIG. 4 depicts a diagrammatic view of an example reservoir in a partially formed and unfilled state.

Referring now to FIG. 4, an example reservoir 12 is shown prior to filling and sealing of the reservoir 12. The reservoir 12 may be constructed of a first portion and a second portion which are joined together in fluid tight manner so as to form an interior volume therebetween. After filling, the reservoir 12 may be assembled into a delivery device 10.

As shown, the reservoir 12 may be constructed of a first sheet 40A and a second sheet 40B of material which may be flexible. The first sheet 40A and second sheet 40B may be the same materials or dissimilar materials depending on the embodiment. The material(s) forming each sheet 40A, B may be selected so as to be compatible with the desired contents of the reservoir 12. The sheets 40A, B may have a thickness sufficient to allow reservoir rupture element(s) 24 to puncture the reservoir 12. Additionally, where the reservoir 12 is to be punctured by reservoir rupture elements 24, the sheets 40A, B may have a hardness which does not interfere with puncture via the reservoir rupture element(s) 24. Preferably, the thickness of the sheets 40A, B and the elastomeric sheet 20 together may be sufficient to inhibit puncture of a reservoir rupture element 24 to the exterior of the delivery device 10.

The first sheet 40A and second sheet 40B may each be laminates of a number of materials. For example, the first sheet 40A and second sheet 40B may include a layer directly adjacent the interior volume (innermost layer) which may be an agent compatible layer which may have low extractable/leachable content. In certain examples, the innermost layer may be formed of an inert material. In some embodiments, this layer may be a thin layer of Silicon oxide ($SiO_x$). Such a layer of $SiO_x$ may be provided on a polyethylene terephthalate (PET) film or polypropylene film in some embodiments.

The first and second sheet 40A, B may also include one or more barrier layer. The barrier layer(s) may, for example, be moisture, vapor, and/or gas barrier layer(s). The barrier layer(s) may include a metallic layer. In certain embodiments, a copper or titanium layer may be used. Copper may be particularly desirable due to its elastic properties. Non-metallic barrier materials may also be used. $SiO_x$ for example may be used as a barrier material.

The first and second sheet 40A, B may include at least one antimicrobial layer. Such a layer may double as a barrier layer. In certain examples, an antimicrobial layer may be a metal or metal alloy which creates an inhospitable environment for microbes. In some instances, the antimicrobial layer may be a metal or metal alloy possessing cidal properties with respect to microbes. For example, an antimicrobial layer may be a transition metal or transition metal alloy such as any cidal transition metal or alloy thereof from the d-block (including e.g. V, Ti, Cr, Co, Ni, Cu, Zn, Tb, W, Ag, Cd, Au, Hg). Other metals and metalloids with cidal properties (e.g. Al, Ga, Ge, As, Se, Sn, Sb, Te, Pb and Bi) or their alloys, may also be used. The material used for the antimicrobial layer may be dependent upon the intended use (e.g. research, vaccination, veterinary, etc.) of the delivery device 10. An antimicrobial layer may for example be constructed of copper, copper alloy, silver, or silver alloy in certain examples. Where a metal or alloy layer is included, the metal or alloy layer may be an external or outermost layer of the first and second sheet 40A, B.

Other layers may include strengthening layers, tie layers, light blocking layers, or bonding compatible layers which may facilitate coupling of the first and second sheets 40A, B to one another or to other materials. In some embodiments, multiple layers which serve the same purpose or multiple layers made from the same material may be included. For example, there may be multiple barrier layers. In certain examples, the first or second sheet 40A, B may include a layer of polyester, polyimide, polypropylene, or a fluoropolymer film such as a polychlorotrifluoroethylene or chlorotrifluoroethylene (e.g. Aclar). In certain embodiments, the first and second sheets 40A, B may be constructed at least partially of super barrier films. For example, a film including alternating layers of SiOx and acrylic may be used.

The first and second sheet 40A, B may be coupled to one another with a weld 42. The weld 42 may be created in any suitable manner, for example, via laser welding or a sonic welding operation such as an ultrasonic welding operation. The weld 42 may be formed in a controlled environment. Any suitable cleanroom environment may, for example be employed. The weld 42 may define a partially enclosed space between the first and second sheets 40A, B. The weld 42 may be formed so as to leave an access gap 44 to an otherwise sealed interior volume created between the first and second sheet 40A, B. In some embodiments, a neck portion 43 which flanks the access gap 44 may also be formed as part of weld 42.

A filling implement may be brought into fluid communication with the interior volume via the access gap 44. In embodiments including a neck portion 43, the filling implement may seal against a narrow section of the neck portion 43 and be blocked via this narrow section from entering the area circumscribed by the weld 42. Thus, a neck portion 43 may inhibit a tip of a filling implement from potentially contacting walls that will define the interior volume of the reservoir 12 when the reservoir 12 is completed. The interior volume of the reservoir 12 may then be filled. In certain examples, the interior volume may be filled with a plurality of fluids. For example, the interior volume may be filled with an inert gas such as nitrogen and a vaccine or other medical agent. The gas may serve to open the interior volume of the reservoir 12 and separate the first and second sheet 40A, B at the reservoir portion of the sheets 40A, B. As agent (e.g. vaccine) is subsequently dispensed into the reservoir 12, the gas may be replaced with the agent leaving a substantially agent filled reservoir 12 devoid of other fluids.

Figure 5:
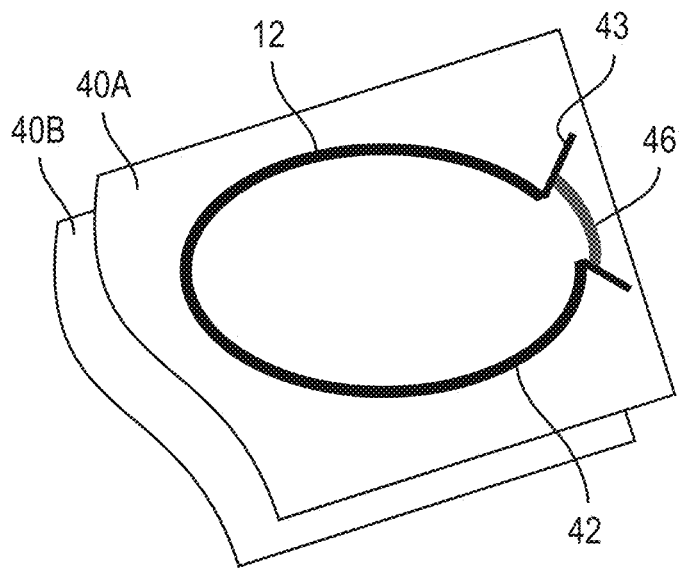
FIG. 5 depicts a diagrammatic view of an example filled and sealed reservoir.

Referring now to FIG. 5, after filling, the access gap 44 may be closed by a second weld 46. In some examples the second weld 46 may be formed in a region of the neck portion 43 to close off flow through the access gap 44. The second weld 46 may be any suitable type of weld. The second weld 46 may be the same type of weld as the first weld 42. In certain examples, the second weld 46 may be a sonic weld such as an ultrasonic weld. Once the second weld 46 is completed, the interior volume of the reservoir 12 may be sealed from the surrounding environment. Excess portions of sheets 40A, B may be removed in some embodiments if present.

Figure 6:
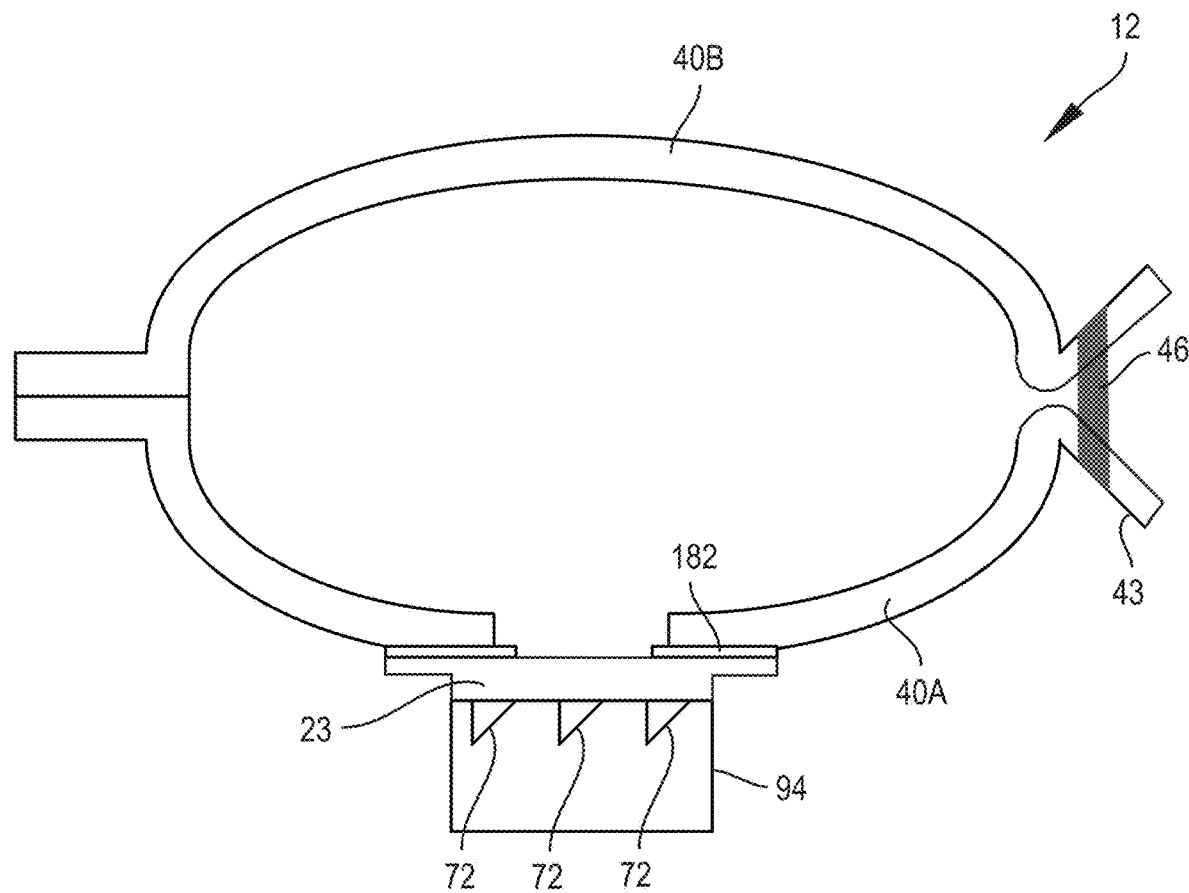
FIG. 6 depicts a diagrammatic view of another example reservoir.

Referring now to FIG. 6, another exemplary reservoir 12 which may be assembled into a delivery device 10 is depicted. The reservoir 12 may be constructed of a welded first sheet 40A and second sheet 40B of material as described above. Any sheet 40A, B material or multi-layer material arrangement such as any of those described above in relation to FIGS. 4-5 may be used. The reservoir 12 may be filled through a neck portion 43 of the reservoir 12 and then sealed via a second weld 46. The reservoir 12 may also include at least one delivery sharp 72. In the example embodiment, the reservoir 12 includes a one dimensional array of three delivery sharps 72. In alternative embodiments any suitable number of delivery sharps 72 may be included in any number of rows and/or columns. The delivery sharp(s) 72 may be included on a sharp bearing body 23. The sharp bearing body 23 may be constructed of etched silicon in certain embodiments and the delivery sharp(s) 72 may be microneedles. The sharp bearing body 23 may be a monolithic component.

As shown in the exemplary FIG. 6, where a reservoir 12 includes a sharp bearing body 23, the sharp bearing body 23 may be coupled to a sheet 40A (though in some embodiments the sheet may be sheet 40B) of the reservoir 12 via adhesive 182. A portion of the sheet 40A over the delivery sharp(s) 72 within the footprint of the sharp bearing body 23 may be removed so as to establish fluid communication from the interior volume of the reservoir 12 to the delivery sharp(s) 72. For example, a patch of material may be laser cut out of the sheet 40A. Alternatively and as mentioned in relation to FIG. 15, a portion of the sheet 40A over a portion of the sharp bearing body 23 may be scored so as to be rupturable under pressure. As shown in FIG. 6, a removable delivery sharp cover 94 may be placed over the delivery sharp(s) 72. The delivery sharp cover 94 may block flow out of the interior volume of the reservoir 12 via the delivery sharp(s) 72 and seal the reservoir 12 from the surrounding environment. The delivery sharp cover 94 may, for example, be spin coated over and encase the delivery sharp(s) 72 as described in greater detail later in the specification.

Figure 7:
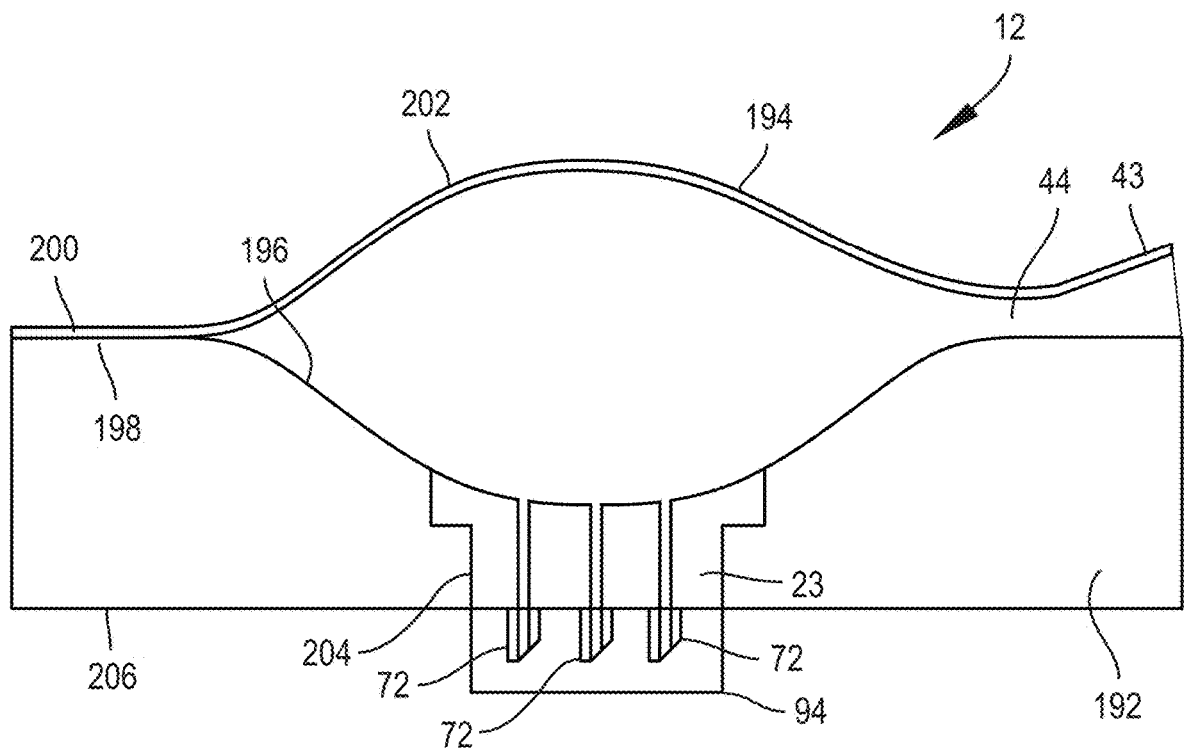
FIG. 7 depicts a diagrammatic view of another example reservoir.
Figure 8:
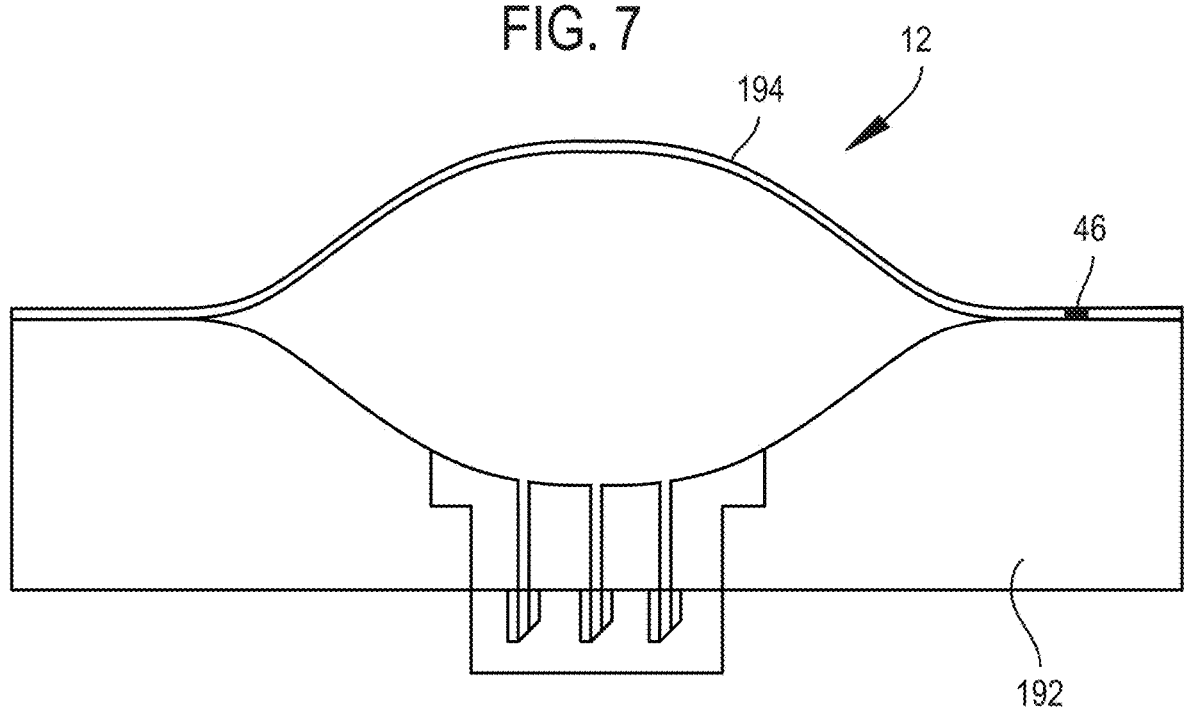
FIG. 8 depicts a diagrammatic view of another example reservoir.

Referring now to FIGS. 7-8, another exemplary embodiment of a reservoir 12 is depicted. The reservoir 12 in FIGS. 7-8 includes a first portion which is flexible and a second portion which is rigid or substantially rigid. As shown, the reservoir 12 may be constructed of a rigid body 192 and a sheet 194 of flexible material. The sheet 194 may, for example, be constructed of any material described above in relation to sheets 40A, B or a combination of these materials (e.g. may be a multi-layer film). The sheet 194 may extend over a depression 196 (though the depression may be omitted in some embodiments) which is recessed into a face of the rigid body 192. The sheet 194 may be coupled in fluid tight manner (e.g. ultrasonically welded) to the rigid body 192. In the example embodiment, the sheet 194 includes a central raised (e.g. domed) region 202 and a peripheral flange 200. The central raised region 202 may be pre-formed (e.g. thermoformed) into the sheet 194. The peripheral flange 200 may be coupled to a periphery of the rigid body 192. In the example, the peripheral flange 200 is coupled to a rim 198 of the rigid body 192 which surrounds the depression 196. The sheet 194 may be coupled to the rim 198 so as to form an access gap 44 and a neck portion 43. The reservoir 12 may be filled with fluid and a second weld 46 may be formed so as to close the neck portion 43 and access gap 44 as shown in FIG. 8.

The rigid body 192 may include a receptacle 204 which may extend from a portion of the depression 196 through the rigid body 192 to an opposing face 206 of the rigid body 192. The receptacle 204 may be centrally disposed in the rigid body 192. A sharp bearing body 23 may be seated and retained within the receptacle 204. Thus the reservoir 12 may include at least one delivery sharp 72. The sharp bearing body 23 may be a monolithic part and may be constructed of etched silicon in certain embodiments. The delivery sharps 72 may be microneedles. In the example embodiment, the sharp bearing body 23 and the receptacle 204 have cooperating stepped sidewalls which may help to ensure that the sharp bearing body 23 is not removed from the rigid body 192. The delivery sharps 72 of the sharp bearing body 23 may be covered with a delivery sharp cover 94. Any delivery sharp cover 94 described herein may be used.

Figure 9:
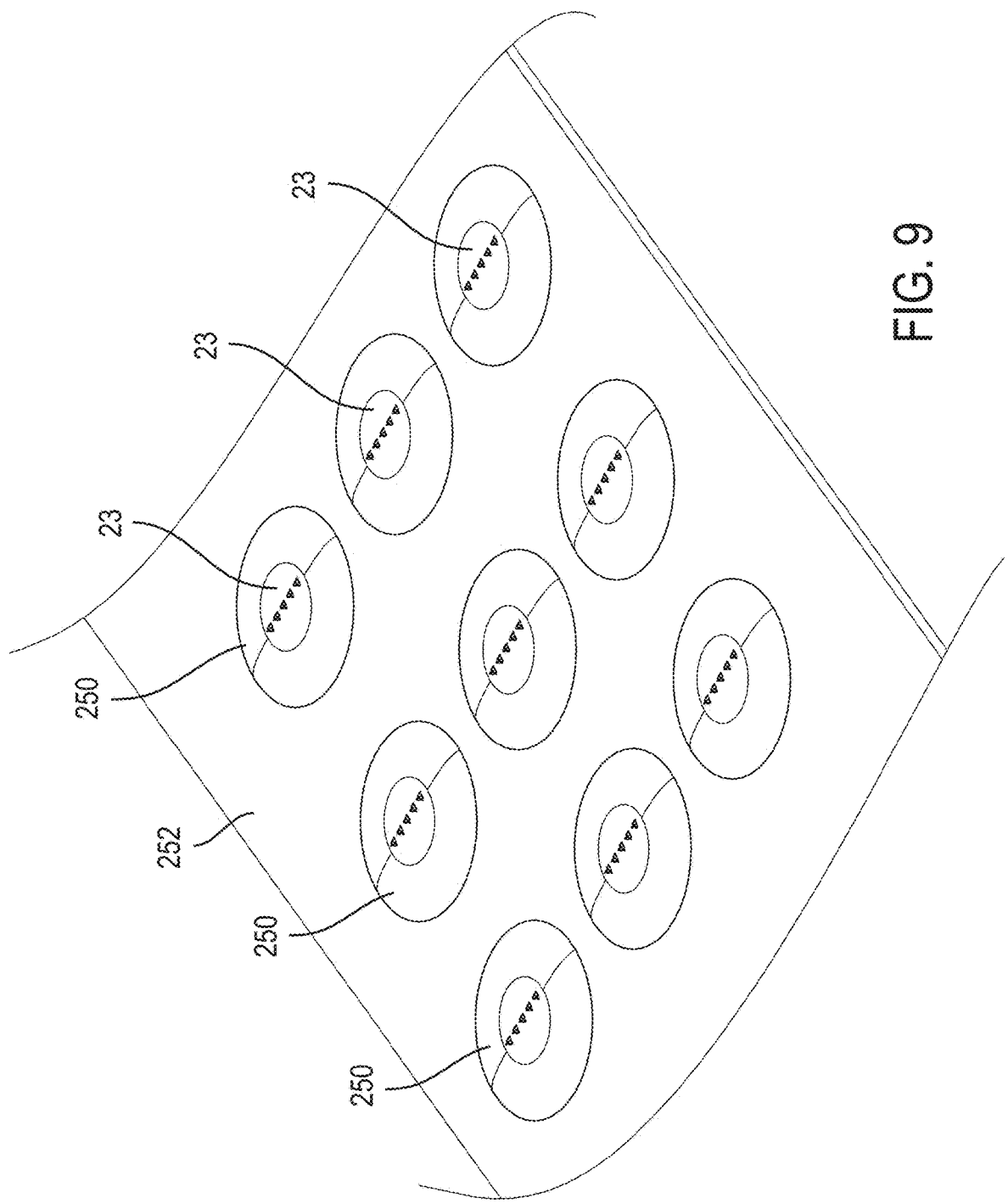
FIG. 9 depicts a perspective view of a portion of a piece of material having a plurality of reservoir portions defined therein.

Referring now to FIG. 9, in some embodiments, reservoirs 12 may be manufactured via a form-fill-seal process. In such embodiments, a number of reservoir portions 250 may be formed in a piece of material 252 (e.g. via an embossing operation, molding, thermoforming, etc.). The piece of material 252 may be formed as a sheet 40A, B (e.g. made from any materials described in relation to FIGS. 4-5) or a rigid body 192. One side of the piece of material 252 may include a number of depressions defined by the reservoir portions 250. The reservoir portions 250 may also define raised sections on the opposing side (shown in FIG. 9) of the piece of material 252. A sharp bearing body 23 may, though need not necessarily, be attached to each of the reservoir portions 250 as described in relation to FIGS. 6, 7, 8. The depressions may be filled with agent and overlaid by a sheet (e.g. made from any materials described in relation to FIGS. 4-5) which is then sealed to the piece of material 252 in areas surrounding the reservoir portions 250. Thus a plurality of sealed reservoirs 12 may be formed as the overlaying sheet is coupled to the piece of material 252. The reservoirs 12 may be separated from one another via cutting and then assembled into delivery devices 10.

Figure 10:
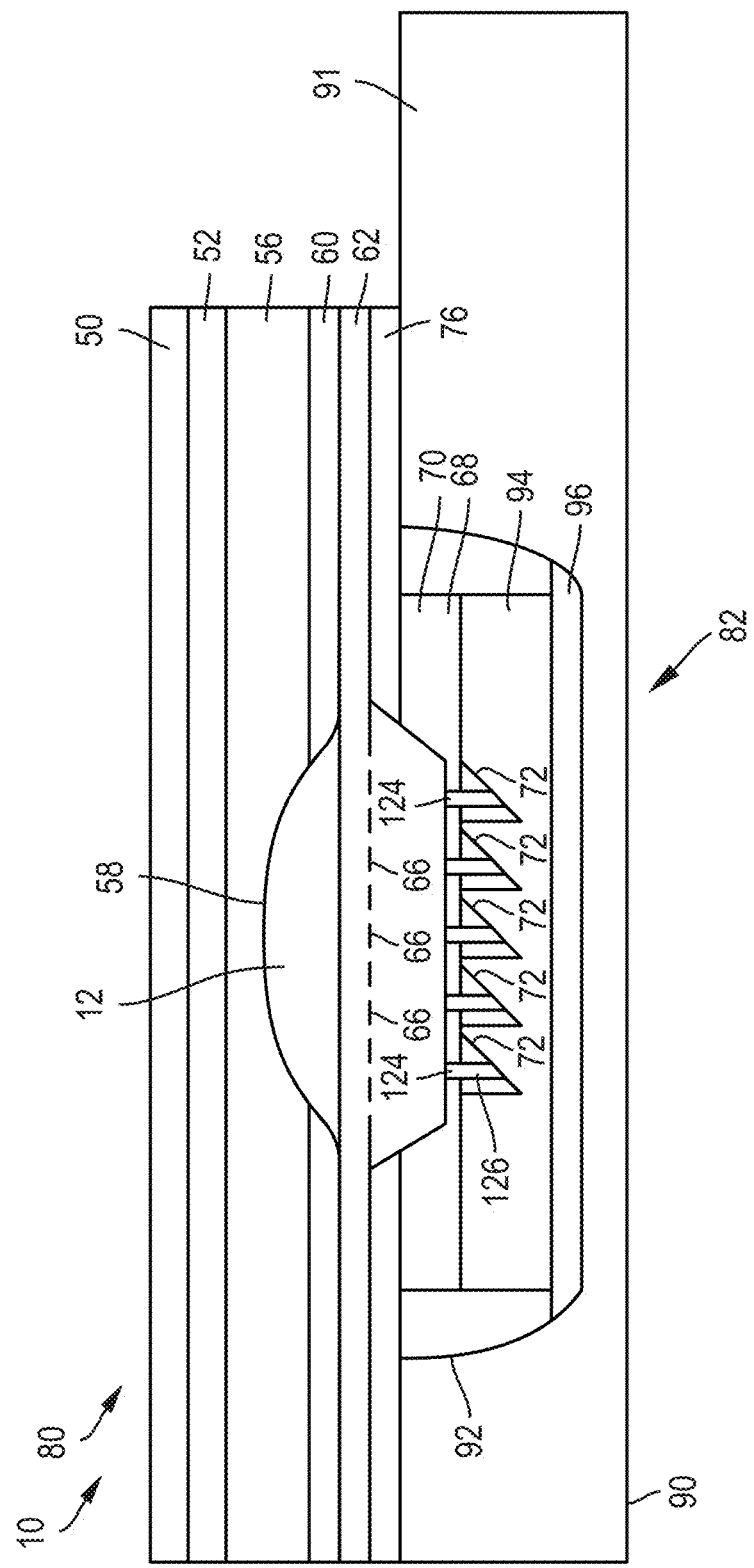
FIG. 10 depicts an embodiment of another exemplary delivery device.

Referring now to FIG. 10, a cross-sectional view of another exemplary embodiment of a delivery device 10 is depicted. As shown, the example delivery device 10 may be constructed of a number of strata of material which are coupled together as a laminate. The delivery device 10 may include a first or outer layer 50. The outer layer 50 may be formed of a flexible material and in certain embodiments may be a fabric material. In some embodiments, the outer layer 50 may be an elastomeric sheet which may be formed at least partially of a stretchable material which may tend to restore to an unstressed state when stretched. The outer layer 50 may be the same material as that used to construct the elastomeric sheet 20 in FIG. 1 for example. Where fabric is used, the fabric may form an elastic sheet and may, for example, be an elastic bandage material including one or more (or all of) of a natural fiber, synthetic fiber, elastic fiber. In some embodiments, the fabric may include cotton, polyester, and a latex free elastic yarn (though latex materials may be included in some examples). In alternative embodiments, the outer layer 50 may not be a fabric and instead may be an elastomeric polymer.

The outer layer 50 material may be covered with an adhesive 52. The adhesive 52 may be present on a proximal face of the outer layer 50. For sake of this discussion proximal and distal are defined in relation to the patient. With respect to FIG. 10, proximal surfaces are those closest to a bottom of the page. Adhesive 52 may or may not be a biocompatible adhesive. In some embodiments, adhesive 52 may be a permanent adhesive. Adhesive 52 may be a flexible adhesive.

The example delivery device 10 of FIG. 10 may also include a second layer 56. The second layer 56 may be attached to the outer layer 50 via the adhesive 52 included on the proximal face of the outer layer 50. The second layer 56 may be formed of a polymer material such as thermoplastic polymer, thermoplastic elastomer (TPE), thermoplastic vulcanisate (TPV) polyester, polyvinyl chloride (PVC), polycarbonate, polyethylene, polypropylene, ethylene-vinyl acetate (EVA), polysiloxane, etc. The material chosen for the second layer 56 may also be a flexible material, but may have a stiffness that is somewhat greater than the material of the outer layer 50 in certain examples.

The second layer 56 may include a reservoir cavity 58 which may be disposed on the proximal face of the second layer 56. The reservoir cavity 58 may be generally centrally disposed on the proximal face of the second layer 56 in various examples. The reservoir cavity 58 may be formed as a depression in the proximal face of the second layer 56. The depression may, for example, be a rounded depression such as a bowl shaped depression in various embodiments. The depression may have a continuously variable depth or may include a generally flat central region depending on the embodiment. In general, the depth of the reservoir cavity 58 may be greatest in a central portion of the reservoir cavity 58.

In some delivery devices 10, the reservoir cavity 58 of the second layer 56 may be formed in an embossing process. Other processes may be used. For example, the reservoir cavity 58 may be thermoformed or vacuum formed in some examples. Where an embossing process is used, any suitable embossing process may be used. For example, the second layer 56 may be formed in a hot embossing process such as a single stage hot embossing process or formed via a roller to roller (R2R) hot embossing process. The embossing process may be an isothermal embossing process. Alternatively, the mold and polymer substrate may be at different temperatures and a non-isothermal embossing process may be used. In such embodiments, either the mold or the polymer substrate may be heated. In alternative embodiments, other processes may be used to generate the reservoir cavity 58. In certain examples, the second layer 56 and the reservoir cavity 58 included therein may be formed together in an injection molding process. In still other examples, the second layer 56 may be formed of a curable (e.g. UV curable) liquid. The second layer 56 and reservoir cavity 58 therein may be formed by applying the uncured liquid to a mandrel with a form for the reservoir cavity 58. This liquid may be subsequently cured to form the second layer 56 and reservoir cavity 58.

Still referring to FIG. 10, the second layer 56 may also be an adhesive bearing layer. As shown in the example embodiment, the proximal face of the second layer 56 may include an adhesive 60 over at least a portion thereof. In the example embodiment, the proximal face of the second layer 56 is completely covered with adhesive 60 with the exception of the area in which the reservoir cavity 58 is defined. In alternative embodiments, the reservoir cavity 58 may also be covered with adhesive 60 and a liner 106 (see, e.g. FIG. 24, FIG. 31) and/or a reservoir 12 (see, e.g. FIGS. 4-5, 6, 7, 8) may be placed in the reservoir cavity 58. The adhesive 60 may be the same as adhesive 52 or may differ from adhesive 52. The adhesive 60 may be a biocompatible adhesive with low extractables. In some embodiments, adhesive 60 may be a hot melt adhesive. Adhesive 60 may have a stiffness greater than the stiffness of adhesive 52.

The delivery device 10 may further include a third layer 62. The third layer 62 may be constructed of a flexible membrane material. The third layer 62 may be attached to proximal face of the second layer 56 via the adhesive 60 on the second layer 56. The third layer 62 may also be adhesive bearing. As shown, the third layer 62 may include an adhesive 76 over at least a portion of a proximal face of the third layer 62. In the example, adhesive 76 is included over the proximal face of the third layer 62 with the exception of the segment of the third layer 62 extending over the reservoir cavity 58. Adhesive 76 may be a different adhesive than adhesives 52 and 60 or may be the same type of adhesive as at least one of adhesives 52 and 60.

The third layer 62 may extend over the reservoir cavity 58 forming a sealed fluid tight reservoir 12. The reservoir 12 may be filled with at least one medical agent. In certain examples, this agent may be a vaccine. In some embodiments, filling of the reservoir 64 may be conducted during a form-fill-seal process. After the reservoir cavity 58 is formed, agent may be supplied into the reservoir cavity 58. The third layer 62 may then be applied over the second layer 56 to complete the reservoir 12 and form a fluid tight seal. The reservoir 12 may be collapsible from a filled state to a depleted state as fluid is dispensed from the reservoir 12. As the reservoir 12 collapses and fluid is driven out of the reservoir 12, the interior volume of the reservoir 12 may decrease until the reservoir 12 has been substantially emptied.

In other embodiments, a reservoir 12 such as those shown and described in FIGS. 4-5, 6, 7 and 8 may be used. In such embodiments, the reservoir 12 may be filled and coupled into the reservoir cavity 58. In such embodiments, the third layer 62 may be omitted or the third layer 62 may be formed of a sheet 40A, B having a portion which defines part of the reservoir 12. Alternatively, in some embodiments a reservoir 12 may be constructed via a blow-fill-seal process. Blow-fill-seal manufactured reservoirs 12 may be used in other embodiments described herein as well. In such embodiments, each parison used to form the reservoir 12 may be a layered co-extrusion of a variety of material layers. For example, an agent compatible layer, gas barrier, water vapor barrier, etc. and perhaps one or more tie layer may be coextruded to form the parison. Thus a multi-layered reservoir 12 may be formed in the blow-fill-seal process. Where various embodiments are described as having a reservoir 12 formed by the reservoir cavity 58 (or a liner 106 therein, see, e.g., FIG. 24) and the third layer 62, it should be understood that a separate reservoir 12 which is installed into the delivery device 10 such as reservoirs 12 described in relation to FIGS. 4-5, 6, 7 and 8 or blow-fill-seal manufactured reservoirs 12 may be used instead in these embodiments.

The reservoir 12 may have any desired interior volume. Where the reservoir 12 is filled with a vaccine, the volume of vaccine may be sufficient for an intradermal vaccination dose. The reservoir 12 may, for example, have an interior volume of 0.25-2 cc though larger and smaller interior volumes may also be used. In certain examples, the reservoir 12 may have a volume of 0.5-1 cc.

The delivery device 10 may be provided in an inactive or storage state. The reservoir 12 may be out of fluid communication with the delivery sharps 72 when the delivery device 10 is in the inactive state. User interaction with the delivery device 10 may transition the delivery device 10 to an active state in which the interior volume of the reservoir 12 is in fluid communication with the delivery sharps 72. To access the interior volume of the reservoir 12, a user may apply a pressure to the reservoir 12 by pressing on the outer layer 50 of the delivery device 10 at a portion of the outer layer 50 which is in alignment with the reservoir 12. The third layer 62 (or a sheet 40A, B of the reservoir 12) may be constructed of a material which may rupture under pressure applied to the reservoir 12. In some embodiments, the third layer 62 may include a weakened portion in the area of the third layer 62 which overlays the reservoir cavity 58. This weakened portion may facilitate rupture of the third layer 62 when pressure is applied to the reservoir 12. Additionally, the weakened portion may help to ensure that the rupture occurs in a desired portion of the material forming the third layer 62. Other reservoir 12 types such as blow-fill-seal manufactured reservoirs 12 may include similar weakened sections or frangibles which break as pressure is applied to the reservoir 12. In alternative embodiments, the weakened section may be omitted and the outlet portion 68 may include at least one reservoir rupture element 24 (see, e.g. FIG. 1).

In the example embodiment, the weakened portion of the third layer 62 is formed by scoring 66 which extends across at least a portion of the segment of the third layer 62 forming a wall of the reservoir 12. The scoring 66 may be generated via material removal process such as a laser scoring or photoablation process which thins the third layer 62 to form the scoring 66. In the example embodiment, the scoring 66 extends in a straight line across this portion of the third layer 62. In other embodiments, the scoring 66 need not be provided in a straight line. In some embodiments, the scoring 66 may be in the form of a plurality of non-parallel line segments which intersect at a common point. For instance, the scoring 66 may be provided in an "X" or cross arrangement (see, e.g., FIG. 30) or asterisk (e.g. an asterisk with 5, 6, 7, 8, and so on spokes) type arrangement. The application of pressure to rupture the reservoir 12 may also aid in ensuring that the delivery sharp(s) 72 appropriately puncture into the patient's skin. In alternative embodiments, example delivery devices 10 may include at least one reservoir rupture element 24 and a displaceable spacer element 28 as discussed in relation to FIG. 1.

Still referring to FIG. 10, the delivery device 10 may further include an outlet portion 68. The outlet portion 68 may include a manifold section 70 and at least one delivery sharp 72. Thus the outlet portion 68 may form the fluid delivering portion of the delivery device 10. The manifold section 70 may include a well 71 which may be recessed into a face of the outlet portion 68 which is opposite that on which the at least one delivery sharp 72 is disposed. The manifold section 70 may be coupled to the third layer 62 of the delivery device 10 when the delivery device 10 is assembled via the adhesive 76 present on the proximal face of the third layer 62. The adhesive 76 may provide a fluid tight seal between the third layer 62 and the face of the outlet portion 68 to which the adhesive 76 is adhered. When the outlet portion 68 is sealingly coupled in place on the delivery device 10, a manifold cavity 74 may be generated adjacent the segment of the third layer 62 forming a wall of the reservoir 12. The manifold cavity 74 may be defined by the segment of the third layer 62 forming the wall of the reservoir 12 and the surface of the well 71. The manifold cavity 74 may have a depth sufficient to allow the scored portion of the third layer 62 to be deformed to the point that the scoring 66 ruptures when the reservoir 12 is put under pressure. The volume of the reservoir cavity 74 may be smaller than that of the reservoir 12 (e.g. no more than 20% of the volume of the reservoir 12). The manifold section 70 may include passages which establish fluid communication between the manifold cavity 74 and the delivery lumens of each of the delivery sharps 72. The manifold cavity 74 may thus be a common volume which communicates with each of the delivery sharps 72 of the delivery device 10.

In the example embodiment, the outlet portion 68 includes five delivery sharps 72 which are arranged in a single row array. The number of delivery sharps 72 and spatial arrangement of delivery sharps 72 may differ in alternative embodiments. As mentioned above, any suitable number of delivery sharps 72 may be included in any suitable number of rows and/or columns. The delivery sharps 72 and the manifold section 70 may be formed as a single, monolithic component in certain embodiments. Alternatively, the manifold section 70 and the delivery sharp(s) 72 of the outlet portion 68 may be separate parts which are coupled to one another during assembly of a delivery device 10. In other embodiments, a sharp bearing body 23 including the delivery sharp(s) 72 may form a part of the reservoir 12 (see, e.g. reservoir 12 of FIG. 6) and a manifold section 70 may not be included.

As shown, the delivery sharps 72 included in the example embodiment are depicted as microneedles. Any suitable microneedle such as any of those shown or described herein may be used. In embodiments where the delivery sharp(s) 72 of an outlet portion 68 are microneedles, the manifold section 70 and the delivery sharp(s) 72 may be (though need not necessarily be) monolithically constructed of a silicon wafer material. The manifold section 70 may, for example, be formed out of the silicon wafer substrate on which the delivery sharps 72 are manufactured. The delivery sharp(s) 72 may be etched into a first side of the substrate material. The manifold well 71 may be etched (e.g. via a single wet etching operation) into a second side of the substrate material opposing the first side. The manifold well 71 may be etched to a depth which places the well 71 into communication with the lumens of the delivery sharp(s) 72 etched into the first side of the substrate. Thus, the flow lumens 126 and manifold passages 124 may be constructed in a single etching operation and may be different regions of the same hole. This may ensure that the manifold passages 124 and flow lumens 126 are coaxial or in alignment with one another.

In some embodiments, and referring now to FIG. 11, the outlet portion 68 may be constructed of a number of separate components. For example, the outlet portion 68 may include a sharp bearing body 23 and a well forming body 73. These components may be coupled to one another so as to form an outlet portion 68. Thus, an outlet portion 68 need not be constructed of a single monolithic piece of material even where the outlet portion 68 or a component of the outlet portion 68 is made from etched silicon. The sharp bearing body 23 may, for example, be constructed of etched silicon and may include a flange 77 which may be coupled onto a receiving shelf defined in the well forming body 73. Any outlet portions 68 described herein may be similarly constructed.

Additionally, in some embodiments, multiple outlet portions 68 or the silicon components of outlet portions 68 may be constructed out of a single larger body of wafer material. Outlet portions 68 or the silicon components thereof may be singulated from the body of wafer material in a suitable cutting operation. For example, outlet portions 68 may be die cut from the single wafer body to create individual monolithic outlet portions 68. Alternatively, an etching process (e.g. a wet etching process) may be used to cut through the substrate material to singulate outlet portions 68 from a larger wafer.

Referring again primarily to FIG. 10, the first, second and third layers 50, 56, 62 (and the associated adhesives 52, 60, 76) as well as the outlet portion 68 may form a first portion 80 of the delivery device 10 (shown alone in FIG. 12). The first portion 80 of the delivery device 10 may be placed on an injection site (see, e.g., FIG. 40) of a patient during use of the delivery device 10. The third layer 62 may form a base of the laminate stack and may be in place adjacent the skin when the delivery device 10 is applied to the patient. As the first, second and third layers 50, 56, 62 (and the associated adhesives 52, 60, 76) may each be constructed of flexible material, the laminate forming the first portion 80 of the delivery device 10 may allow the delivery device 10 to conform to and accommodate contours of a patient's body. The region of the first portion 80 in line with the outlet portion 68 may remain substantially flat when the delivery device 10 is applied to a patient as the outlet portion 68 may be relatively inflexible.

As shown in FIG. 10, the example delivery device 10 may also include a second portion 82. This second portion 82 may be a doffable protective or cover assembly which inhibits ingress of detritus to the area containing the delivery sharp(s) 72. A cover assembly may also block inadvertent contact between a user or manufacturing equipment and the delivery sharp(s) 72. The second portion 82 may additionally serve as a guard which may be reapplied to the first portion 80 after use. Again, this may block inadvertent contact between a user and the delivery sharp(s) 72. As with the first portion 80 of the delivery device 10, the second portion 82 of the delivery device 10 may be constructed of a number of strata of various materials arranged in a laminate.

As shown in FIG. 10, the second portion 82 may include a forth layer of the delivery device 10 which may be referred to herein as a release liner 90. The release liner 90 may be an exterior layer of the second portion 82 and may be disposed on a side of the delivery device 10 opposite the first layer 50. The release liner 90 may be constructed of a polymer material and may be flexible. In some embodiments, the material forming the release liner 90 may be the same as that forming the second layer 56. In some embodiments, the material forming the release liner 90 may be stiffer than the material of the second layer 56. In various examples, the release liner 90 may be constructed of a material which is thermoformable and has a low surface energy (e.g. certain hydrophobic materials). The release liner 90 may be constructed of a material which may be more protective (e.g. higher material strength, hardness, and/or stiffness) than the material forming the second layer 56. Silicone, polypropylene, amorphous polyethylene terephthalate (APET), or PET with a silicone coating may be used in various example embodiments though other materials are also possible.

In the example shown in FIG. 10, the release liner 90 includes an outlet receiving recess 92. The recess 92 may be a depression in a distal face of the release liner 90 and may envelope the outlet portion 68 of the delivery device 10 when the release liner 90 is present. The recess 92 may be generally centrally disposed on the distal face of the release liner 90. The recess 92 may, for example, be a rounded depression such as a bowl shaped depression. The recess 92 may have a continuously variable depth or may include a generally flat central region in various embodiments. In general, the depth of the recess 92 may be greatest in a central portion of the recess 92. The recess 92 may be formed in an embossing process. Any suitable embossing process described herein may be used to form the recess 92. The release liner 90 may be releasably coupled to the first portion 80 of the delivery device 10 via adhesive. In the example embodiment, release liner 90 is coupled to the first portion 80 of the delivery device 10 via the adhesive 76 included on the third layer 62 of the delivery device 10. Preferably, the adhesive 76 connection between the release liner 90 and first portion 80 of the delivery device 10 allows for facile peeling of the release liner 90 from the first portion 80 when the delivery device 10 is readied for use. In some embodiments, the adhesive 76 may initially be placed on a distal face of the release liner 90 during assembly. The adhesive 76 may, however, adhere more robustly to the third layer 62. When the release liner 90 is removed from the delivery device 10 prior to use, the adhesive 76 may remain on the third layer 62 such that the third layer 62 may be adhesive bearing.

In some embodiments, the release liner 90 may include a tab portion 91 which may extend beyond the footprint of the remainder of the delivery device 10. The tab portion 91 may facilitate grasping of the release liner 90 for removal. Additionally, the tab portion 91 may only be supplied on one side of the release liner 90. This may encourage removal of the release liner 90 via peeling off of the release liner 90 from a prescribed side of the delivery device 10. In alternative embodiments, the release liner 90 may be split into a first portion and a second portion which are separately removed. Each portion may include a graspable tab which encourages a user to peel off the portions of the release liner 90 in prescribed directions. In embodiments including one or more microneedles with sides of varying steepness, the release liner 90 may be arranged to encourage a user to peel from the side of the release liner 90 most proximal to the least sharply sloped face of the microneedles.

Once the release liner 90 has been peeled off of adhesive 76, the adhesive 76 may also double as the adhesive used to retain the delivery device 10 in place at an infusion site. Thus, the adhesive 76 may be a skin compatible adhesive or the adhesive 76 may include a region of skin compatible adhesive over at least a portion of the third layer 62 which may contact a patient during use.

Still referring to FIG. 10, the second portion 82 of the delivery device 10 may include a delivery sharp cover 94. The delivery sharp cover 94 may be connected to the release liner 90 via an adhesive 96. The delivery sharp cover 94 may be included in embodiments in which the delivery sharp(s) 72 are microneedles though may also be included in other embodiments. The delivery sharp cover 94 may form a protective barrier over the delivery sharp(s) 72. The delivery sharp cover 94 may ensure that the delivery sharp(s) 72 are shielded during various manufacturing operations. For example, the delivery sharp cover 94 may be installed over the delivery sharp(s) 72 prior to outlet portions 68 being singulated from a larger wafer body in which multiple outlet portions 68 have been created. Additionally or alternatively, the delivery sharp cover 94 may be in place over the delivery sharp(s) 72 during placement (e.g. via a pick and place operation) of an individual outlet portion 68 into a delivery device 10 assembly. Any suitable delivery sharp cover 94 may be used. In some embodiments, the delivery sharp cover 94 may be a domed cap which shields the delivery sharps 72.

In the example embodiment shown in FIG. 10, the delivery sharp cover 94 is depicted as a delivery sharp encasing member. Such a delivery sharp cover 94 is also shown in FIGS. 6-8 among others. A delivery sharp encasing member may surround and be in intimate contact with the delivery sharp(s) 72 on the outlet portion 68. The delivery sharp(s) 72 may be completely embedded within the material of the delivery sharp cover 94. In certain embodiments, such a delivery sharp cover 94 may be formed in place on the outlet portion 68 around the delivery sharp(s) 72. Though described in relation to FIG. 10, delivery sharp covers 94 may be applied to other delivery devices 10 described herein such as that shown in FIG. 1 or FIGS. 22-27. Additionally, delivery sharp covers 94 may be applied to sharp bearing bodies 23 described herein. In embodiments where the delivery sharp(s) 72 are included as a part of a reservoir 12 (see, e.g. reservoir 12 of FIG. 6), the delivery sharp cover 94 may double as a seal which may block flow through the delivery sharp(s) 72 and help to protect the delivery sharp(s) 72.

The delivery sharp cover 94 may for example be a polymer layer which is applied onto an outlet portion 68 or sharp bearing body 23 (see, e.g., FIG. 6) with a thickness that is excess of the height of the delivery sharp(s) 72. In some embodiments, the thickness may be 5% greater or more than the height of the delivery sharp(s) 72. The thickness may be at least 50-100 microns greater than the height of the delivery sharp(s) 72. Any suitable process may be used to apply the polymer layer. In certain embodiments, the polymer may be applied via spin coating, spray coating, or vapor deposition. Where spin coating is used, the applied polymer may have a viscosity selected such that the polymer may uniformly and evenly flow around the delivery sharp(s) 72 at a low spin speed. The viscosity may also be selected such that the polymer does not seep into the flow lumens 126 of the delivery sharp(s) 72. When such a viscosity is used, the delivery sharp(s) 72 may be encased without becoming occluded or clogged.

After application, the polymer layer may be cured. The polymer may, for example, be a UV curing polymer, thermal curing or thermal set polymer, photo curing polymer, etc. Preferably a rapid or fast curing polymer may be used. The polymer may be selected to be a photoimageable polymer in some examples.

The polymer material may also be selected based on adhesive properties of the polymer. For example, the polymer material may be a low tack adhesive which leave minimal residuals when removed. Thus, the polymer layer may adhere to surfaces of the outlet portion 68 or sharp bearing body 23 with which it is in contact. This may allow the delivery sharp cover 94 to resist dislodgement during cutting of outlet portions 68 or sharp bearing bodies 23 from a larger wafer and/or during assembly into a delivery device 10. While the delivery sharp cover 94 may adhere to an outlet portion 68 or sharp bearing body 23 during manufacturing, the use of a low tack adhesive material may allow of the delivery sharp cover 94 to be removed manually with minimal force as the delivery device 10 is prepared for use. In some embodiments, peel strength of the delivery sharp cover 94 from the outlet portion may be no greater than 10 oz/in$^2$. Additionally, the material used may be a highly cohesive polymer to help ensure that the delivery sharp cover 94 comes off in a single piece with minimal residuals left behind. In some embodiments, the polymer layer may include one or more adhesive additives to achieve the desired tack value. Alternatively, the polymer itself may have an appropriate tack value. The delivery sharp cover 94 material may also be selected so as to have an elastic modulus greater than the material forming the delivery sharp(s) 72. Where silicon is used, the elastic modulus of the delivery sharp cover 94 may be greater than that of silicon. This may facilitate removal of the delivery sharp cover 94 without detriment to the delivery sharp(s) 72.

In examples where multiple outlet portions 68 (or sharp bearing bodies 23) are constructed on a single silicon wafer, each outlet portion (or sharp bearing body 23) may be coated to generate its respective delivery sharp cover 94 at the same time. In such embodiments, a side of the wafer in which the set of delivery sharps 72 are defined may be coated (e.g. spin coated) with the delivery sharp cover material. Coated outlet portions 68 or sharp bearing bodies 23 may then be singulated from the larger wafer. In some embodiments, the outlet portions 68 or sharp bearing bodies 23 may be singulated on a piece of conveyer tape which may substantially maintain each part in a known orientation. This may facilitate downstream operations (e.g. picking and placing) in the manufacturing process.

Referring now to FIGS. 10 and 12, and as mentioned above, the example delivery sharp cover 94 may be coupled to the release liner 90 via an adhesive 96. The adhesive 96 may be a more aggressive adhesive than the low tack adhesive material used to create the delivery sharp cover 94. In some embodiments, a hot melt adhesive may be used as adhesive 96. In various embodiments, the adhesive 96 may be a medium tack adhesive. The peel strength between the adhesive 96 and delivery sharp cover 94 may, in some examples, be 50-10 oz/in$^2$ and may be greater than the peel strength between the delivery sharp cover 94 and outlet portion 68. A higher tack adhesive may also be used for adhesive 96 and the peel strength between the adhesive 96 and delivery sharp cover 94 may be in excess of 50 oz/in$^2$. As the delivery sharp cover 94 may be more firmly coupled to the release liner 90 than to the outlet portion 68 (or sharp bearing body 23), when the release liner 90 is peeled from the delivery device 10, the delivery sharp cover 94 may be removed together with release liner 90. Thus, a single interaction with the delivery device 10 may remove the entire second portion 82 of the delivery device 10 and render the delivery device 10 ready for application to the skin of a patient.

Figure 13:
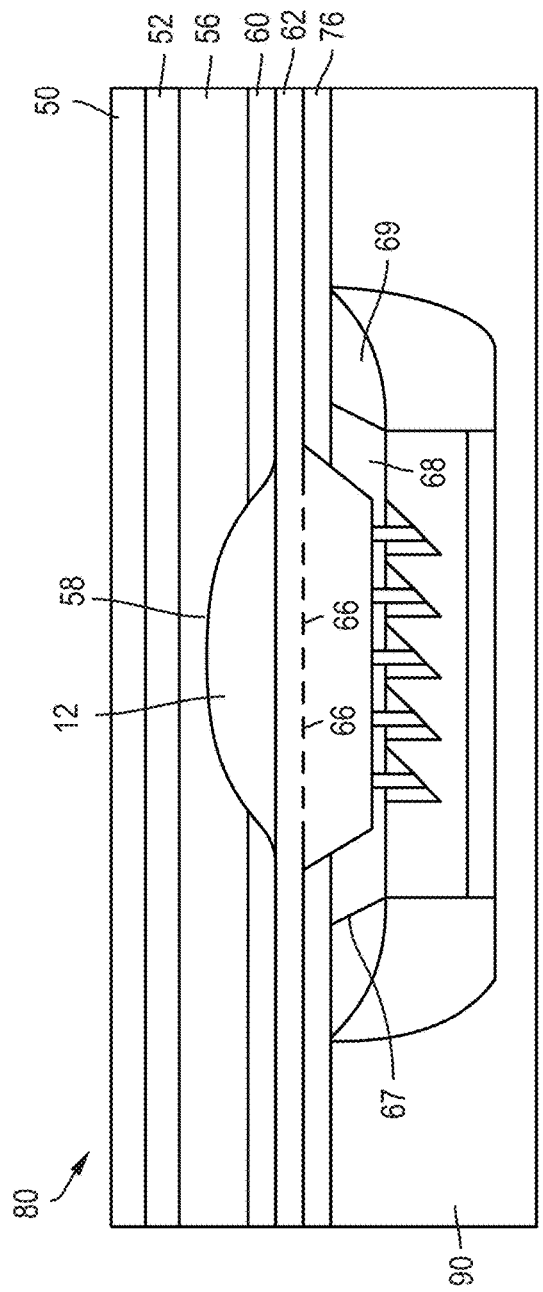
FIG. 13 depicts an embodiment of another example delivery device.
Figure 14:
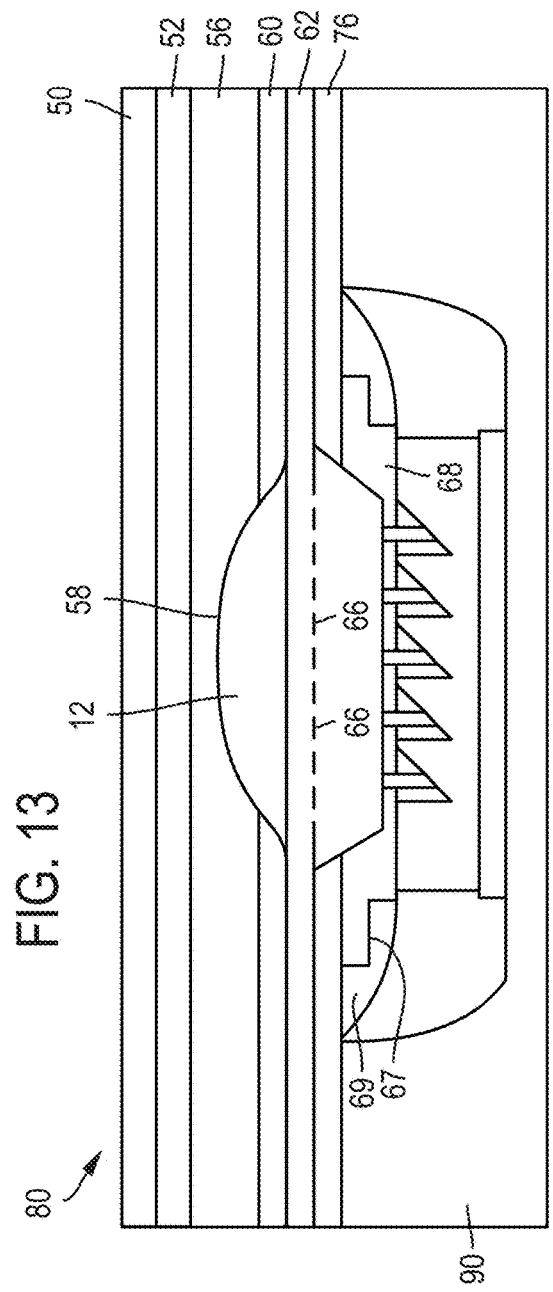
FIG. 14 depicts another embodiment of an example delivery device.
Figure 17:
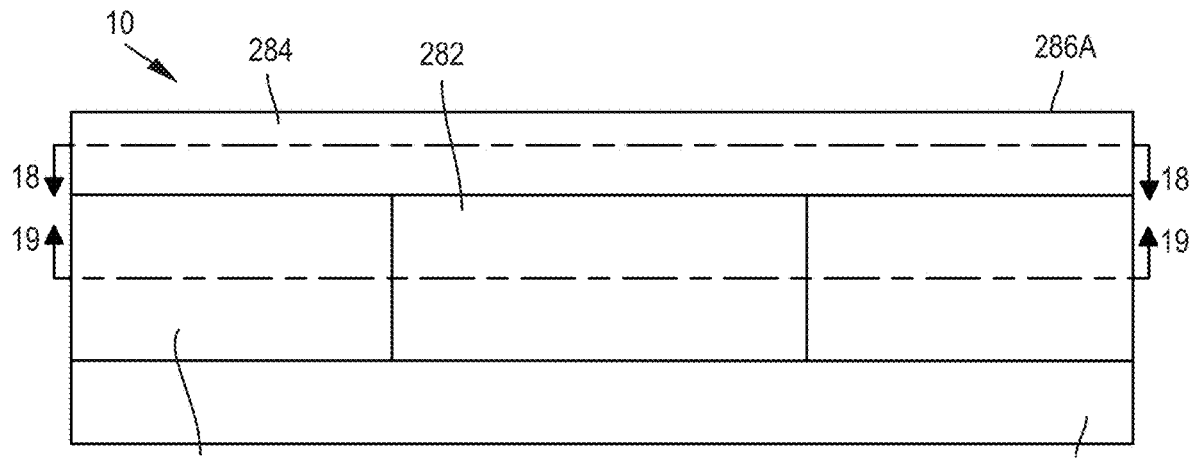
FIG. 17 depicts a top down plan view of a portion of another exemplary embodiment of a delivery device.
Figure 18:
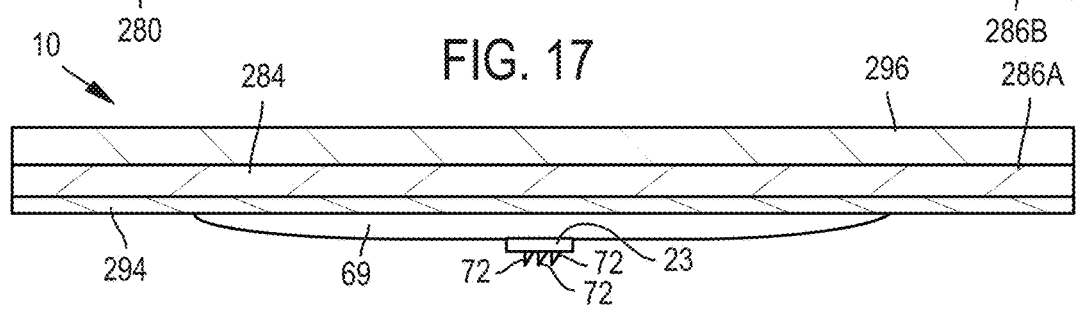
FIG. 18 depicts a cross-sectional view of an example delivery device taken at the indicated cut plane of FIG. 17.

Referring now to FIGS. 13-14, in some embodiments, an outlet portion 68 of a delivery device 10 may be at least partially contained within at least one collar element 69. The collar element(s) 69 may aid in retaining an outlet portion 68 in place on the third layer 62. The collar element 69 may be constructed of a rigid material. In certain embodiments, collar elements 69 may be constructed of a metal material such as steel or titanium. A composite material such as a carbon composite may also be used in various examples. Additionally, polycarbonate may be used in some examples. Other materials such as ceramics, glass, hard plastics, etc. are also possible. Such collar elements 69 may be paired with any of the outlet portions 68 or sharp bearing bodies 23 described herein.

A collar element 69 may include a receptacle 67 which may accept an outlet portion 68 (or sharp bearing body 23) when the collar element 69 is coupled to the third layer 62. In some embodiments, and referring to FIG. 13, the edges of the outlet portion 68 may be chamfered. The receptacle 67 in the collar element 69 may be cooperatively shaped so as to accept this chamfer. Alternatively, and referring now to FIG. 14, the edges of the outlet portion 68 (or sharp bearing body 23) may include a step. A collar element 69 may be cooperatively shaped so as to accept and overhang the step. Other retention arrangements with cooperating collar element 69 and outlet portion 68 (or sharp bearing body 23) shapes or features may be used. The collar element 69 may inhibit removal of the outlet portion 68 (or sharp bearing body 23) as the opening in the proximal side of the collar element 69 may be narrower than the widest section of the outlet portion 68 (or sharp bearing body 23). The collar element 69 may also have a relatively large surface area which is adhered to the third layer 62 via adhesive 76. Thus it may be difficult to peel the collar element 69 from the third layer 62. This may again help to inhibit removal of the outlet portion 68 (or a sharp bearing body 23) from the delivery device 10. The collar element 69 may also double as a stiffener element which may help support the outlet portion 68 (or sharp bearing body 23). In some examples, the collar element 69 and a well forming body 73 (see, e.g., FIG. 11) may be formed as a monolithic structure. A sharp bearing body 23 (see, e.g. FIG. 11) may then be coupled into the well forming body 73 to complete an outlet portion 68.

Referring now to FIG. 15, another embodiment of a delivery device 10 including a collar element 69 is depicted. As shown, the delivery device 10 contains a reservoir 12 which includes a sharp bearing body 23. The collar element 69 may also be included as part of the reservoir 12. The interior volume of the reservoir 12 is primarily defined by the wall of the reservoir cavity 58 (or alternatively a wall of a liner 106, see, e.g., FIG. 26) and a distal surface of the third layer 62. A portion of the third layer 62 is cut away such that the sharp bearing body 23 is in communication with and partially defines the interior volume of the reservoir 12. In alternative embodiments, an outlet portion 68 such as that shown in FIG. 10 may be included in place of the sharp bearing body 23 and a portion of the third layer 62 between the outlet portion 68 and the interior volume of the reservoir 12 may be scored as described elsewhere herein. Pressure applied to the reservoir 12 may cause the scored section to rupture such that the delivery sharps 72 are placed into communication with the interior volume of the reservoir 12.

In other embodiments, the reservoir 12, including the sharp bearing body 23 and collar 69 may be a separate component which is assembled into the delivery device 10. In such embodiments, the reservoir 12 may be constructed of two sheets 40A, B which are for example welded together as described in relation to FIG. 6. In such embodiments, the third layer 62 may be one of the two sheets 40A, B.

As shown, a collar element 69 may be in place around the sharp bearing body 23 and may include a receptacle 67 sized to accept the sharp bearing body 23. The sharp bearing body 23 includes a chamfered periphery (though a stepped periphery like that shown in FIG. 14 may alternatively be used). The receptacle 67 side walls are angled so as to accommodate the chamfer on the sharp bearing body 23. The collar element 69 may inhibit removal of the sharp bearing body 23 from the rest of the reservoir 12 as the opening in the collar element 69 may be narrower than the widest section of the sharp bearing body 23. Additionally, the collar element 69 may act as a stiffener that substantially inhibits bending or stretching of the reservoir 12 in the area surrounding the attachment point of the sharp bearing body 23 to the reservoir wall. The collar element 69 may be constructed of metal, composite, polycarbonate, plastic, or any other suitable material.

Referring now to FIG. 16, in certain examples, a plurality of collar elements 69A, B may be included. As shown, a sharp bearing body 23 (or alternatively an outlet portion 68) may be sandwiched between the first and second collar elements 69A, B. The first collar element 69A may include a receptacle 67 which may accept sharp bearing body 23 (or outlet portion 68). The receptacle 67 may have an opening which is narrower than the widest section of the sharp bearing body 23 so as to inhibit removal of the sharp bearing body 23 (or outlet portion 68). The exemplary first collar element 69A is same as that shown in FIG. 15 in the embodiment of FIG. 16. The second collar element 69B may a be a ring which may overlay and be coupled to a face of the first collar element 69A as well as a portion of the periphery of the sharp bearing body 23 (or an outlet portion 68). The second collar element 69B may be attached to and form a seal against the third layer 62.

In the example embodiment, the collar elements 69A, B and the sharp bearing body 23 are included as part of the reservoir 12. A region of the third layer 62 (or alternatively a sheet 40A, B of the reservoir 12 where the reservoir 12 is created as a separate component) may be removed (e.g. via laser cutting) so as to establish a fluid communication pathway between the interior volume of the reservoir 12 and the flow lumens 126 of the delivery sharps 72. As in other embodiments, a delivery sharp cover 94 may seal the reservoir 12 and block flow through the delivery sharps 72.

Collar elements 69 A, B may also be included where a rupturable reservoir 12 is provided in the delivery device 10. In example delivery devices 10 with a rupturable reservoir 12 (see, e.g., FIG. 10), the second collar element 69B may be attached to the reservoir 12 in an area surrounding a weakened portion or scoring 66.

Referring now to FIGS. 17-20, another exemplary embodiment of a delivery device 10 is shown. As in the embodiment shown in FIGS. 17-20, some delivery device 10 embodiments may be bias element free. Thus, a delivery device 10 may have no pre-stressed component which stores force used to drive fluid out of a reservoir 12. Additionally, in such embodiments, a delivery device 10 may not be subjected to force stored in a bias element when in a storage state. As such a delivery device 10 does not need to withstand a pre-stressed bias element during storage, this may allow for a greater flexibility in materials used to construct the delivery device 10 and may aid in simplifying manufacture. Moreover, the bias element may not need to be constructed to resist creep during storage. Delivery devices 10 of this type may instead include a force generating element 280 which is inactive when the delivery device 10 is in storage. When inactive, the force generating element 280 may exert no force against the reservoir 12. The force generating element 280 may automatically activate when the delivery device 10 is applied to the user. Thus, applying the delivery device 10 to an infusion site on a patient may establish at least one condition which transitions the force generating element 280 into an active state in which the force generating element 280 urges fluid out of the reservoir 12. No user interaction aside from placement of the delivery device 10 at the infusion site may be needed. As the at least one condition that transitions the force generating element 280 to the active state may be automatically established when the delivery device 10 is applied, the delivery device 10 may generally be highly user friendly across a gamut of patient populations and any training needed to use the delivery device 10 may be minimal.

In some examples, the at least one condition may include a temperature change. Depending on the delivery device 10, storage and distribution of the delivery device 10 may be conducted under a cold chain. These may be very cold temperatures selected based on delivery device 10 contents (e.g. −80° C. to −10° C.). Certain SARS-COV-2 vaccines have cold storage temperatures of −70° C. or −20° C. Some delivery devices 10 may also be stored in refrigeration temperatures during cold chain distribution for a period of time prior to use depending on their contents (e.g. above freezing but below 50° and in some examples between 36°-46°). In such embodiments, when the delivery device 10 is in the storage state, the delivery device 10 should be refrigerated and at a relatively cool temperature. When the delivery device 10 is applied to the patient, the temperature difference between the patient's body and the cold chain temperature may cause the force generating element 280 to transition to an active state. In such embodiments, the force generating element 280 may contain a bimetallic region 282 which is positioned against or in alignment with the reservoir 12. In such embodiments, the force generating element 280 may be referred to as a bimetallic actuator. As body heat flows into the force generating element 280 from the patient, the bimetallic region 282 may contort or bend in response to the temperature change. This contortion of the bimetallic region 282 may press against the reservoir 12 and force fluid to be ejected from the reservoir 12 into the patient. Additionally, since the force generating element 280 automatically activates under temperature conditions above that of the cold chain temperature range, such delivery devices 10 may be arranged to self-destruct (e.g. expel their contents) in the event that the cold chain is breached. Thus, the delivery devices 10 may automatically prevent their own use if subjected to certain conditions which may impact the medical agents contained therein.

The delivery device 10 shown in FIGS. 17-20 includes a temperature activated force generating element 280. As shown, the delivery device 10 may include a base layer 284 of a bandage material. The base layer 284 may be divided up into a first and second section 286A, B which may flank the force generating element 280. The delivery device 10 may also include a cover layer 296 (hidden in FIG. 17 for illustrative purposes). The cover layer 296 may form a distal outer surface of the delivery device 10 and may serve to hold the force generating element 280 and first and second section 286A, B of the base layer 284 in place. As in FIG. 10, the delivery sharp(s) 72 of the delivery device 10 shown in FIGS. 17-20 may be protected via a cover. The cover may be a domed piece of rigid material (not shown) which may extend over the delivery sharp(s) 72 and be coupled to the proximal face of the delivery deice 10. Alternatively, the delivery sharp(s) 72 may be encased in a low tack polymer delivery sharp cover 94 (see, e.g. FIG. 10). The delivery sharp cover 94 may be coupled (e.g. as described in relation to FIG. 10) to a release liner 90 (see, e.g., FIG. 10) and be removed with the release liner 90 when the release liner 90 is peeled from the delivery device 10. The delivery sharp(s) 72 of the delivery device 10 shown in FIGS. 17-20 may be microneedles and may be arranged in a one or two dimensional array consisting of any desired number of microneedles.

The force generating element 280 may include a bimetallic region 282 formed of a first layer 288A and second layer 288B. In the example embodiment, the bimetallic region 282 is disposed against a distal face of the reservoir 12. In alternative embodiments, a bimetallic region 282 of a force generating element 280 may be positioned in alignment with a reservoir cavity 58 (see, e.g. FIG. 10). In such examples, a wall of the reservoir cavity 58 may be positioned intermediate the bimetallic region 282 and the reservoir 12. The metals forming the first layer 288A and second layer 288B may have different thermal expansion coefficients. The thermal expansion coefficients and arrangement of the first and second layers 288A, B may be selected to ensure that the bimetallic region 282 bends into the reservoir 12 and substantially empties the reservoir 12 when in the active state.

The delivery device 10 may also include at least one heat directing member which, in some embodiments, may be formed as part of the force generating member 280. The heat directing member may conduct heat from the user's body to the bimetallic region 282. For example, at least one wing 290 of metal or other thermally conductive material may be included as part of the force generating element 280. The at least one wing 290 of the force generating element 280 may not be bimetallic (though could be in certain examples). In some embodiments, a wing 290 may extend from each of two opposing sides of the bimetallic region 282 of the force generating element 280. In such embodiments, the force generating element 280 may be a strip and the bimetallic region 282 may be centrally disposed on the strip. The wing(s) 290 may be formed of the same material as one of the metal layers 288A, B of the bimetallic region 282 and may be continuous therewith. At least a portion of the wing(s) 290 may form a heat collector region 292 of the force generating element 280. The heat collector region(s) 292 may extend along the plane of the base layer 284. The base layer 284 and heat collector regions 292 of the force generating element 280 may be covered in a skin compatible adhesive 294 which may be used to attach the delivery device 10 to a user. Thus the heat collector regions 292 may be held against and separated from the body by a thin layer of adhesive which may have minimal insulating properties.

Figure 19:
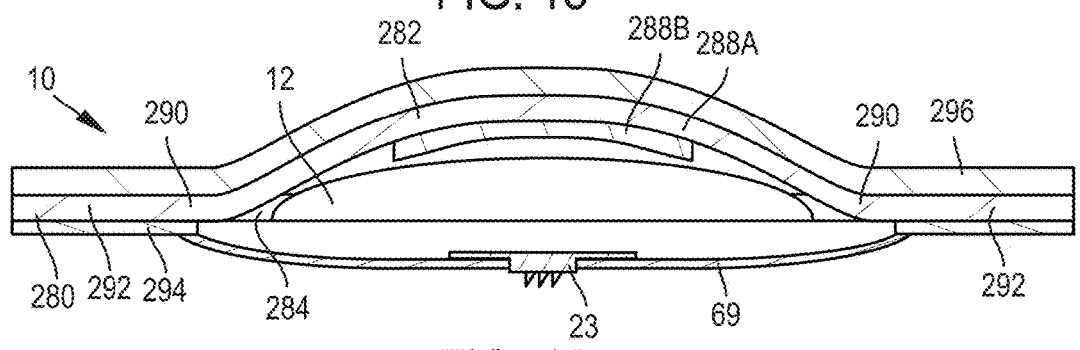
FIG. 19 depicts a cross-sectional view of the example delivery device of FIG. 17 in a storage state.
Figure 20:
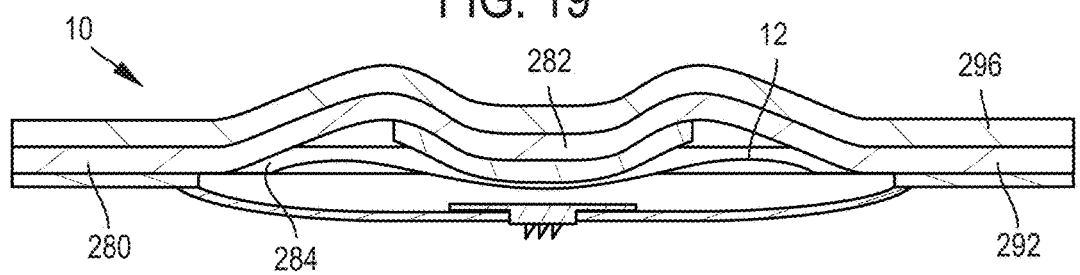
FIG. 20 depicts a cross-section view of the example delivery device of FIG. 17 in an activated state.

In storage and as shown in FIG. 19, the force generating element 280 may be inactive and no force may be exerted against the reservoir 12. When applied to the patient, and referring now primarily to FIG. 20, body heat may be collected via the heat collector regions 292 and may flow to the bimetallic region 282 causing the force generating element 280 to activate. As a result, the bimetallic region 282 may bend into the space occupied by the reservoir 12. This may cause fluid to be driven out of the reservoir 12 and into the patient via one or more delivery sharp 72 included in the delivery device 10 as the reservoir 12 is forced to collapse.

Still referring to FIGS. 17-20, in some embodiments, the reservoir 12 may include a weakened portion (e.g. scored section 66 such as that shown in FIG. 10). Bending of the bimetallic region 282 may exert force upon the reservoir 12 sufficient to rupture the reservoir 12 at the weakened portion. Once ruptured, the reservoir 12 may be placed in fluid communication with the delivery sharp(s) 72. In other examples, the reservoir 12 may be ruptured via manual pressure. In alternative embodiments, bending of the bimetallic region 282 may press the reservoir 12 into one or more reservoir rupture element(s) 24 (see, e.g., FIG. 1). Again, this may establish fluid communication between the delivery sharp(s) 72 and the interior volume of the reservoir 12. In such an example, a spacer element 28 such as that shown in FIG. 1 may be omitted and the reservoir 12 may be adhered to the bimetallic region 282. In still other embodiments, the delivery sharp(s) 72 may be included in a sharp bearing body 23 which is coupled to reservoir 12 via a collar element 69 (or directly or via a well forming body 73). The delivery sharp(s) 72 may be in fluid communication with the interior of the reservoir 12, however, may be plugged by a delivery sharp cover 94 (see, e.g. FIG. 10).

Figure 21:
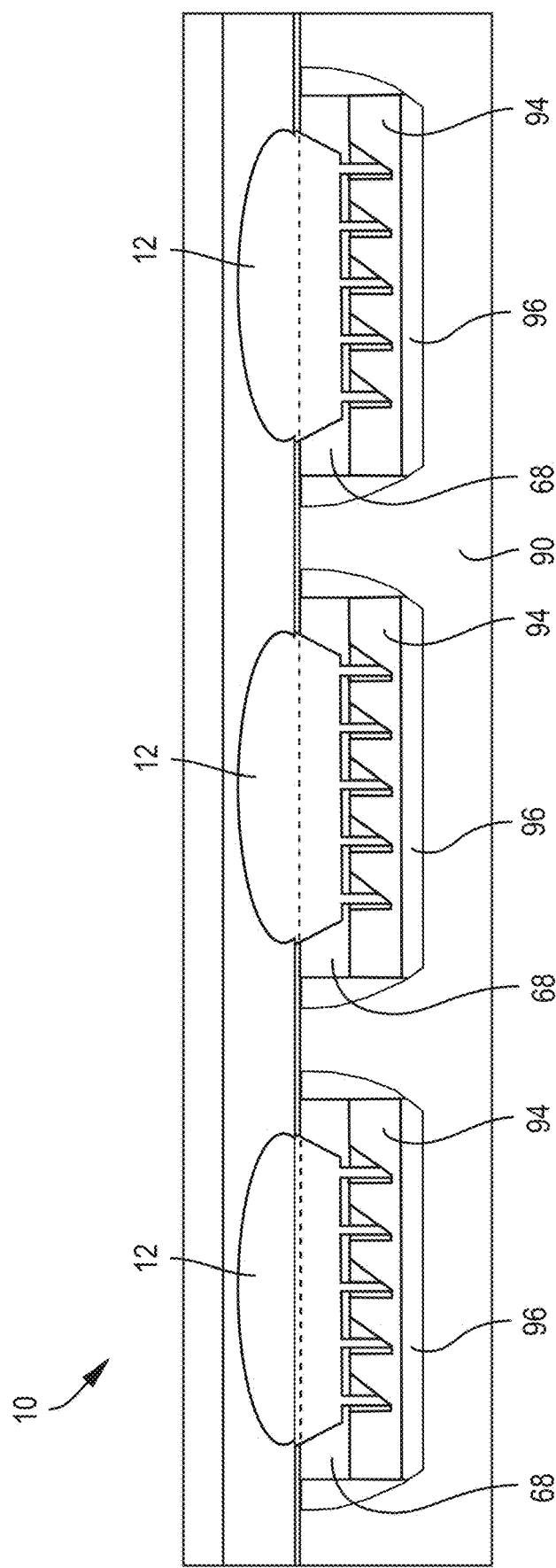
FIG. 21 depicts another exemplary embodiment of a delivery device in which the example delivery device includes a plurality of reservoirs.

Referring now to FIG. 21, a modified version of the delivery device 10 shown in FIGS. 10-11 is depicted. As shown, the example delivery device 10 in FIG. 21 includes multiple reservoirs 12. Other delivery devices 10 described herein such as, for example, those shown in FIG. 1, FIG. 19, FIG. 23, or FIG. 30 may be similarly modified to include multiple reservoirs 12. Collar elements 69 (see, e.g., FIG. 15) or well forming bodies 73 (see, e.g., FIG. 11) may also be included in embodiments with multiple reservoirs 12. In the example embodiment, three reservoirs 12 are depicted, however, in other embodiments a greater or lesser number of reservoirs 12 may be included. The reservoirs 12 are shown arranged in a single row. In other embodiments, reservoirs 12 may be arranged in a one or two dimensional array with any desired number of rows and/or columns. Each of the reservoirs 12 may be formed as described above in relation to FIGS. 10-12. Alternatively, each reservoir 12 may be a separate component (see, e.g., reservoir 12 of FIGS. 4-5) which may be assembled into the delivery device 10. Additionally, each of the reservoirs 12 may be paired with a corresponding outlet portion 68 or may include in a sharp bearing body 23. A delivery sharp cover 94 like that shown and described in relation to FIG. 10 may be provided over the delivery sharp(s) 72 included on each outlet portion 68 (or sharp bearing body 23). As in FIG. 10, the delivery sharp cover 94 may be attached to the release liner 90 of the delivery device 10 via an adhesive 96. As the release liner 90 is peeled from the delivery device 10, the delivery sharp covers 94 may be removed together with the release liner 90 as they may be more firmly coupled to the release liner 90 than to their respective outlet portions 68.

A delivery device 10 with a plurality of reservoirs 12 may be utilized to provide a number of different agents to a patient. The agents may be any agents or combinations of agents described herein. For example, each reservoir 12 may include a different vaccine. Thus a single delivery device 10 may, for example, be used to supply a number of vaccinations to a user. These vaccinations may, for example, be vaccines of a typical vaccination schedule in some embodiments. As the delivery sharp(s) 72 associated with each reservoir 12 may be microneedles, vaccination may proceed painlessly and dose or injection sparing may be achieved via the shallow injection. Thus such a delivery device 10 may be more tolerable or less traumatic to certain patients who may be averse to needles (e.g. young children). Alternatively, each of the reservoirs 12 may include a volume of the same vaccine. In such embodiments, the delivery device 10 may deliver the vaccine to a number of infusion sites on a patient. This may aid in exposing a greater area of tissue to the vaccine which may evoke a stronger immune response. As mentioned above, any of the delivery devices 10 described herein may be constructed with a plurality of reservoirs 12.

Figure 22:
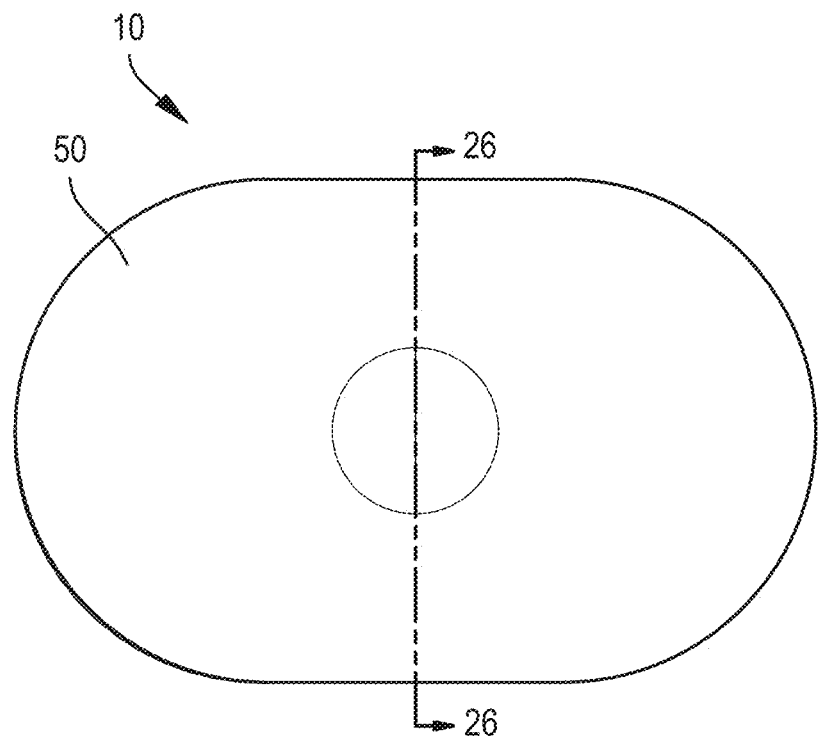
FIG. 22 depicts a top plan view of yet another embodiment of an example delivery device.
Figure 23:
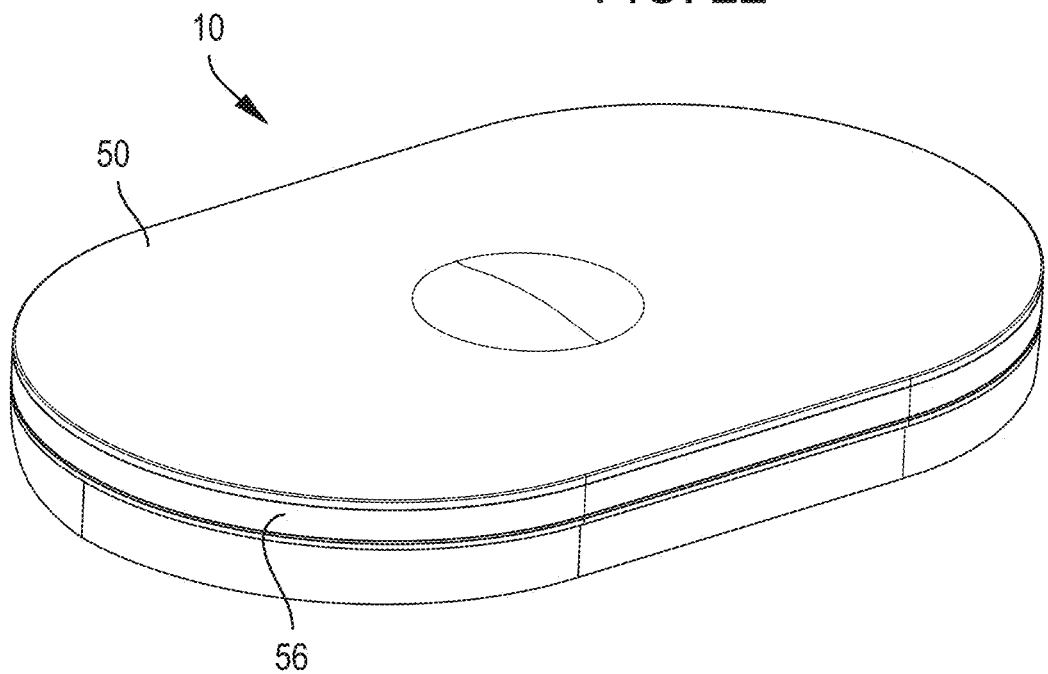
FIG. 23 depicts a perspective view of the example delivery device of FIG. 22.

Referring now to FIGS. 22-23 a top plan view and a perspective view of another exemplary delivery device 10 are respectively depicted. As shown, the delivery device 10 may have an obround footprint. This obround footprint may approximate the shape of a conventional Band-Aid. Other embodiments may have different shaped footprints including, but not limited to, round, circular, polygonal, etc. shapes. The delivery device 10 may also have a low profile. When applied to a user, the delivery device 10 may flex to conform to various contours of a patient's body.

Figure 24:
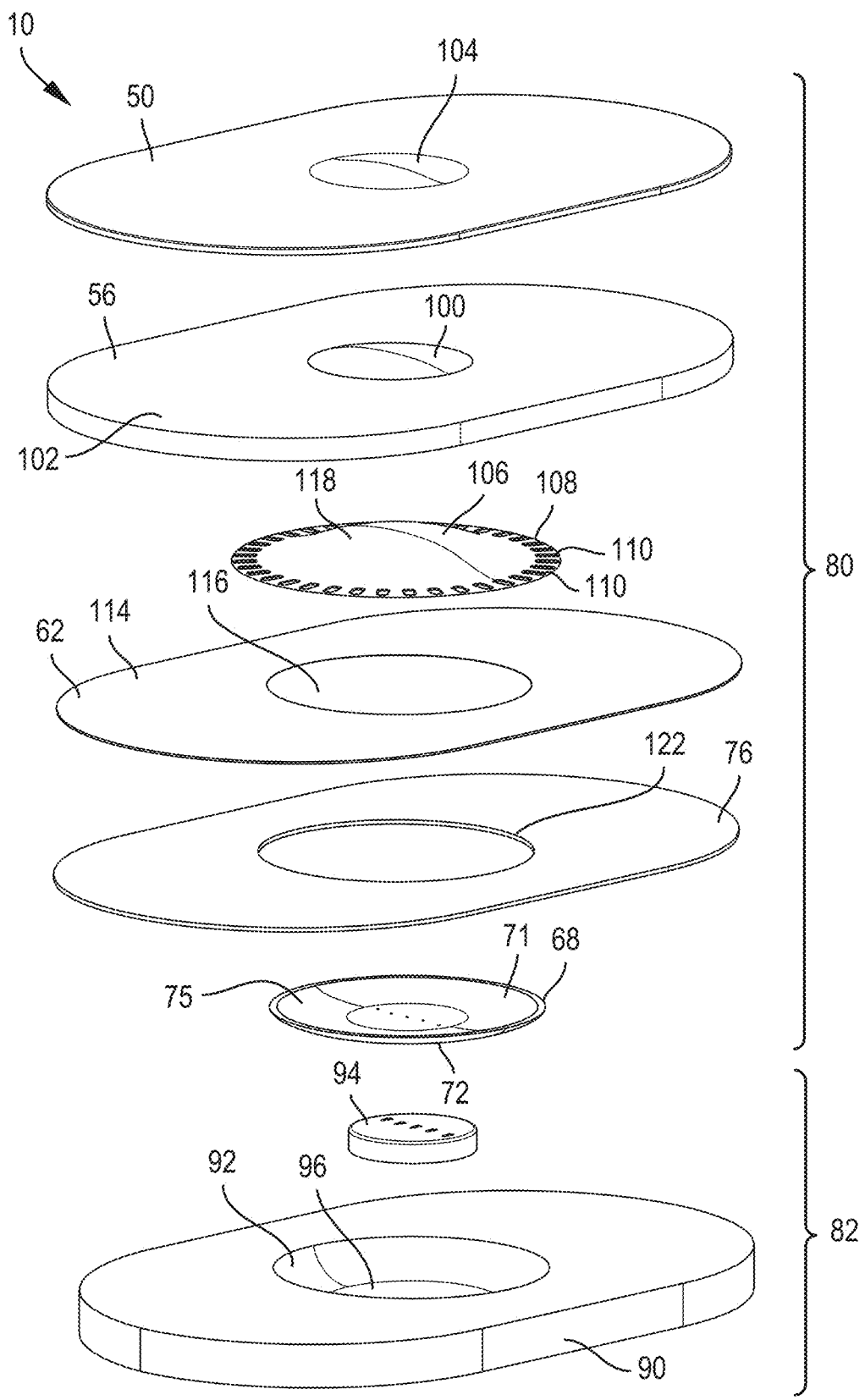
FIG. 24 depicts an exploded perspective view of the example delivery device of FIG. 22.
Figure 25:
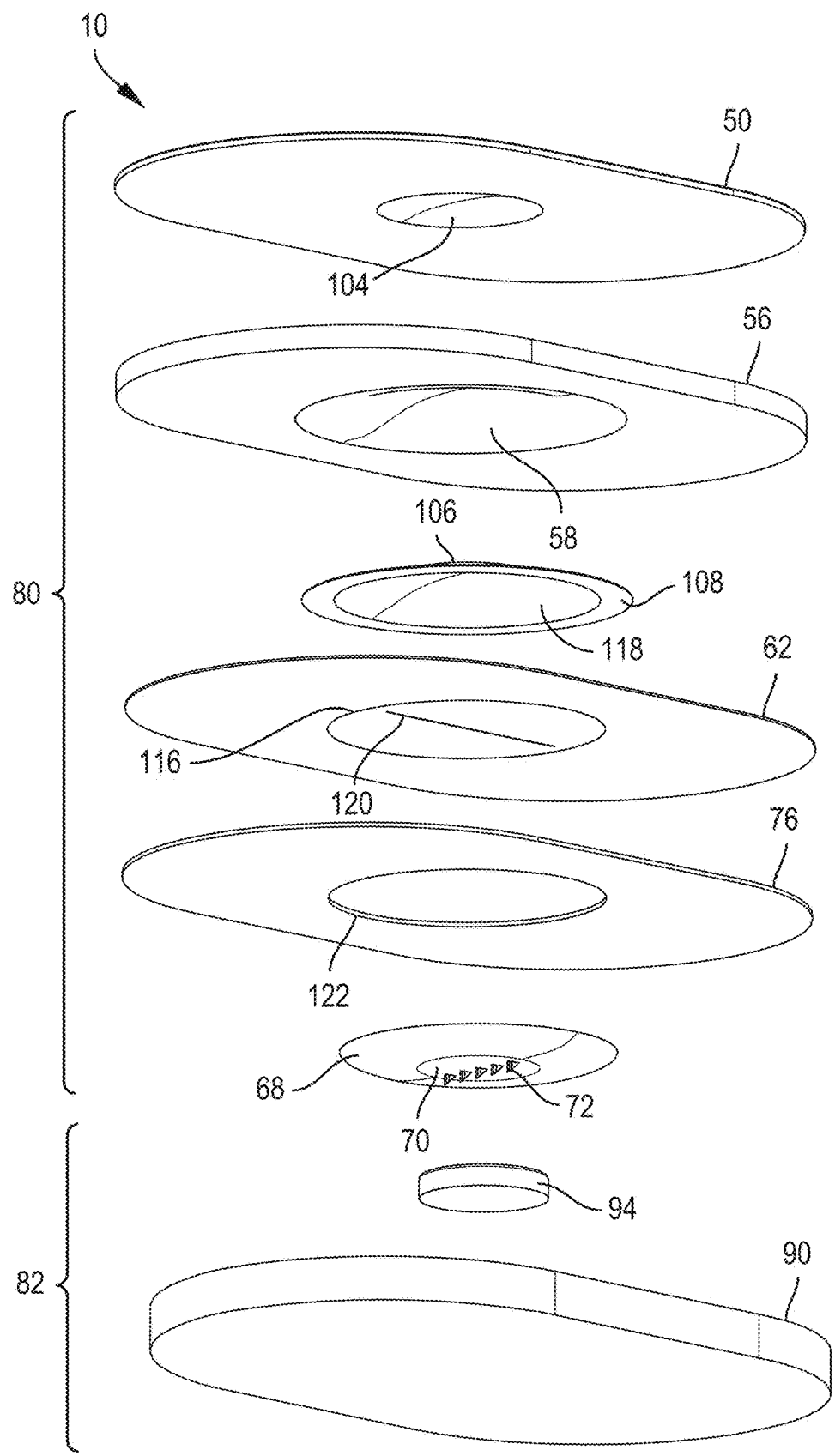
FIG. 25 depicts another exploded perspective view of the example delivery device of FIG. 22.

Referring now also to FIG. 24-25, which depict exploded views of the example delivery device 10 of FIGS. 22-23, and FIG. 26, a cross-section taken at the indicated cut plane in FIG. 22, the example delivery device 10 may include a laminate of a number of strata of material. The delivery device 10 may include a first or outer layer 50. The outer layer 50 may be formed of a flexible, at least partially elastomeric material and in certain embodiments may be a fabric material. The outer layer 50 may be formed as described in relation to FIG. 10 in some examples. In some embodiments, the outer layer 50 may be the same material as the elastomeric sheet 20 of FIG. 1. The outer layer 50 material may be adhesive bearing (see, e.g. any adhesive described in relation to adhesive 52 of FIG. 10). The adhesive may be present on a proximal face of the outer layer 50.

The delivery device 10 may also include a second layer 56. The second layer 56 may be attached to the outer layer 50 via the adhesive included on the proximal face of the outer layer 50. The second layer 56 may be formed of a polymer. The material chosen for the second layer 56 may also be a flexible material. The second layer 56 may be formed as described in relation to FIG. 10 in some examples. The second layer 56 may include a reservoir cavity 58 which may be disposed on the proximal face of the second layer 56. The reservoir cavity 58 may be generally centrally located in the proximal face of the second layer 56. The reservoir cavity 58 (see, e.g., FIG. 26) may have a depth which is greater than the thickness of a main body 102 of the second layer 56. In order to accommodate this, the distal face of the second layer 56 may include a raised section 100. This raised section 100 may be a thin wall which partially defines the reservoir cavity 58. The raised section 100 may be included as a rounded bump or bump in the form of a spherical section in some embodiments which is proud of the distal face of the second layer 56. The outer layer 50 may conform to the shape of the raised section 100. Thus, when applied on a patient, a raised area 104 may be perceptible when viewing the outer layer 50 of the delivery device 10. As the outer layer 50 may include an elastomeric material, the raised section 100 may cause the outer layer 50 to stretch as it conforms to the raised section 100. This may store a bias force in the outer layer 50 which may urge fluid out of the reservoir 12 of the delivery device 10 when the delivery device is applied to a user.

The raised section 100 may be deformable under manual pressure. In some embodiments, portions of the main body 102 at the periphery of the raised section 100 may also deform under manual pressure. In some embodiments, manual pressure may be applied to totally or at least partially invert the reservoir cavity 58 during use. The raised area 104 visible on the outer layer 50 of the delivery device 10 may provide a visual cue to a user as to where manual pressure should be directed during use.

As in other embodiments described herein, the reservoir cavity 58 of the second layer 56 may be formed in an embossing process such as any of those described herein. Any other suitable process such as any of those described herein may alternatively be used to create the reservoir cavity 58.

Still referring to FIGS. 24 and 25, example delivery devices 10 may include a liner 106 layer or stratum. The liner 106 may be a sheet of material which may be placed in the reservoir cavity 58. Other embodiments described herein, such as that shown in FIG. 10, may also include a liner 106 layer. The liner 106 may be constructed of a material or a number of layers of material such as any of those described in relation to FIGS. 4-5. The liner 106 may allow for a wider range of materials to be used to form the second layer 56 of the delivery device 10 as the second layer 56 need not be compatible with any agent intended to be filled into the reservoir 12. Use of a liner 106 may also allow the reservoir 12 of the delivery device 10 to be formed separately from other components of the delivery device 10 and then assembled into the delivery device 10.

The liner 106 may include a main section 118 and a peripheral flange 108 which extends around the main section 118 of the liner 106. The main section 118 of liner 106 may include an outward facing surface which may be in contact with the wall of the reservoir cavity 58 or an adhesive coating the wall of the reservoir cavity 58. The opposing face of the main section 118 of the liner 106 may form a wall of the interior volume of the reservoir 12 of the delivery device 10. The peripheral flange 108 may seat into a peripheral recess 112 included in the second layer 56 surrounding the reservoir cavity 12. The liner 106 may be coupled to the second layer 56 via a weld (e.g. ultrasonic weld) which attaches the peripheral flange 108 to the peripheral recess 112. The peripheral flange 108 may include a number of ridges 110 of material. The ridges 110 in the example extend in a radial direction and are spaced at even angular increments about the peripheral flange. In alternative embodiments, the ridges 110 may be at uneven angular increments. These ridges 110 may provide excess material which may facilitate sonic welding of the liner 106 to the second layer 56. In alternative embodiments, the liner 106 may be maintained in the reservoir cavity 58 via adhesive 60 covering the proximal face of the second layer 56 or the outward facing surface of the liner 106.

In the example embodiment, the liner 106 is shown as having a shape which conforms to the shape of the reservoir cavity 58. A domed shape is specifically shown in FIGS. 24-26. The liner 106 may be pre-formed so as to assume this domed shape in a resting or unstressed state. The domed shape may, for example, be vacuum or thermoformed into the liner 106 material or the domed shape may be formed during injection molding of the liner 106. Any other suitable process for pre-forming the liner 106 may alternatively be used. In alternative embodiments, the liner 106 may not be pre-formed to mimic the shape of the reservoir cavity 58. Instead, the liner 106 may be flexible or stretchable and may conform to the shape of the reservoir cavity 58 when the reservoir 12 is filled with fluid.

The delivery device 10 may further include a third layer 62. The third layer 62 may be constructed of a flexible membrane material. The third layer 62 may include a main body 114 and a reservoir portion 116. The third layer 62 may be attached to a proximal face of the second layer 56 via adhesive (see e.g. any adhesive described in relation to adhesive 60 of FIG. 10) on the second layer 56. The third layer 62 may extend over the reservoir cavity 58 and liner 106 forming a sealed, fluid tight reservoir 12. The interior volume of the reservoir 12 may be defined by the liner 106 and the reservoir portion 116 of the third layer 62. The reservoir 12 may be filled with at least one medical agent.

In certain examples, the agent loaded into the reservoir 12 may be a vaccine. Filling of the reservoir 12 may be conducted via a form-fill-seal process. After the reservoir cavity 58 is formed and the liner 106 is coupled into place, agent may be supplied into the lined reservoir cavity 58. The third layer 62 may then be applied over the second layer 56 and liner 106 to complete the reservoir 12 and form a fluid tight seal for the reservoir 12. The third layer 62 may be coupled in fluid tight relation to the liner 106 at the peripheral flange 108 of the liner 106. The third layer 62 and peripheral flange 108 may be coupled via sonic (e.g. ultrasonic) welding, adhesive, heat, etc.

In alternative embodiments, the reservoir 12 may be formed via welding as described in, for example, FIGS. 4-5. The liner 106 and a portion of the third layer 62 may act as and be constructed out of the same material(s) as sheets 40A, 40B (see, e.g., FIG. 4-5) in such examples. Where the reservoir 12 is formed via welding, the reservoir 12 may be filled as described in relation to FIGS. 4-5. In still other embodiments, the reservoir 12 may be manufactured via a blow-fill-seal process and may be coupled into the reservoir cavity 58 instead of the liner 106. In such embodiments, the third layer 62 may be omitted.

The reservoir 12 may have any desired interior volume. In certain examples, the reservoir 12 may have an interior volume of 0.25-2 cc though larger and smaller interior volumes may also be used. In certain examples where the reservoir 12 is filled with a vaccine, the interior volume may be 0.5-1 cc.

Referring now also to FIG. 27, a detailed view of the indicated region of FIG. 26, in order to access the reservoir 12, a user may apply a pressure to the reservoir 12 by pressing on the raised area 104 of the outer layer 50 of the delivery device 10. The third layer 62 may be constructed of a material which may rupture under pressure applied to the reservoir 12. In some embodiments, the third layer 62 may include a weakened portion in its reservoir portion 116. This weakened portion may facilitate rupture of the reservoir portion 116 when pressure is applied to the reservoir 12. Additionally, the weakened portion may help to ensure that the rupture occurs in a desired location of the reservoir portion 116 or that the rupture occurs in a desired manner. The weakened portion may be generated by removing material of the reservoir portion 116 in a suitable material removal process to thin a section of the reservoir portion 116. Where a blow-fill-seal manufactured reservoir 12 is used, the reservoir 12 may similarly include a weakened section or frangible which may break when pressure is exerted on the reservoir 12.

In the example embodiment, the weakened portion of the third layer 62 is formed as a score line 120 which extends across the reservoir portion 116 of the third layer 62. The score line 120 may be formed via laser scoring or photoablation in various embodiments. In the example embodiment, the score line 120 extends in a straight line across this portion of the third layer 62. In other embodiments, a score line 120 need not be a straight line. Any shape or configuration described for the scoring 66 in relation to FIG. 10 may, for example, be used. The application of pressure to rupture the reservoir 12 may also aid in ensuring that the delivery sharp(s) 72 appropriately puncture into the patient's skin.

Referring again primarily to FIGS. 24-26, an adhesive layer 76 may be included over at least a portion of a proximal face of the third layer 62. In the example, the adhesive layer 76 includes a central opening 122. The central opening 122 may be disposed so as to align with the location of the reservoir portion 116 of the third layer 62.

Still referring to FIGS. 24-26, the delivery device 10 may further include an outlet portion 68 which may form a fluid delivering portion of the delivery device 10. The outlet portion 68 may include a at least one delivery sharp 72 and stiffener section 75. The stiffener section 75 may define a well 71. The stiffener section 75 may be formed monolithically with the rest of the outlet portion 68 as shown. Alternatively, the stiffener section 75 may be a collar element 69 (see, e.g., FIG. 15 or FIG. 30) or a well forming body 73 (see, e.g., FIG. 11). In such embodiments, the delivery sharps 72 may be included in a sharp bearing body 23 which may assemble into the stiffener section 75. The stiffener section 75 may add extra material to the outlet portion 68 and help to ensure that the outlet portion 68 is robust. The stiffener section 75 may also raise the delivery sharps 72 off the surface of the third layer 62. This may help to ensure that pressure applied to the delivery device 10 during use gets concentrated on the delivery sharps 72. This may aid in ensuring that the delivery sharps 72 appropriately puncture into the user.

When the outlet portion 68 is coupled in place on the delivery device 10, a manifold cavity 74 may be defined by the surface of the well 71 and the surface of the reservoir portion 116. Passages 124 which establish fluid communication between the manifold cavity 74 and the delivery lumens 126 of each of the delivery sharps 72 may be included in the outlet portion 68. The manifold cavity 74 may thus be a common volume which communicates with each of the delivery sharps 72.

In the example embodiment, the outlet portion 68 includes five delivery sharps 72 which are arranged in a single row array. The number of delivery sharps 72 and spatial arrangement of delivery sharps 72 may differ in alternative embodiments. As mentioned above, any suitable number of delivery sharps 72 may be included in any suitable number of rows and/or columns. As described elsewhere herein, the delivery sharps 72 and the stiffener section 75 may be formed as a single, monolithic component in certain embodiments. Alternatively, the stiffener section 75 and the delivery sharp(s) 72 of the outlet portion 68 may be separate parts which are coupled to one another during assembly.

As shown, the delivery sharps 72 included in the example embodiment are depicted as microneedles. Any suitable microneedles such as any of those shown or described herein may be used. In embodiments where the delivery sharp(s) 72 of an outlet portion 68 are microneedles, the outlet portion 68 may be manufactured as described above in relation to FIG. 10. In alternative embodiments, and as mentioned above, the delivery device 10 may also include a collar element 69 similar to that described in relation to FIG. 13-14 or a well forming body 73 as described in relation to FIG. 11.

Still referring to FIGS. 24-26, the first, second, and third layers 50, 56, 62, the associated adhesives 52, 60, and 76, as well as the liner 106 and the outlet portion 68 may form a first portion 80 of the delivery device 10 (best shown in FIG. 24). The first portion 80 of the delivery device 10 may be adhered in place on an injection site (see, e.g., FIG. 40) of a patient via a portion of the adhesive layer 76 during use of the delivery device 10. As the first, second and third layers 50, 56, 62 (and the associated adhesives 52, 60, and 76,) may each be constructed of flexible material, the laminate forming the first portion 80 of the delivery device 10 may allow the delivery device 10 to conform to and accommodate contours of a patient's body. The region of the first portion 80 in line with the outlet portion 68 may remain substantially flat when the delivery device 10 is applied to a patient as the outlet portion 68 may be relatively inflexible.

As shown in FIGS. 24-26, the example delivery device 10 may also include a second portion 82. This second portion 82 may be a doffable protective or cover assembly which inhibits ingress of detritus to the area containing the delivery sharp(s) 72. The protective assembly may also block inadvertent contact between a user or manufacturing equipment and the delivery sharp(s) 72. As with the first portion 80 of the delivery device 10, the second portion 82 of the delivery device 10 may be constructed of a number of strata of various materials arranged in a laminate.

As shown in FIGS. 24-26, the second portion 82 may include a forth layer of the delivery device 10 which may be referred to herein as a release liner 90. The release liner 90 may be an exterior layer of the second portion 82 and may be disposed on a side of the delivery device 10 opposite the outer layer 50. The release liner 90 may be constructed as described in relation to FIG. 10. In the example embodiment, the release liner 90 includes an outlet receiving recess 92. The recess 92 may be a depression in a distal face of the release liner 90 and may envelope the outlet portion 68 of the delivery device 10 when the release liner 90 is present on the delivery device 10. The recess 92 may be formed and structured as described in relation to FIG. 10.

The release liner 90 may be releasably coupled to the first portion 80 of the delivery device 10 via adhesive. In the example embodiment, release liner 90 is coupled to the first portion of the delivery device 10 via the adhesive 76 between the third layer 62 of the delivery device 10 and the release liner 90. Preferably, the adhesive 76 connection between the release liner 90 and first portion 80 of the delivery device 10 allows for facile peeling of the release liner 90 from the first portion 80 when the delivery device 10 is readied for use. With the release liner 90 removed, the adhesive 76 may also double as the adhesive used to retain the delivery device 10 in place at an infusion site. Thus, the adhesive 76 may be a skin compatible adhesive or the adhesive 76 may include a region of skin compatible adhesive over at least a portion of the third layer 62 which may contact a patient during use. The release liner 90 may be arranged so as to encourage peeling off of the release liner 90 from a prescribed direction as described in relation to FIG. 10.

Still referring to FIGS. 24-26, the second portion 82 of the delivery device 10 may include a delivery sharp cover 94. The delivery sharp cover 94 may be connected to the release liner 90 via an adhesive (see, e.g., adhesive 96 of FIG. 10). The delivery sharp cover 94 may be included in embodiments in which the delivery sharp(s) 72 are microneedles though may also be included in other embodiments. The delivery sharp cover 94 may form a protective barrier over the delivery sharp(s) 72 and may ensure that the delivery sharp(s) 72 are shielded during various manufacturing operations. For example, the delivery sharp cover 94 may be installed over the delivery sharp(s) 72 prior to outlet portions 68 (or sharp bearing bodies 23 such as that shown in FIG. 11) being singulated from a larger wafer body in which multiple outlet portions 68 have been created. Additionally, or alternatively, the delivery sharp cover 94 may be in place over the delivery sharp(s) 72 during placement (e.g. via a pick and place operation) of an individual outlet portion 68 into a delivery device 10 assembly.

In the example embodiment shown in FIGS. 24-26, the delivery sharp cover 94 is depicted as a delivery sharp encasing member. This delivery sharp encasing member surrounds and is in intimate contact with the delivery sharp(s) 72 on the outlet portion 68. The delivery sharp(s) 72 may be completely embedded within the material of the delivery sharp cover 94. In certain embodiments, such a delivery sharp cover 94 may be formed in place on the outlet portion 68 around the delivery sharp(s) 72. The delivery sharp cover 94 may for example be formed as described in relation to FIG. 10.

As in the example embodiment of FIG. 10, the delivery sharp cover 94 of FIGS. 24-26 may be constructed of a low tack polymer material (described in greater detail in relation to FIG. 10). The adhesive (see, e.g., adhesive 96 of FIG. 10) coupling the delivery sharp cover 94 to the release liner 90 may be a more aggressive adhesive than the low tack adhesive material used to create the delivery sharp cover 94. In various embodiments, the adhesive 96 may be a medium tack adhesive or a higher tack adhesive. As a result, the delivery sharp cover 94 may be more firmly coupled to the release liner 90 than to the outlet portion 68.

Figure 28:
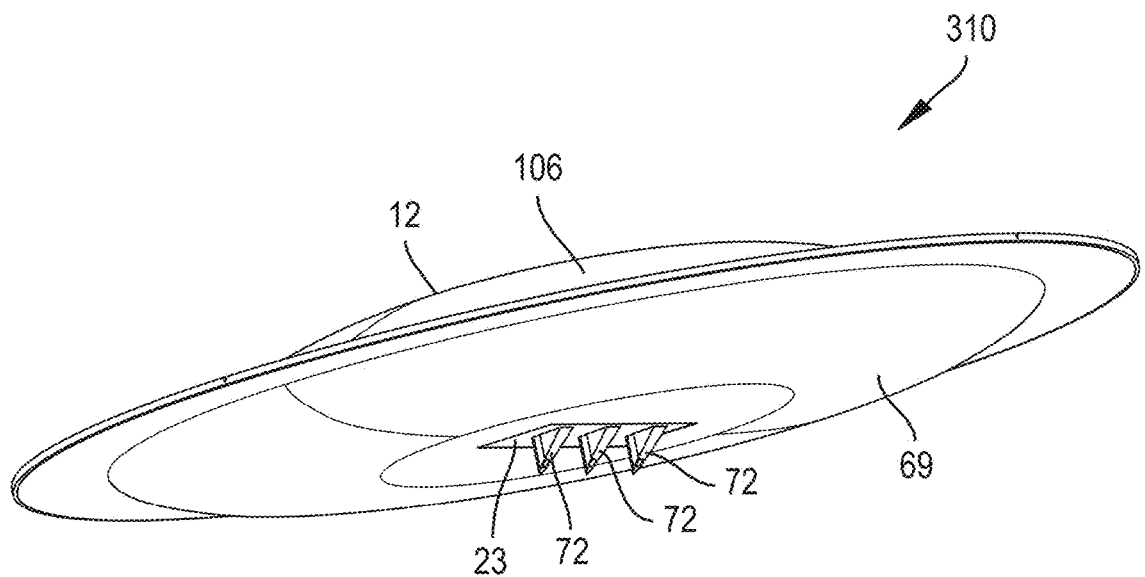
FIG. 28 depicts a perspective view of an example reservoir assembly.
Figure 29:
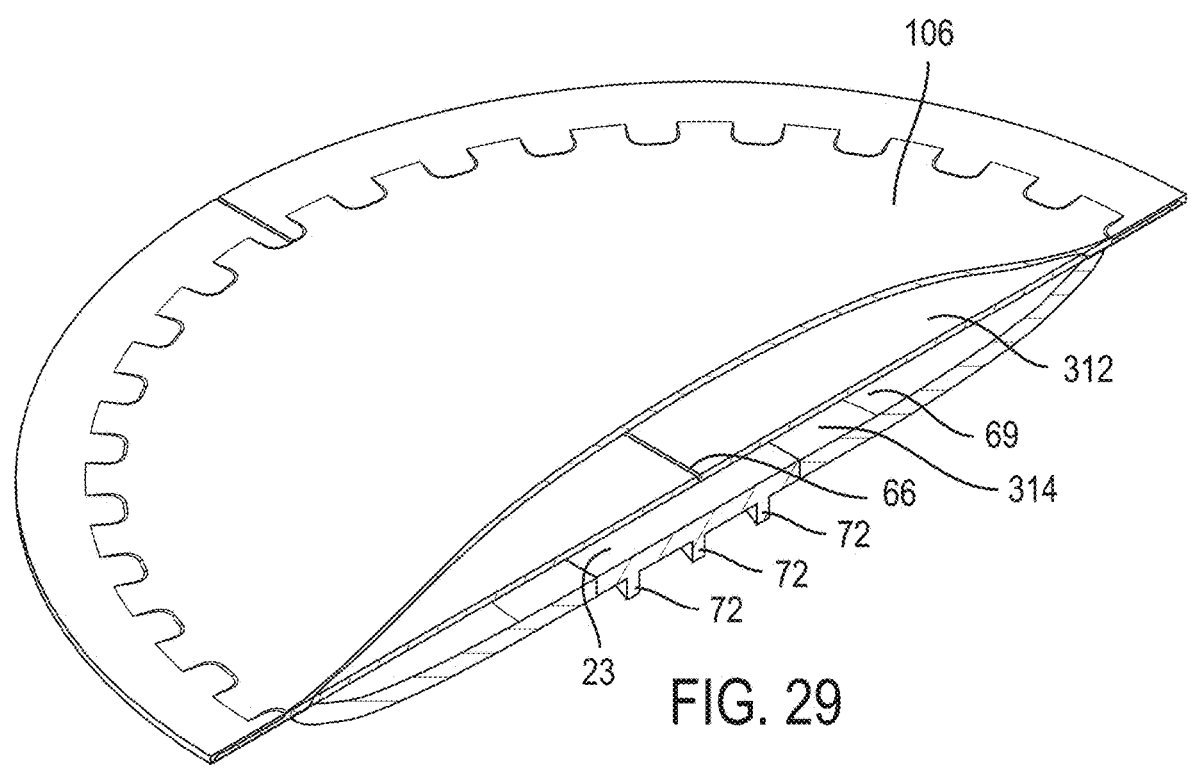
FIG. 29 depicts a perspective cross-sectional view of the example reservoir assembly of FIG. 28.

Referring now to FIGS. 28 and 29, an example embodiment of a reservoir assembly 310 is depicted. The reservoir assembly 310 may include a reservoir 12, a sharp bearing body 23 (though alternatively an outlet portion 68 may be included), a collar element 69, and a delivery sharp cover 94 (see, e.g., FIG. 10). The reservoir 12 may include a first portion and a second portion which are coupled together to enclose a sealed interior volume which may be filled with medical agent. In the example embodiment, the first portion is depicted as a liner 106. The second portion is shown as a sheet of film 312.

The sheet of film 312 may include a weakened portion. In the example, the sheet of film 312 includes scoring 66 in an "X" pattern. As mentioned elsewhere, the scoring 66 pattern may differ. Any scoring 66 pattern mentioned herein may be used. The scoring 66 may be created in a material removal process such as via laser ablation. The scoring 66 may be provided in an interior facing side of the sheet of film 312.

The collar element 69 of the reservoir assembly 310 may be coupled to the sheet of film 312 via a weld, adhesive, or in any other suitable manner. Thus, as best shown in FIG. 29, the reservoir assembly 310 may include a dry compartment 314 defined by an interior face of the collar element 69 and a face of the sheet of film 312 when the sheet of film 312 is in an intact state. With the film in the intact state, the sharp bearing body 23 may be in communication with the dry compartment 314, but isolated from the interior volume of the reservoir 12 by the sheet of material 312. The dry compartment 314 may be sealed due to the presence of the delivery sharp cover 94 (see, e.g., FIG. 10). Reservoir assemblies 310 may be provided in this state for assembly into a delivery device 10. Once a reservoir assembly 310 is assembled into a delivery device 10 and the delivery device 10 is applied to a user, pressure may be applied to the reservoir 12 (e.g. manually, via a force generating member 280, etc.) to rupture the sheet of film 312. This may place the sharp bearing body 23 into communication with the contents of the reservoir 12 and allow for delivery of fluid from the reservoir assembly 310.

Such a reservoir assembly 310 may be desirable for a variety of reasons. For example, the reservoir assembly 310 may be a self-contained component which may be manufactured in a controlled environment. As reservoir assembly 310 is sealed from the surrounding environment, the other components of the delivery device 10 may be manufactured an uncontrolled or less stringently controlled environment. This may increase ease of manufacture for a delivery device 10. Additionally, in certain embodiments, the reservoir assembly 310 may be placed into a delivery device 10 shortly prior to use. For instance, assembly of delivery devices 10 may be completed at a pharmacy, clinic, vaccination site, or by an end user. In such examples, the reservoir assembly 310 may be the only component which is distributed and stored via a cold chain. As the reservoir assembly 310 is smaller than the entire delivery device 10, this may ease strain on cold chain distribution systems during a mass vaccination campaign or in areas with less robust cold chain infrastructure.

Figure 30:
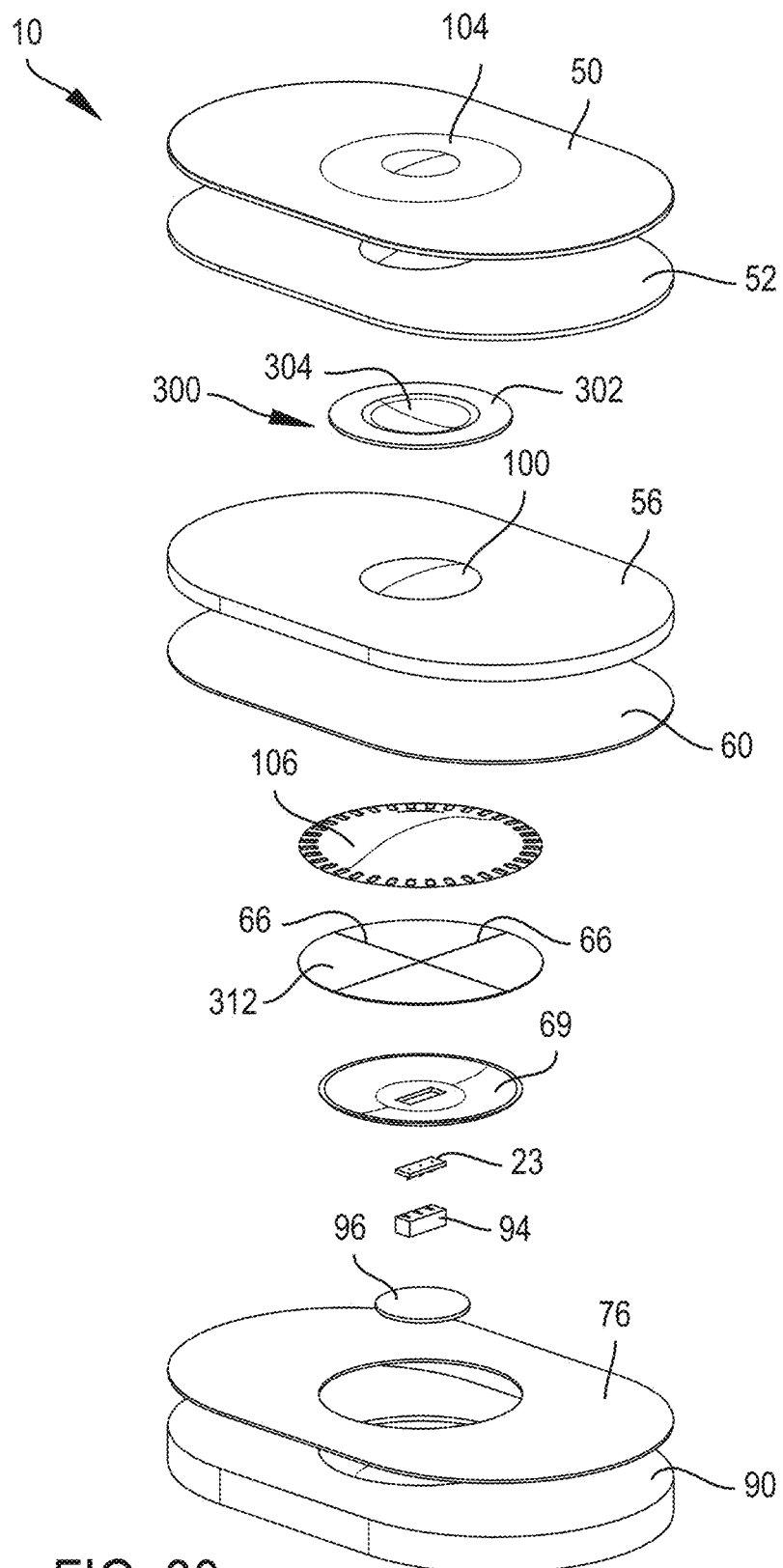
FIG. 30 depicts an exploded view of another exemplary delivery device.
Figure 31:
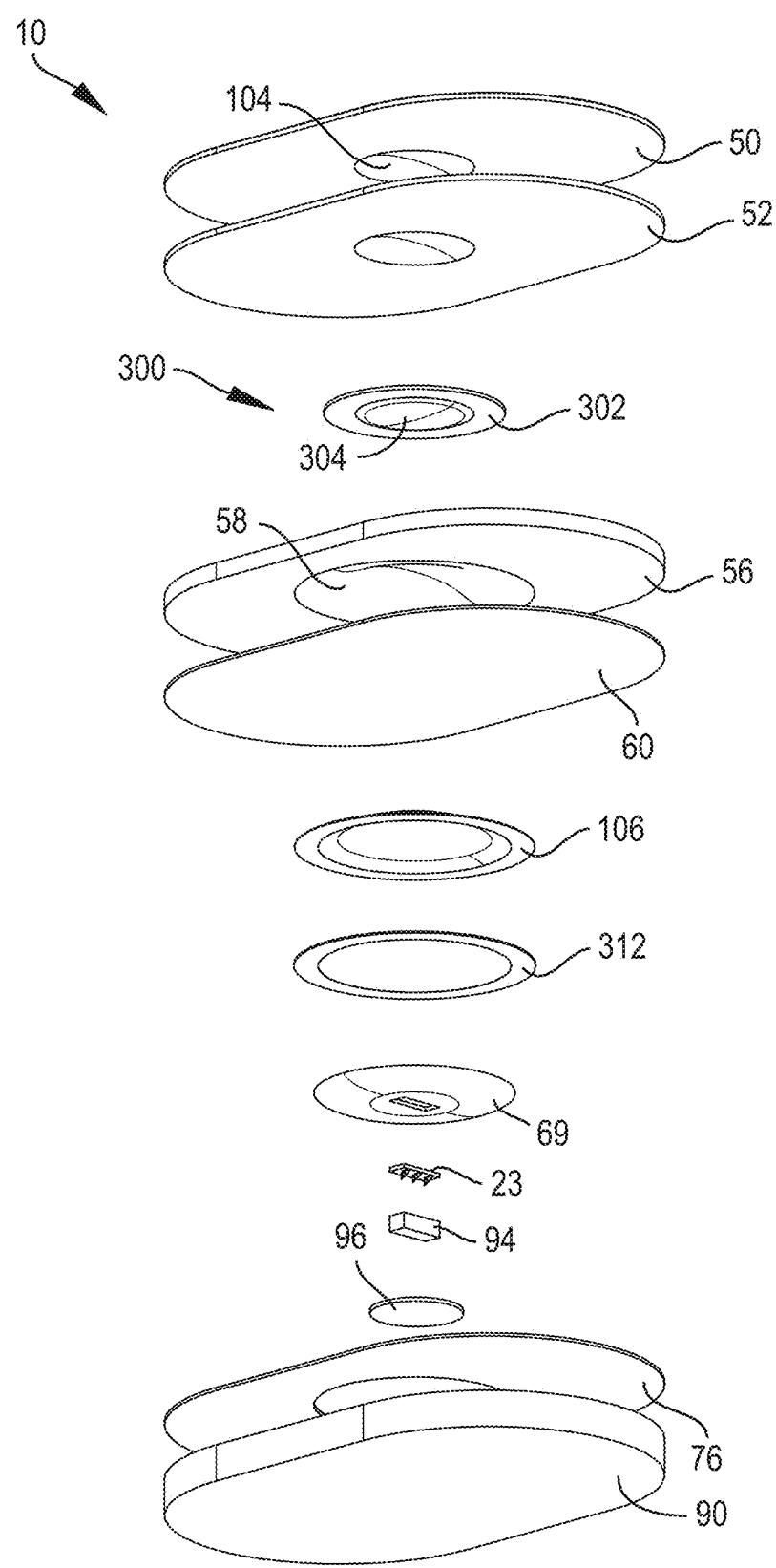
FIG. 31 depicts another exploded view of the delivery device of FIG. 30.
Figure 32:
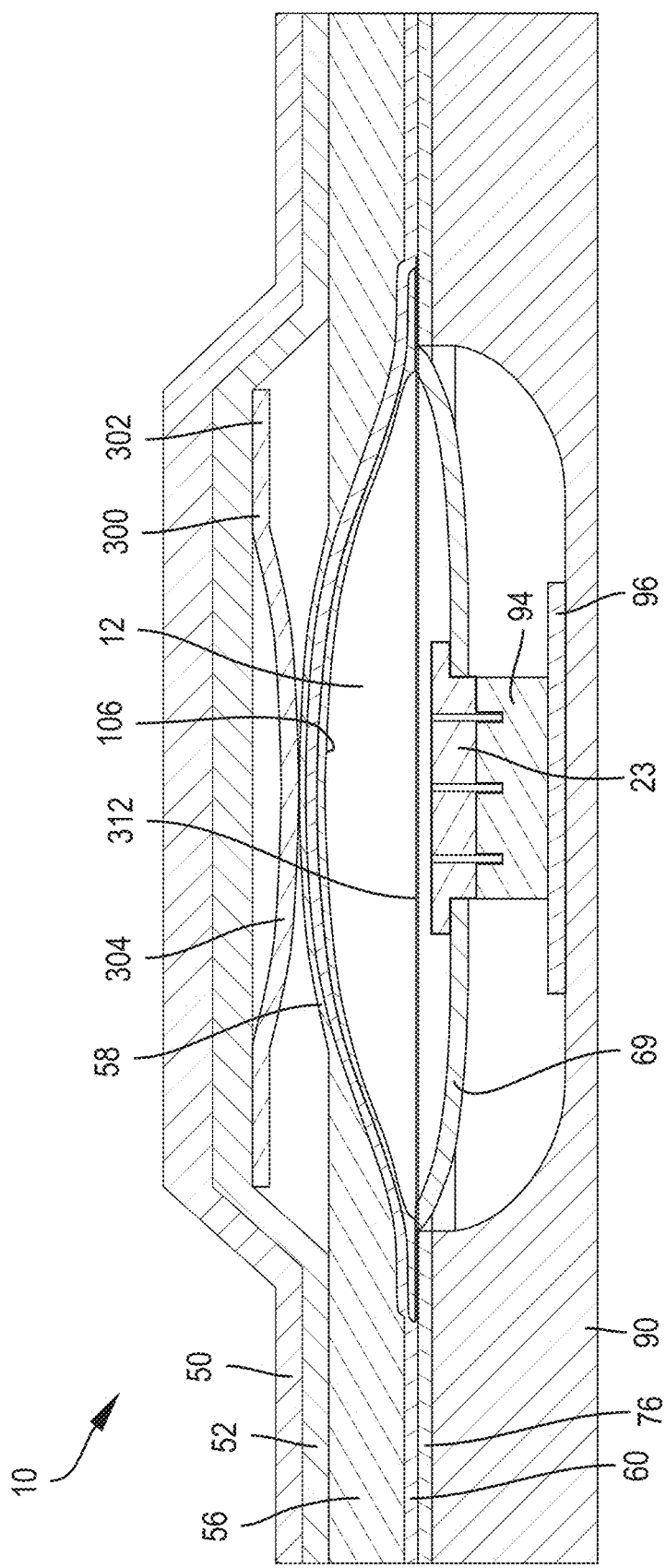
FIG. 32 depicts a cross-sectional view of an example delivery device.

Referring now to FIGS. 30-32, an alternative embodiment of the delivery device 10 shown in FIGS. 22-27 is depicted. No third layer 62 is included in the delivery device 10 of FIGS. 30-32. Instead, in this alternative embodiment, the delivery device 10 includes the reservoir 12 described in relation to FIGS. 28 and 29. The delivery device 10 shown in FIGS. 30-32 also includes a spacer element 300.

The spacer element 300 may be a projecting member which extends from the first layer 50 of the delivery device 10 towards the reservoir 12. The spacer element 300 may be substantially rigid and non-compliant. The spacer element 300 may be aligned (e.g. coaxial with a center of the reservoir 12) with the reservoir 12 and may be disposed between the outer layer 50 of the delivery device 10 and the second layer 56 of the delivery device 10. In the example embodiment shown in FIGS. 30-32, the spacer element 300 is shown in abutment with a wall of the reservoir cavity 58 and is placed such that at least a portion of the spacer element 300 is adjacent the raised section 100 of the second layer 56. As best shown in FIG. 32 (a cross-section of the delivery device 10 taken at a mid-plane of the delivery device 10), when the delivery device 10 is in the storage state, the spacer element 300 may lift the outer layer 50 such that the raised area 104 of the outer layer 50 is not in contact with the raised section 100 of the second layer 56. As the outer layer 50 may be flat in an unstressed state, the outer layer 50 may be stretched to accommodate the spacer element 300 between the outer layer 50 and the second layer 56. This may cause a bias or restoring force to be stored in the outer layer 50. Spacer elements 300 may also be included in other delivery devices 10 shown and described herein. For example, in some embodiments a spacer element 300 may be included between the elastomeric sheet 20 and reservoir 12 of the delivery device 10 shown in FIG. 1.

The spacer element 300 may concentrate restoring force exerted by the outer layer 50 onto the reservoir 12 and may be referred to herein as a force concentrator. The geometry of the spacer element 300 may be selected to direct force from the stretched outer layer 50 onto the reservoir 12. For example, the spacer element 300 may be rounded and may have a convex portion which extends toward the reservoir 12. In certain examples, and as depicted, the spacer element 300 may be a concavo-convex in at least a region 304 of the spacer element 300. The convex surface of the spacer element 300 may extend outward in the direction of the reservoir 12. The opposing concave surface of the spacer element 300 may act as a thumb depression. Thus, in embodiments where manual pressure is applied to rupture the reservoir 12, the concave side of the spacer element 300 may help to center the user's finger over the reservoir 12 as pressure is applied. A flange 302 may surround the concavo-convex portion of the spacer element 300. The flange 302 may provide a surface to which adhesive 52 of the outer layer 50 may bond. Additionally, the flange 302 may serve to enlarge the spacer element 300 and cause a larger portion of the outer layer 30 to be stretched.

Figure 33:
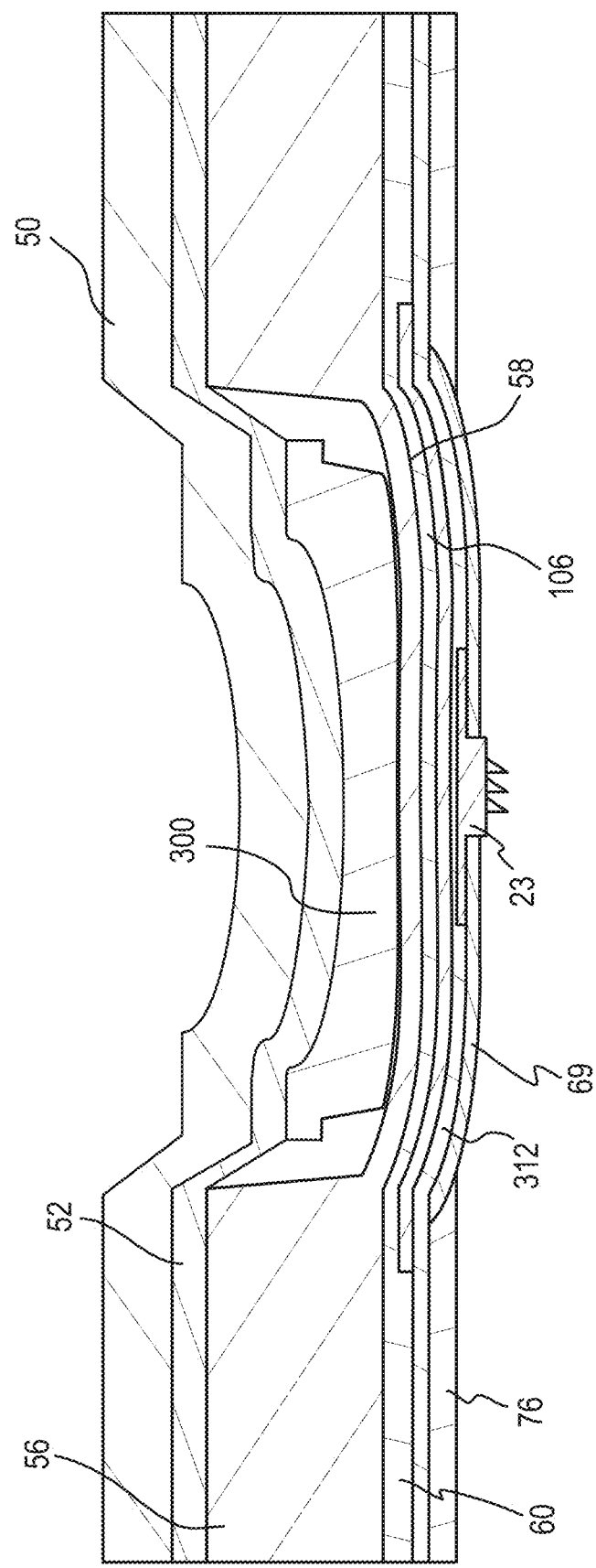
FIG. 33 depicts a cross-sectional view of an example delivery device.

Referring now to FIG. 33, in some examples, the contour of the proximal surface of a spacer element 300 may roughly mimic the contour of the distal surface of the collar element 69, but may be a smaller scale version of that surface. The wall of the reservoir cavity 58 and the wall of the reservoir 12 (in this embodiment formed by a liner 106 and reservoir film 312) may be flexible. Thus, as the spacer element 300 is displaced toward the collar element 69, the spacer element 300 may cause the reservoir 12 to collapse and press the walls of the reservoir 12 and reservoir cavity 58 against the collar element 69. Due to the similar contours of the collar element 69 and spacer element 300, the walls of the reservoir and reservoir cavity 58 may conform to the shape of the collar element 69 as the reservoir 12 is collapsed. When fully delivered, the collar element 69, collapsed reservoir 12, wall of the reservoir cavity 58, and spacer element 300 may be in a nested state with each closely seated inside one another. This may help to ensure that the reservoir 12 is completely emptied when the delivery device 10 is used.

Figure 34:
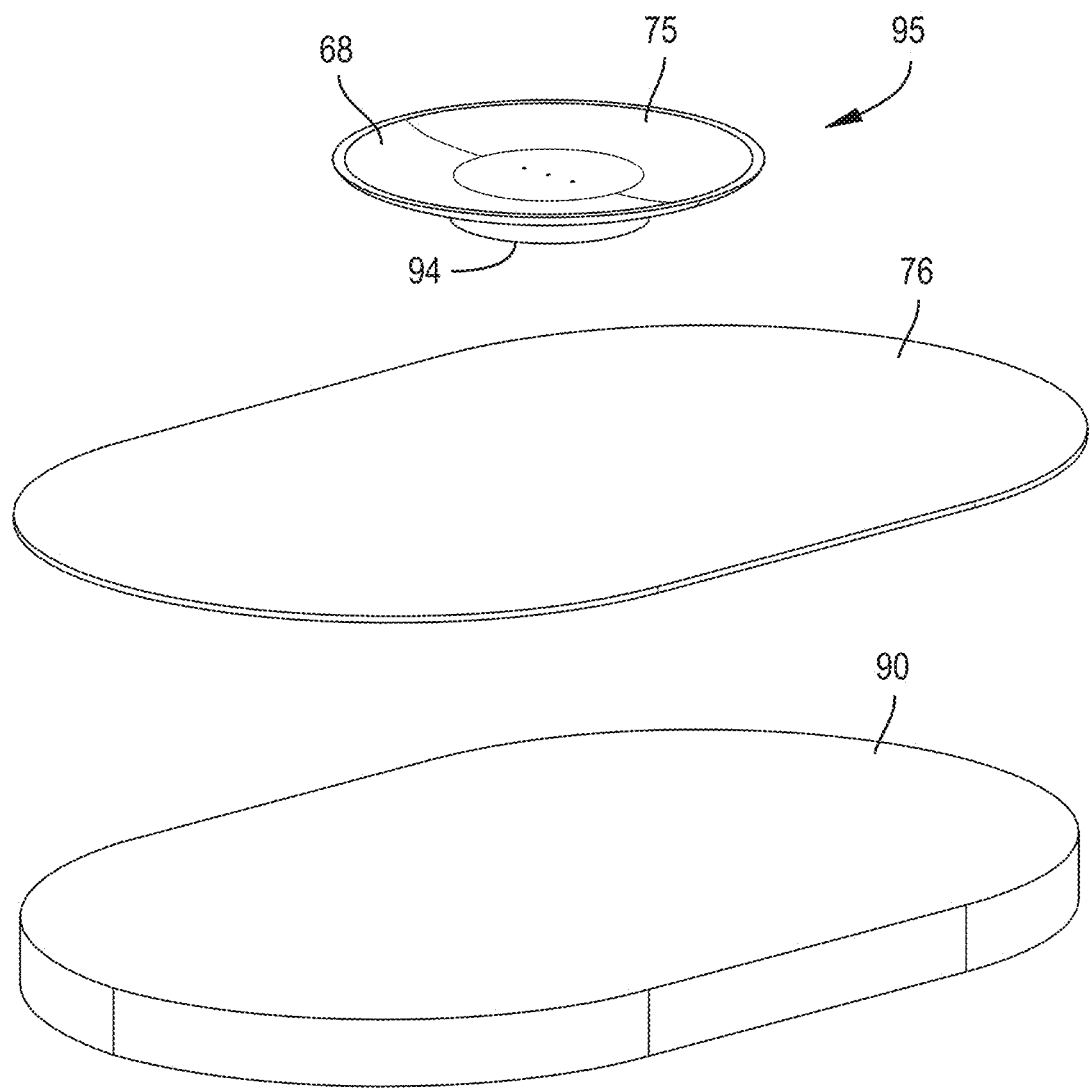
FIG. 34 depicts an exploded view of a portion of an example delivery device.
Figure 35:
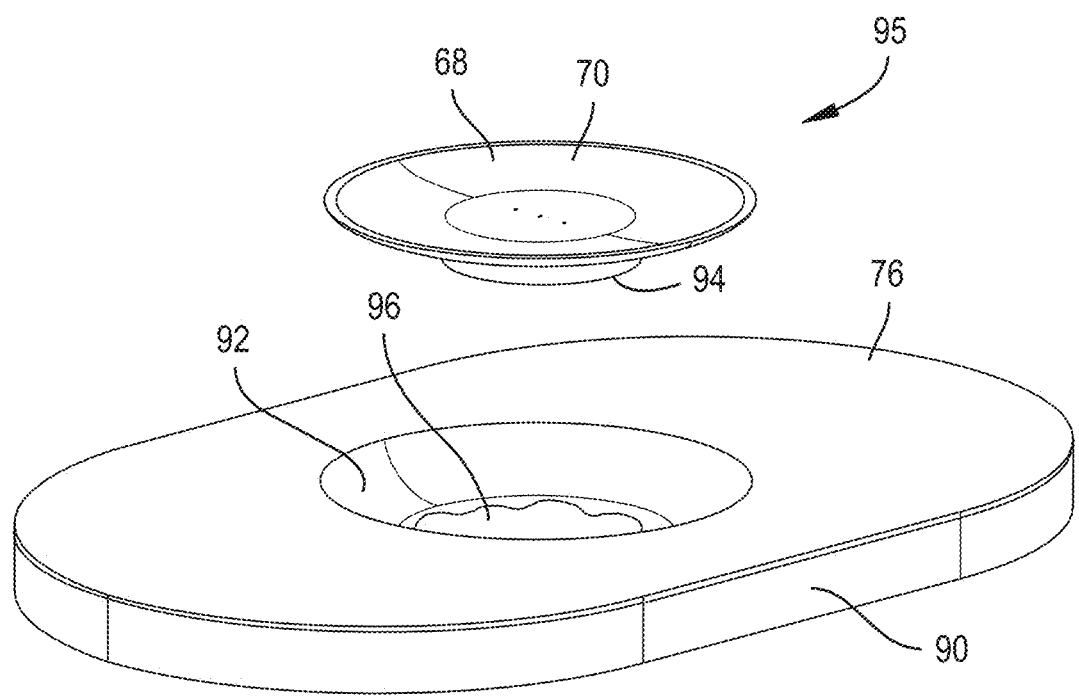
FIG. 35 depicts another exploded view of a portion of an example delivery device.
Figure 36:
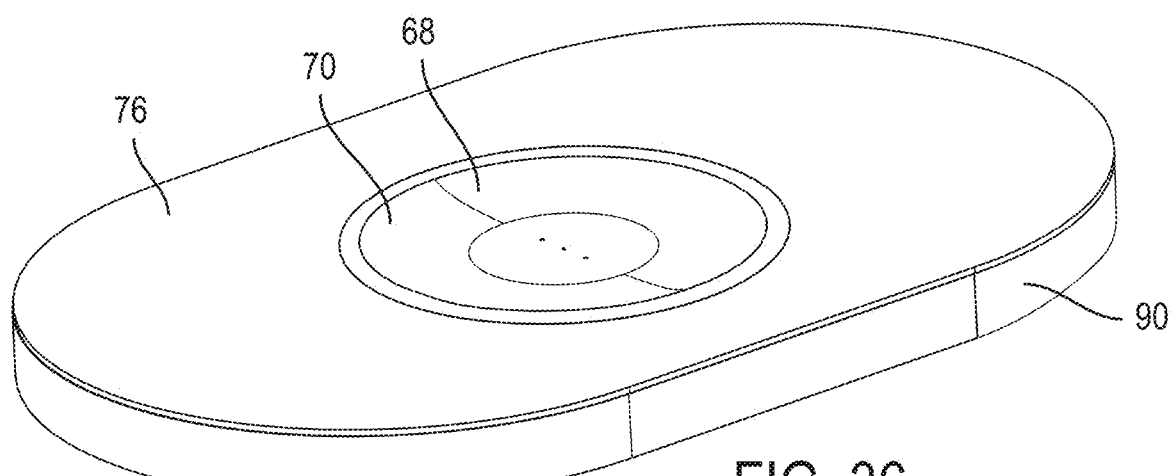
FIG. 36 depicts an assembled view of a portion of an example delivery device.

Referring now to FIGS. 34-36, to assemble a delivery device 10 such as that shown in FIG. 10, FIGS. 23-27, or FIG. 30-32 a layer of adhesive 76 may be applied over a face of the release liner 90. The recess 92 may then be formed into the liner 90 and adhesive 76. An outlet portion 68 may be formed and the delivery sharp cover 94 may be installed over the delivery sharp(s) 72 of the outlet portion 68. The outlet portion 68 and delivery sharp cover 94 may be collectively referred to as a protected outlet assembly 95. The protected outlet assembly 95 may be installed into the recess 92 in the release liner 90. This may be accomplished by dispensing or otherwise depositing a volume of adhesive 96 into the recess 92. The protected outlet assembly 95 may then be introduced into the recess 92 such that the delivery sharp cover 94 is adhered into place within the recess 92 via the adhesive 96. The protected outlet assembly 95 may be placed into the into the recess 92 of the release liner 90 via a pick and place operation.

The laminate of the first, second, and third layers 50, 56, 62 and filled reservoir 12 may be coupled to the release liner 90 via the adhesive 76 to form the complete delivery device 10 (see, e.g. FIG. 26). Additional adhesive may couple and fluidically seal the stiffener section 75 of the outlet portion 68 to the third layer 62 so as to inhibit leakage. In alternative embodiments, a collar element 69 (see, e.g., FIG. 14) which surrounds the outlet portion 68 may additionally be sealed to the third layer 62 via adhesive.

In embodiments where the reservoir 12 is constructed as a separate component, the delivery sharp cover 94 of the reservoir 12 may be placed into the recess 92 and adhered into place via the adhesive 96. The side of the reservoir 12 opposite the delivery sharp cover 94 may be coupled into the reservoir cavity 58 via adhesive 60. The third layer 62 may be omitted. Alternatively, where a portion of the third layer 62 forms a part of the reservoir 12, the third layer 62 may be coupled into place against the second layer 56 when the reservoir 12 is adhered into the reservoir cavity 58. Similarly, where a reservoir assembly 310 such as that shown in FIG. 29 is included, the delivery sharp cover 94 may be adhered into the recess 92 of the release liner 90 via adhesive 96. The liner 106 of the reservoir 12 may be adhered into place within the reservoir cavity 58 as the other layers are assembled into place.

Figure 37:
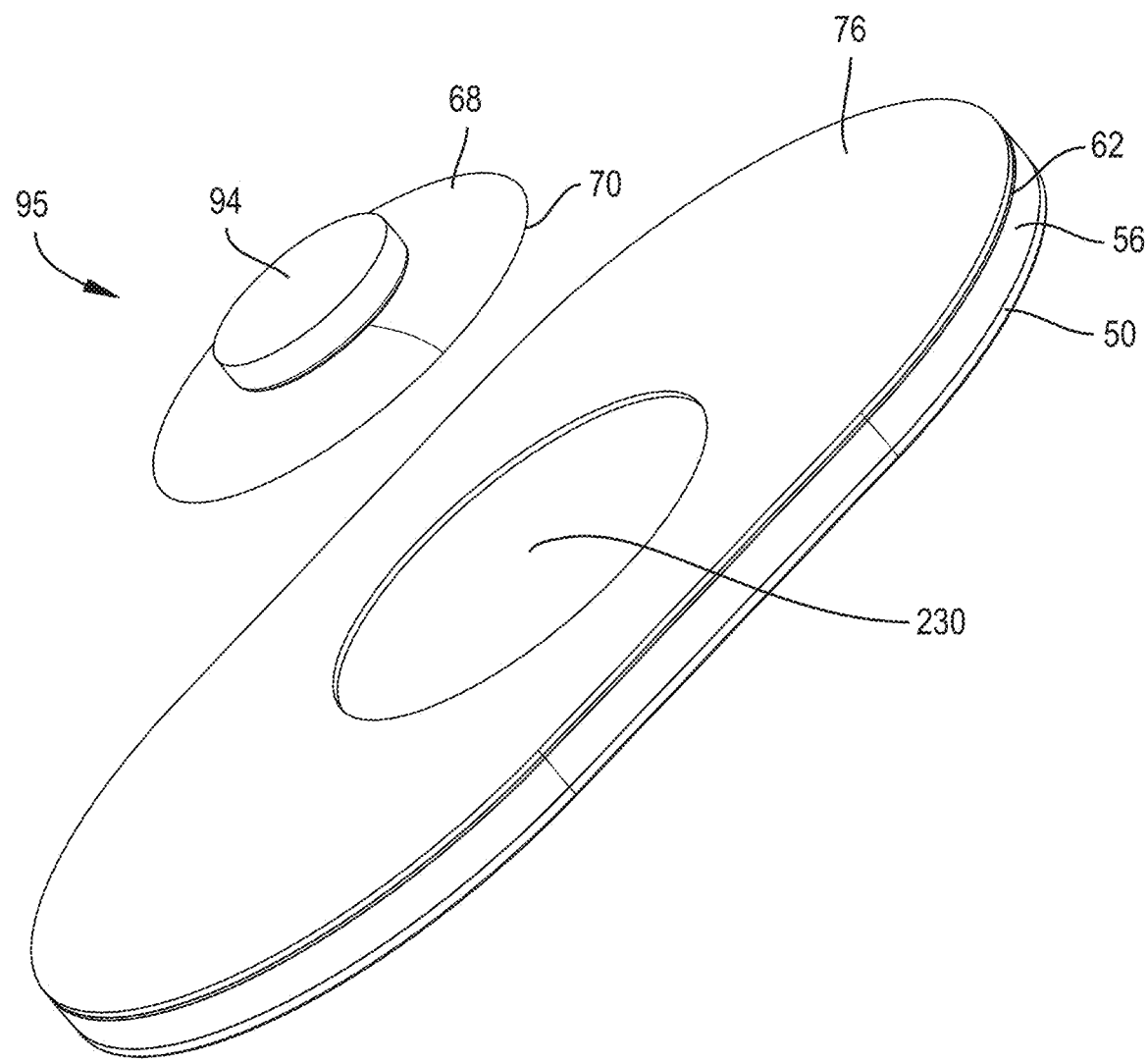
FIG. 37 depicts an exploded view of a portion of an example delivery device.

In alternative embodiments, and referring now to FIG. 37, a recess 230 or receptacle for the outlet portion 68 which accepts a portion of the manifold section 70 of the outlet portion 68 may be included. This receptacle 230 may, for example, be created as a feature of the second layer 56 similarly to the reservoir cavity 58. In certain examples, the receptacle 230 may be created in the same embossing operation that creates the reservoir cavity 58. The third layer 62 may be sufficiently flexible to conform to the shape of the receptacle 230 so as to allow the stiffener section 75 to be seated into the receptacle 230 over the third layer 62. The outlet portion 68 may be retained in place on the delivery device 10 via adhesive 76 which may be applied over the surface of the third layer 62. The outlet portion 68 may be assembled into the receptacle 230 via a pick and place operation.

Figure 38:
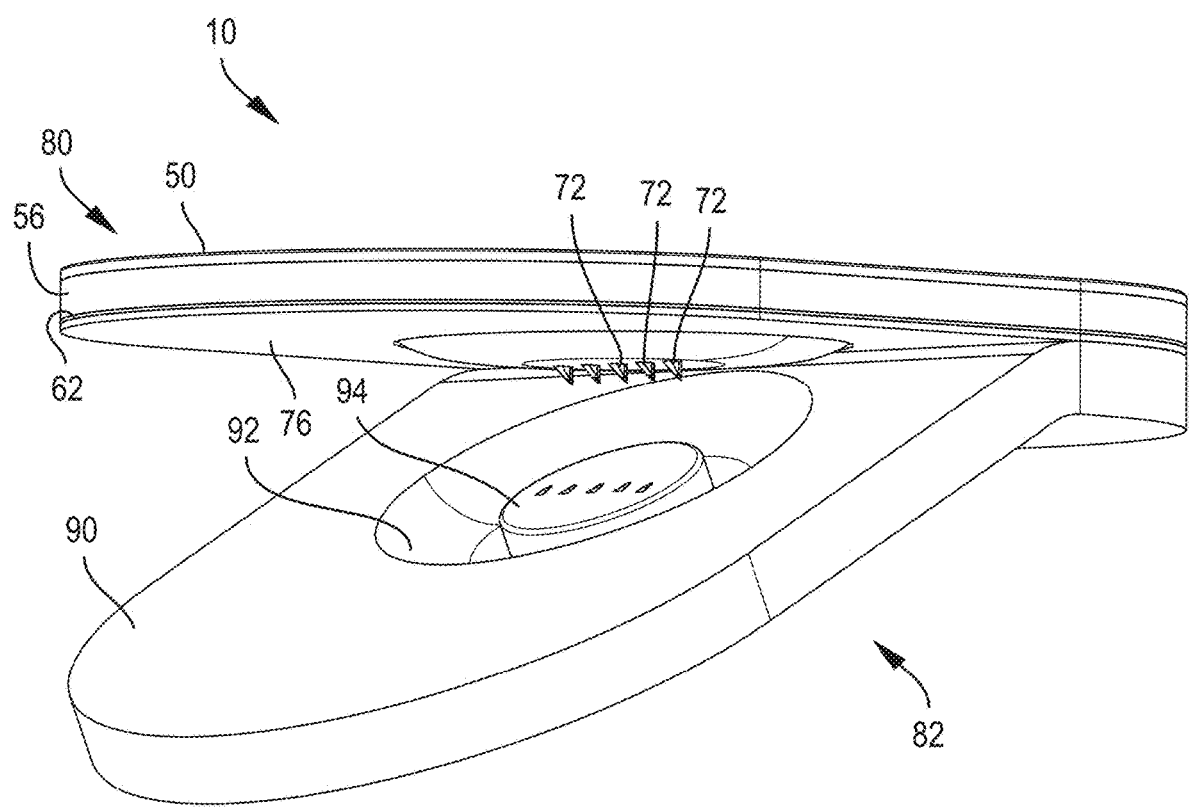
FIG. 38 depicts a view of an example delivery device in which a second portion of the delivery device is being peeled off of a first portion of the delivery device.

Referring now to FIG. 38, when the release liner 90 is peeled from the delivery device 10 as shown in FIG. 38, the delivery sharp cover 94 may be removed together with release liner 90. This may occur because the delivery sharp cover 94 is formed of a lower tack adhesive than the adhesive 96 used to couple the delivery sharp cover 94 into the recess 92 in the release liner 90. Thus, via a single interaction with the delivery device 10, the entire second portion 82 of the delivery device 10 may be removed. This may in turn render the delivery device 10 ready for application to the skin of a patient.

Figure 39:
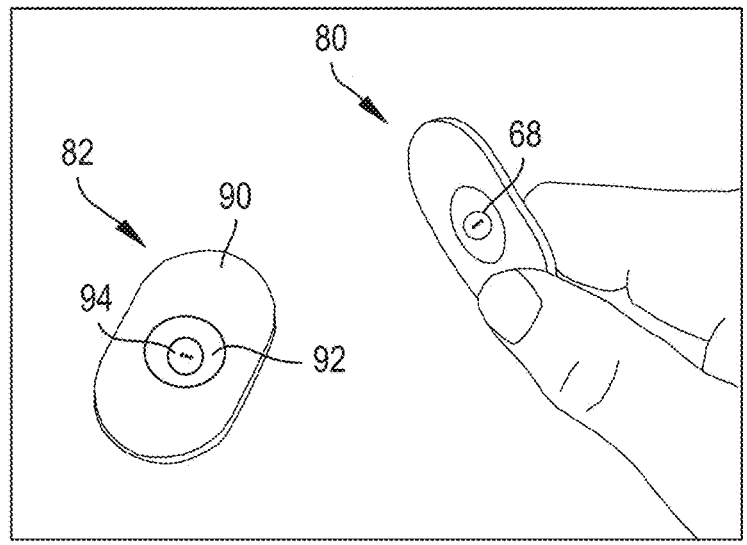
FIG. 39 depicts a view of an exemplary delivery device in which a first portion of the delivery device has been separated from a second portion of the delivery device.

Still referring to FIG. 38, although the adhesive 76 may be initially be applied to the release liner 90, the adhesive 76 may not be removed along with the release liner 90. Instead, the adhesive 76 may remain attached to the third layer 62 of the first portion 80 such that the first portion 80 may be adhered in place at the infusion site. This may be because the peel strength between the adhesive 76 and the film 62 may be selected to be greater than the peel strength between the adhesive 76 and the release liner 90. The release liner 90 and delivery sharp cover 94 are shown separated from the remainder of an example delivery device 10 in FIG. 39.

Figure 40:
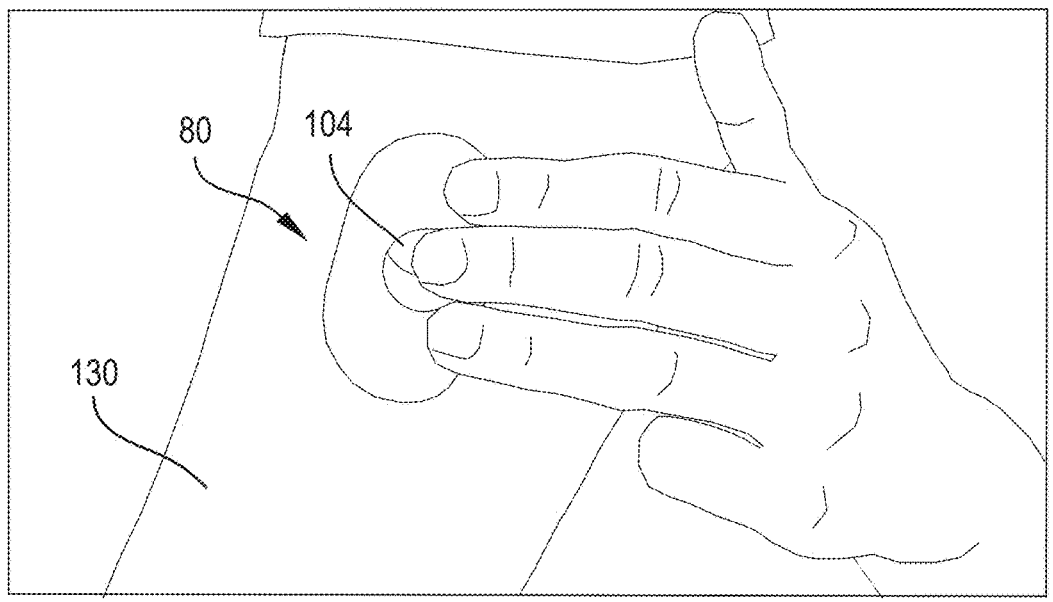
FIG. 40 depicts a view of an example delivery device in place on an infusion site of a patient.

Referring now to FIG. 40, once the second portion 82 or cover assembly has been removed, the first portion 80 of the delivery device 10 may be applied to an infusion site. In the example shown in FIG. 40, the infusion site is shown as an upper arm 130 of a patient. Though an upper arm 130 is shown, delivery devices 10 including microneedles may be used over a wide variety of infusion sites as the injection may be provided into shallow tissue. Thus, where the delivery device 10 contains a vaccine, injection via the delivery device 10 may be given at almost any desired location on the body of a patient instead of being limited to typical vaccination sites such as the upper arm, thigh, buttock, etc.

Figure 41:
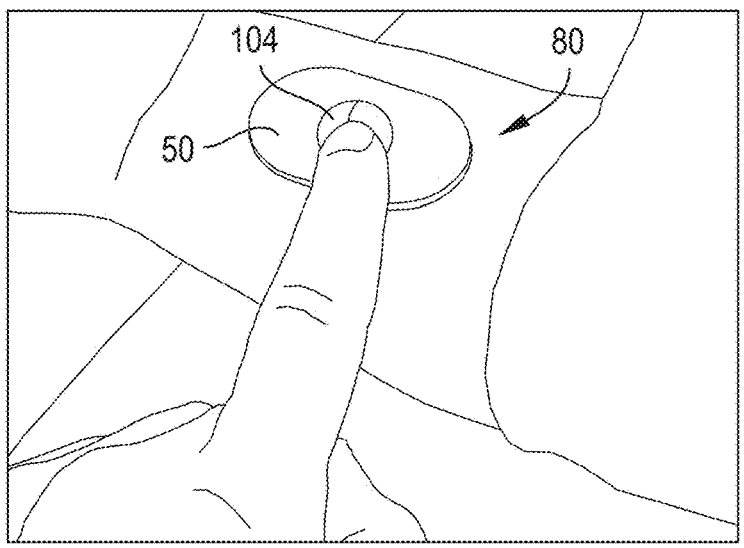
FIG. 41 depicts a view of an example delivery device in place on an infusion site in which as user is applying manual pressure to a portion of the delivery device.

Referring now to FIG. 41, once the first portion 80 of a delivery device 10 has been adhered at the injection site, a user may depress the raised area 104 on the outer layer 50 of the delivery device 10. This may exert a force on the reservoir portion 116 (see, e.g. FIG. 25) of the third layer 62 of the delivery device 10 which may cause the reservoir portion 116 to rupture at the location of the score line 120 (see, e.g., FIG. 27). This may establish a fluid flow path from the delivery sharp(s) 72 to the agent contained within the reservoir 12 of the delivery device 10. Additionally, pressure exerted on the raised area 104 may also cause the delivery sharp(s) 72 of delivery device 10 to be pressed into the injection site and into communication with the target delivery destination in the patient. To ensure that the volume of agent loaded into the reservoir 12 (see, e.g., FIG. 26) is administered, the user may continue to exert pressure against the raised area 104. This may urge agent contained in the reservoir 12 to be evacuated from the delivery device 10 and deposited into the patient via the delivery sharp(s) 72.

Pressure may be applied to the raised area for a prescribed period of time (e.g. 1-5 minutes). The period of time may depend on the length and cross sectional area of the flow lumen 126 (see, e.g., FIG. 26) of each of the at least one delivery sharp 72 (see, e.g., FIG. 26) included in the delivery device 10 and/or length and cross sectional area of the flow paths 124 (see, e.g., FIG. 26) included in the outlet portion 68 (see, e.g., FIG. 26). The period of time may also depend on the number of delivery sharps 72 included in the delivery device 10. Preferably, the period of time may be selected such that the volume contained in the reservoir 12 is substantially entirely expelled from the delivery device 10 into the patient. In alternative embodiments, manual pressure need not be applied for the entire time period. In such embodiments, manual pressure may be applied to transition the delivery device to an active state (e.g. break the reservoir 12 at one or more score line 120). The outer layer 50 of the delivery device 10 may be elastic and may drive fluid out of the reservoir 12 as it restores from a stressed state to a more relaxed state.

Figure 42:
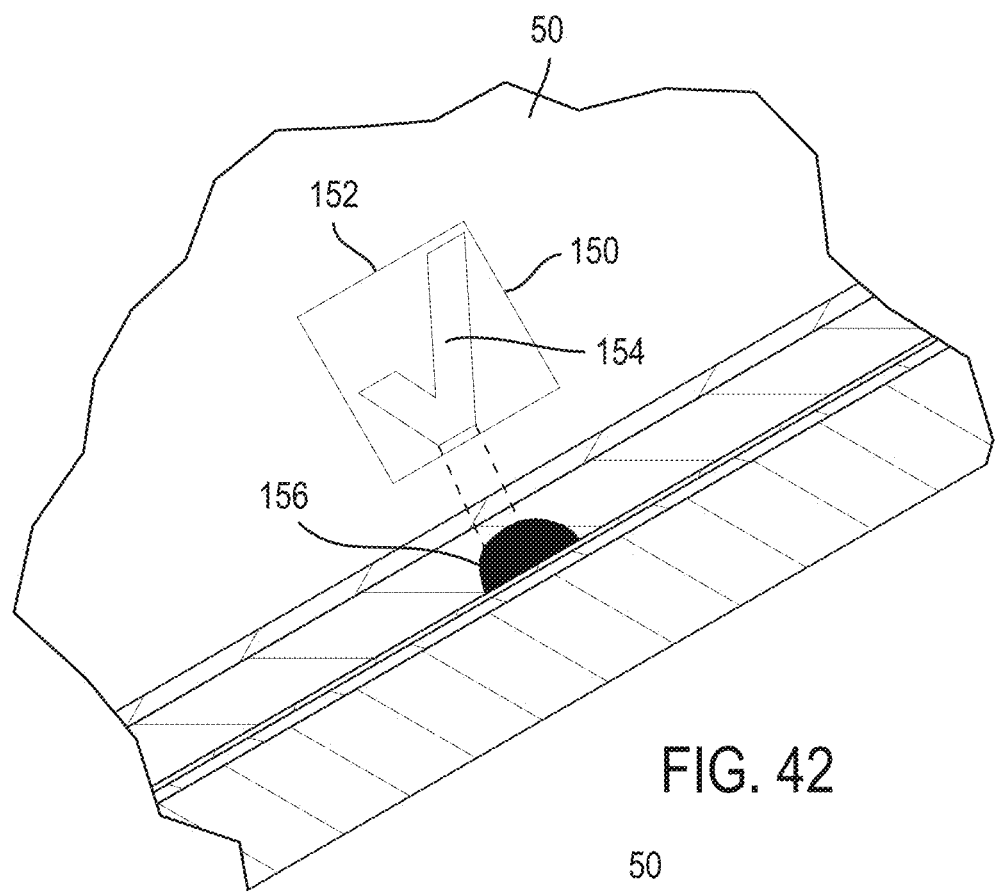
FIG. 42 depicts a cross-sectional view of an example delivery device including an indicator reservoir.
Figure 43:
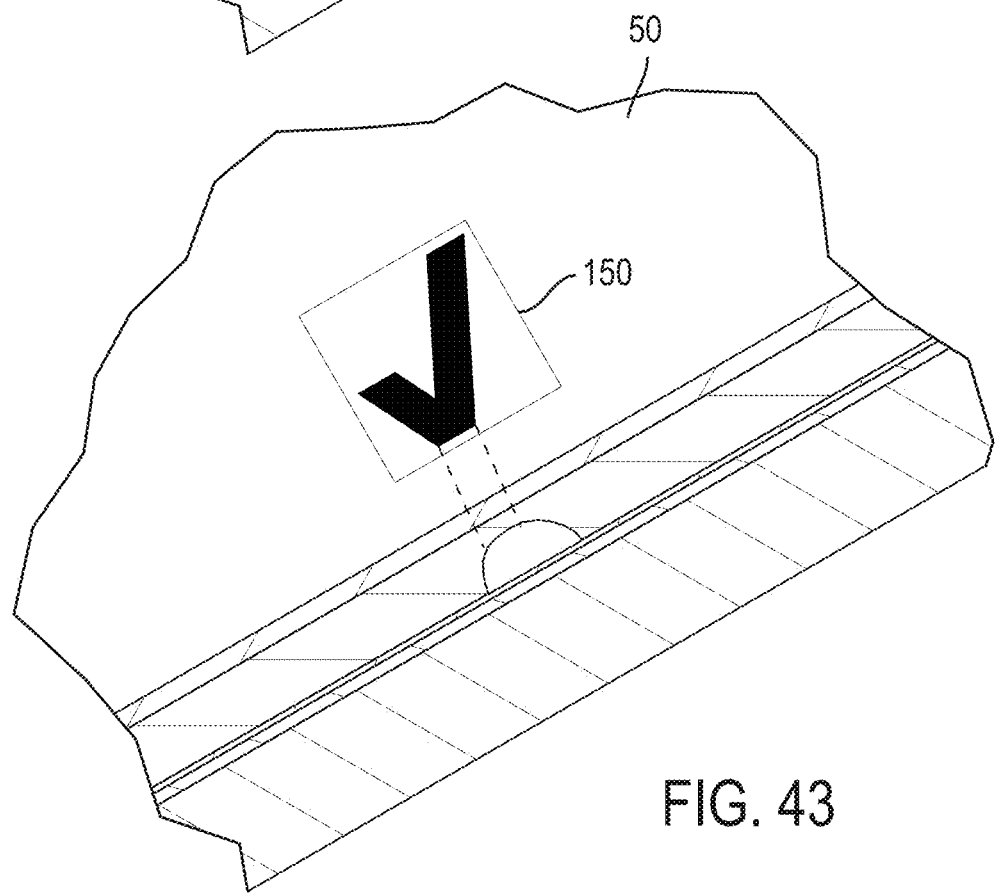
FIG. 43 depicts a cross-sectional view of an example delivery device including an indicator reservoir.

Referring now to FIGS. 42-43, some delivery devices 10 may include one or more indicator 150. The indicator 150 may be altered during usage of the delivery device 10 so as to provide feedback to a user that the infusion is proceeding in a prescribed manner. In some embodiments, the indicator 150 may be irreversibly altered during use. Thus, after use, a delivery device 10 may clearly convey to a user that the delivery device 10 has been previously used. In the example embodiment depicted in FIGS. 42-43, the indicator 150 includes a window 152 which may be included in the outer layer 50 of the delivery device 10. The window 152 may provide an aperture through which an indicium 154 included as part of the second layer 56 may be viewed. The delivery device 10 may also include an indicator reservoir 156 which may be defined between the second and third layers 56, 62. The indicator reservoir 156 may contain an indicator medium such as a colorant or dye. When a user presses down on the raised area 104 of a delivery device 10 to rupture an agent filled reservoir 12 (see, e.g., FIG. 26), the force applied to the delivery device 10 may also cause rupture of the indicator reservoir 156. There may be a channel included in the delivery device 10 to establish fluid communication between the indicator reservoir 156 and indicium 154. As shown in FIG. 43, once the indicator reservoir 156 is ruptured, the indicator medium may flow to the indicium 154. This may cause a visibly perceptible change in the indicium 154. The indicator medium may, for example, color the indicium 154. In some embodiments, the indicator medium may be a dark dye which may irreversibly alter the indicium 154 of the indicator 150. Thus, the indicator 150 may be altered in an indication that the reservoir 12 of the delivery device 10 has been ruptured and the delivery device 10 has been used. Thus, the indicator 150 may be a reservoir 12 access indicator.

In an alternative embodiment, the indicium 154 of the indicator 150 may include a material which has chromic properties such as a luecodye or pH indicator though materials with other types of chromism may be used. Using the example of a halochromic material for non-limiting illustrative purposes, the indicium 154 may be colorless prior to use of a delivery device 10. The indicator reservoir 156 may be filled with a change agent. In certain examples, the change agent may include a low or high pH fluid. When the indicator reservoir 156 is ruptured, the change agent may come into communication with the halochromic material of the indicium 154. This may result in a color change of the indicium 154 from a colorless state to a colored state (or from a first colored state to second colored state different from the first). For example, the halochromic material may include crystal violet lactone, phenolphthalein, thymolphthalein, etc.

Figure 44:
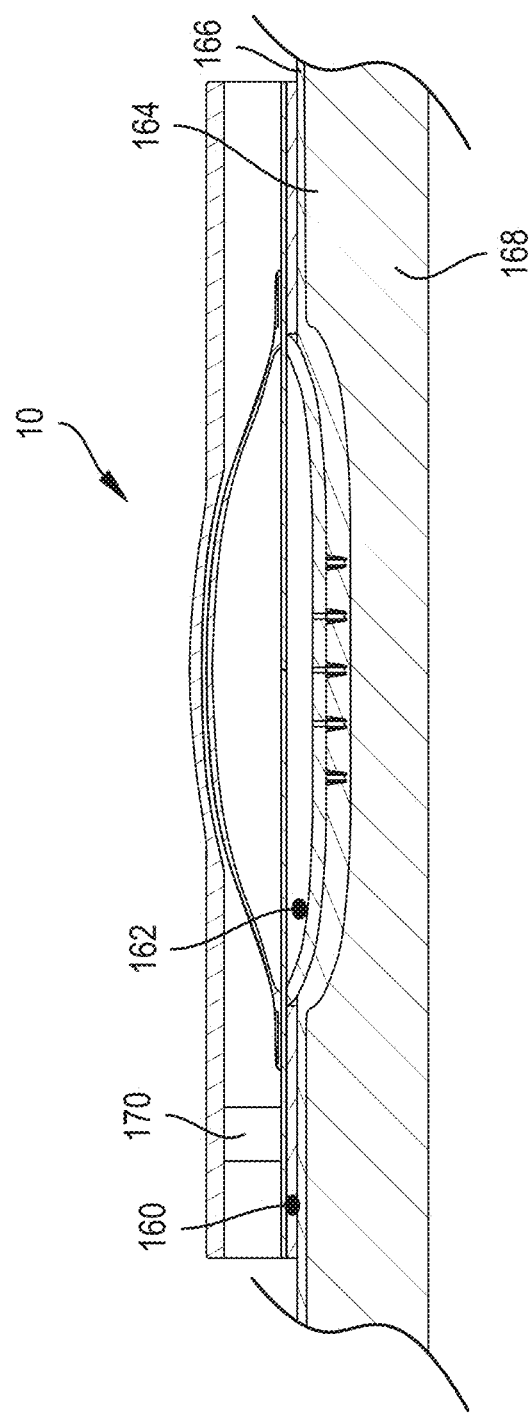
FIG. 44 depicts a cross-sectional view of an example delivery device applied to an injection site.
Figure 45:
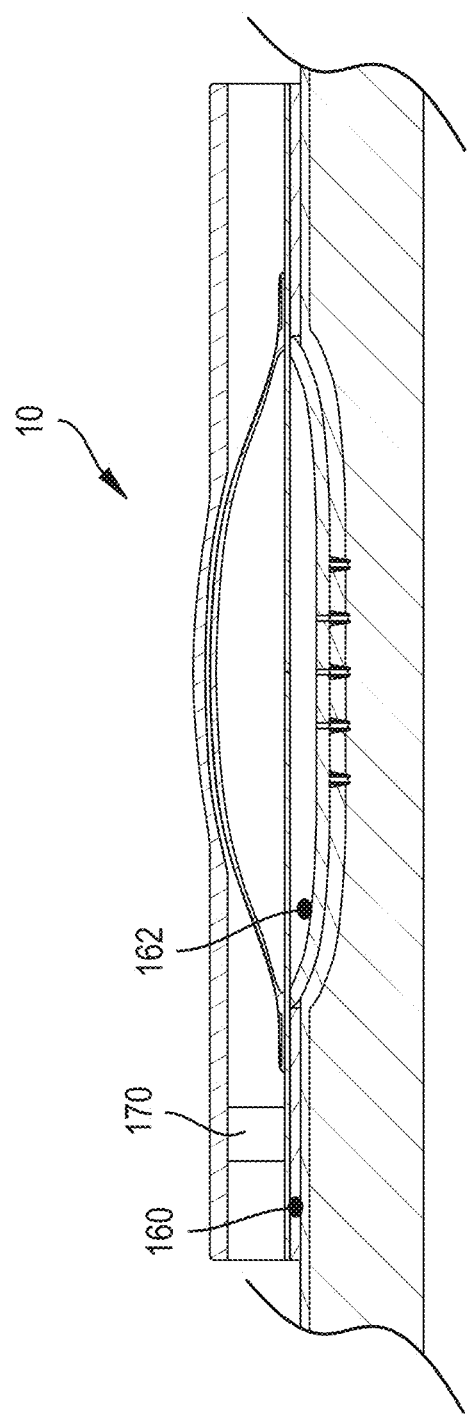
FIG. 45 depicts another cross-sectional view of an example delivery device applied to an injection site.

Referring now to FIGS. 44-45, a delivery device 10 may include a puncture depth indicator. This may be in place of or in addition to the indicator 150 described above in relation to FIGS. 42-43. In such examples, the puncture depth indicator may include a circuit with a first electrode 160 and second electrode 162 as well as a power source 170. The first electrode 160 may be in contact with an external surface of the skin 164. The second electrode 162 may be in contact with the outlet portion 68, a section of the outlet portion 68 including the delivery sharps 72 (e.g. a sharp bearing body 23 such as that shown in FIG. 11), or a delivery sharp 72. The skin 164 may act as a resistor which is placed between the first electrode 160 and the second electrode 162. The resistance provided by the skin 164 may differ depending on the penetration depth of the delivery sharps 72 into the skin 164. For example, in the event that the delivery sharps 72 do not penetrate into the skin 164 or penetrate into, but not through the stratum corneum 166 (see, e.g. FIG. 44), the resistance may be high. Deeper layers 168 of the skin 164 may offer a lower resistance. When the delivery sharps 72 penetrate past the stratum corneum to an intradermal location (see, e.g. FIG. 45), the resistance may be comparatively low. Via measurement circuitry, a voltage measurement between the first and second electrodes 160, 162 may be made and an indication signal may be provided via an indication generator based on the voltage. The indication signal may be audible (e.g. one or more beep emitted from a speaker), tactile (e.g. vibratory signal via a vibratory motor), or visible (e.g. illumination or one or more light emitter such as an LED). In some embodiments, an indication signal may be generated when the measurement indicates skin 164 resistance is below a threshold. This may convey to a user that the delivery sharps 72 have reached a target depth. In other embodiments, an indication signal may be changed based on the measured voltage. For example, a light emitter may illuminate a first color (e.g. red) when the measurement indicates the delivery sharps 72 are not inserted to the target depth and illuminate a second color (e.g. green) when the measurement indicates that the delivery sharps 72 have penetrated to the target depth.

Figure 46:
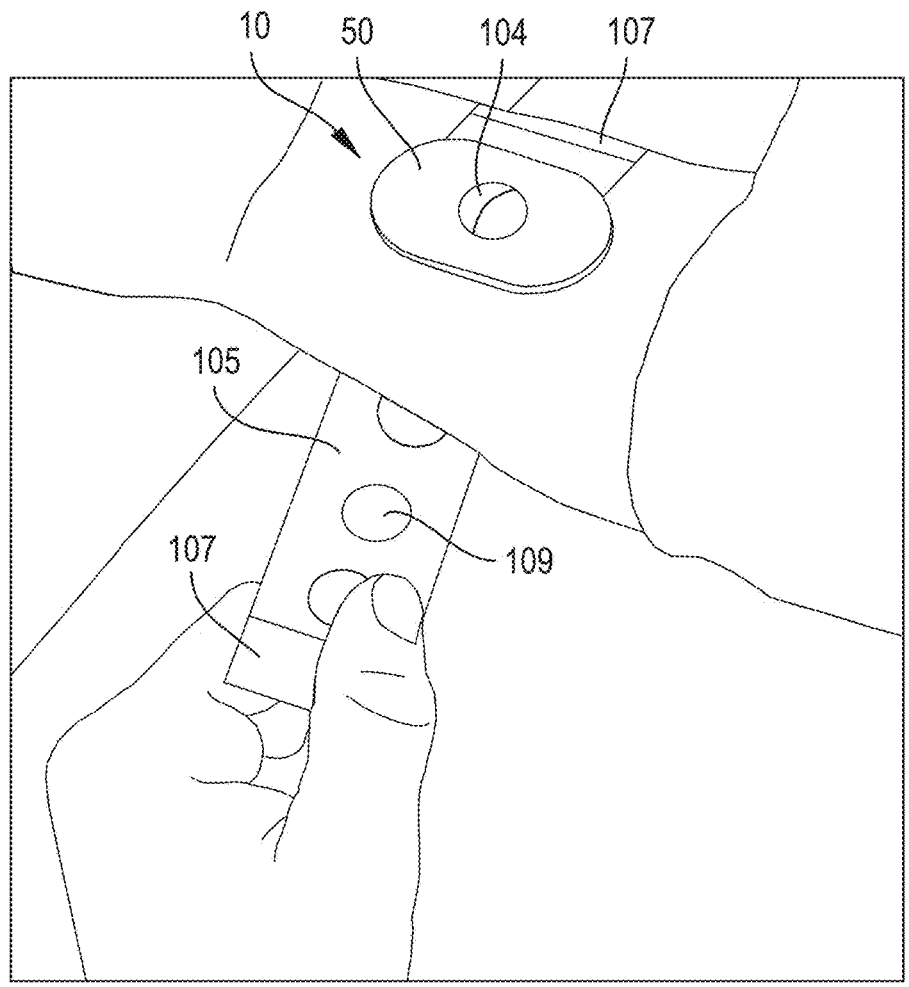
FIG. 46 depicts a view of an example delivery device including a strap where the delivery device is in place on an infusion site.

In certain examples, and referring now primarily to FIG. 46, the delivery device 10 may be arranged to apply pressure to drive agent out of the delivery device 10 and into a patient via the microneedles. This may free a user or patient from pressing against the delivery device 10 to push fluid out of the delivery device 10 and into the infusion site. As mentioned elsewhere herein, the outer layer 50 of the delivery device 10 may be constructed of a stretchable elastic material (e.g. elastic roller bandage type fabric). This raised area 104 of the outer layer 50 may be in a stretched state when fluid is contained within the delivery device 10 and may exert a bias force against the fluid. As this bias force drives agent out of the delivery device 10 the raised area 104 may restore to a less stressed state. Thus, the raised area 104 may act similarly to the elastomeric sheet 20 of FIG. 1.

Additionally, in certain examples and as shown in FIG. 46, the delivery device 10 may include a strap 105. In some embodiments, the strap 105 may be an extension or wing which projects from a side of the outer layer 50. The strap 105 may be a stretchable elastic material which may be the same as that used to form the outer layer 50. The strap 105 may be stretched and wrapped around the portion of the body (e.g. arm) where the injection site is located. This may exert a compressive force against the raised area 104 which may help to drive agent out of the delivery device 10 and into a patient.

Once wrapped around the body, an end of the strap 105 may be anchored to another portion of the strap 105 or a portion of the delivery device 10 to secure it in place. This may allow increased pressure to be exerted against agent in the delivery device 10 without sustained application of manual pressure to the raised area 104. In some embodiments, the strap 105 may include regions of cooperating fasteners 107 (e.g. hook and loop or Velcro type arrangement) to facilitate securement of the free end of the strap 105 once wrapped around the body. Clips or other fasteners may also be used. Alternatively, the strap 105 material may be a self-adhering cohesive bandage material. In such examples, fasteners 107 or clips may be omitted.

As shown in FIG. 46, the strap 105 may, in various examples, include a number of indicators 109. The indicators 109 may be spaced from one another on the strap 105 to provide a visual indication of how tightly the strap 105 should be wrapped for various patient populations. For examples, there may be indicators 109 for patients of different weights or sizes. The indicators 109 may be labeled with text, symbols, pictures, combinations thereof, etc. There may be one or more indicators 109 for children (e.g. infant, toddler, children over 50 lbs, etc.) and one or more indicators for adults (e.g. petit adult, normal adult, bariatric adult). Alternatively, there may be different delivery devices 10 for children and adults. When the strap 105 is wrapped around the injection site, the indicator 109 appropriate for a particular patient may aligned with the raised area 104 of the outer layer 50 and the strap 105 may then be fixed in place.

Figure 47:
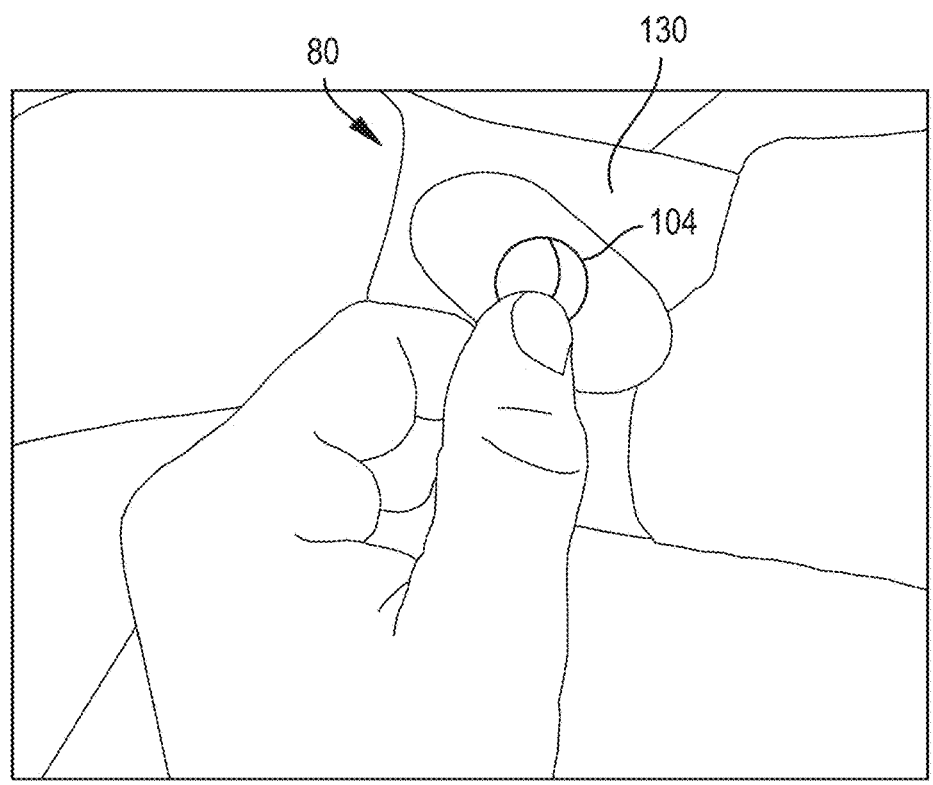
FIG. 47 depicts a view of a user removing a used delivery device from a patient

Referring now to FIG. 47, once the delivery device 10 has been emptied, the first portion 80 may be removed from the injection site (e.g. upper arm 130). The raised area 104 may be at least partially inverted or concave after use and may provide a visual cue that the agent was dispensed from the reservoir 12 (see, e.g. FIG. 26). In certain embodiments, the second portion 82 may be re-associated with the first portion 80 after removal of the first portion 80 from the patient. Thus, the second portion 82 may be used to cover the delivery sharp(s) 72 of a spent delivery device 10.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A delivery device comprising:
   a base portion having an adhesive bearing face;
   a collapsible reservoir;
   at least one delivery sharp;
   a bimetallic actuator positioned in line with the reservoir, and
   at least one heat directing member, the at least one heat directing member including a portion disposed in a plane of the base portion, the heat directing member configured to conduct heat from a surface to which the delivery device is applied to the bimetallic actuator.

2. The delivery device of claim 1, wherein the at least one delivery sharp includes a microneedle.

3. The delivery device of claim 1, wherein the at least one delivery sharp is one of a one dimensional and two dimensional array of microneedles.

4. The delivery device of claim 1, wherein the at least one heat directing member is formed as a wing which extends from a side of the bimetallic actuator.

5. The delivery device of claim 4, wherein the bimetallic actuator includes a first metal portion and a second metal portion, the wing being an extension of one of the first and second metal portion.

6. The delivery device of claim 1, wherein the delivery device includes two heat directing members formed as wings which extend from opposing sides of the bimetallic actuator.

7. The delivery device of claim 1, wherein the bimetallic actuator is configured to bend from an inactive state to an active state, the bimetallic actuator configured to be in the inactive state when subjected to cold chain storage temperatures.

8. The delivery device of claim 1, wherein the portion of the at least one heat directing member disposed in the plane of the base portion includes an adhesive bearing face.

9. The delivery device of claim 1, wherein the at least one heat directing member is metallic.

10. The delivery device of claim 1, wherein the collapsible reservoir includes a wall portion having at least one metallic layer.

11. The delivery device of claim 1, wherein the collapsible reservoir is filled with a vaccine when in a filled state.

12. The delivery device of claim 1, wherein the reservoir is filled with a SARS-COV-2 vaccine selected from a group consisting of a whole virus vaccine, an attenuated virus vaccine, an inactivated virus vaccine, a nucleic acid based vaccine, a RNA based vaccine, an mRNA vaccine, a viral vector vaccine, a non-replicating viral vector vaccine, a peptide based vaccine, and a subunit vaccine.

13. A delivery device comprising:
   a base portion having an adhesive bearing face;
   at least one heat directing member including a portion disposed in a plane of the base portion;
   a collapsible reservoir;
   at least one delivery sharp; and
   a force generating member in line with the reservoir and having an inactive state in which no force is generated by the force generating member and an active state in which the force generating member applies a force to the reservoir, the force generating member configured to automatically transition from the inactive state to the active state when the force generating member is subjected to a temperature condition.

14. The delivery device of claim 13, wherein the at least one delivery sharp includes a microneedle.

15. The delivery device of claim 13, wherein the at least one delivery sharp is one of a one dimensional and two dimensional array of microneedles.

16. The delivery device of claim 13, wherein the at least one heat directing member is continuous with a portion of the force generating member.

17. The delivery device of claim 13, wherein the at least one heat directing member is metallic.

18. The delivery device of claim 13, wherein the portion of the at least one heat directing member disposed in the plane of the base portion includes an adhesive bearing face.

19. The delivery device of claim 13, wherein the delivery device includes two heat directing members formed as wings which extend from opposing sides of the force generating member.

20. The delivery device of claim 13, wherein the temperature condition is a change in temperature from a cold chain storage temperature to a warmer temperature.

21. The delivery device of claim 13, wherein the force generating member is configured to transition from the inactive state to the active state by bending.

22. The delivery device of claim 13, wherein the collapsible reservoir includes a wall portion having at least one metallic layer.

23. The delivery device of claim 13, wherein the collapsible reservoir is filled with a vaccine.

24. The delivery device of claim 13, wherein the reservoir is filled with a SARS-COV-2 vaccine selected from a group consisting of a whole virus vaccine, an attenuated virus vaccine, an inactivated virus vaccine, a nucleic acid based vaccine, a RNA based vaccine, an mRNA vaccine, a viral vector vaccine, a non-replicating viral vector vaccine, a peptide based vaccine, and a subunit vaccine.

25. The delivery device of claim 13, wherein the force generating member comprises two dissimilar metals.

26. A medical agent delivery device comprising:
   a base portion having an adhesive bearing face;
   a collapsible reservoir;
   at least one delivery sharp; and
   a strip including a bimetallic region in line with the reservoir, the bimetallic region having an inactive state and an active state in which the bimetallic region applies a force to the reservoir, the bimetallic region configured to automatically transition from the inactive state to the active state when the bimetallic region is subjected to a change from a colder temperature to a warmer temperature.

* * * * *